US011013600B2

(12) United States Patent
Schwartz et al.

(10) Patent No.: US 11,013,600 B2
(45) Date of Patent: May 25, 2021

(54) COVERED PROSTHETIC HEART VALVE

(71) Applicant: Edwards Lifesciences Corporation, Irvine, CA (US)

(72) Inventors: Evan T. Schwartz, Huntington Beach, CA (US); Sean Chow, Tustin, CA (US); Sandip Vasant Pawar, Irvine, CA (US); Darshin S. Patel, San Juan Capistrano, CA (US); Chambory Chhe, Irvine, CA (US); Arpit Laddha, Santa Ana, CA (US); Ngoc Huong Thi Nguyen, Costa Mesa, CA (US); Waina Michelle Chu, Tustin, CA (US); Yuanlong Du, Fountain Valley, CA (US); Michael Bukin, Pardes Hana (IL); Boaz Manash, Givat Ada (IL); Sara Haivatov, Or-Akiva (IL); Tamir S. Levi, Zikhron Yaakov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 312 days.

(21) Appl. No.: 16/252,890

(22) Filed: Jan. 21, 2019

(65) Prior Publication Data

US 2019/0192296 A1 Jun. 27, 2019

Related U.S. Application Data

(63) Continuation of application No. PCT/US2019/014338, filed on Jan. 18, 2019, which
(Continued)

(51) Int. Cl.
*A61F 2/24* (2006.01)
(52) U.S. Cl.
CPC .......... *A61F 2/2442* (2013.01); *A61F 2/2409* (2013.01); *A61F 2/2418* (2013.01);
(Continued)

(58) Field of Classification Search
CPC ........ A61F 2/24; A61F 2/2409; A61F 2/2418; A61F 2/2433; A61F 2/2436;
(Continued)

(56) References Cited

U.S. PATENT DOCUMENTS 3,409,013 A 11/1968 Berry
3,548,417 A 12/1970 Kisher
(Continued)

FOREIGN PATENT DOCUMENTS

DE 2246526 A1 3/1973
DE 0144167 C 6/1985
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13, pp. 707-708. 1992.
(Continued)

*Primary Examiner* — George J Ulsh
(74) *Attorney, Agent, or Firm* — Edwards Lifesciences; Hans P. Smith

(57) ABSTRACT

A prosthetic heart valve includes a frame having an inflow end and an outflow end, and defining a longitudinal axis. The prosthetic heart valve further includes a leaflet structure situated at least partially within the frame, and a covering disposed around the frame. The covering includes a first woven portion extending circumferentially around the frame and including a plurality of texturized strands or yarns extending along the longitudinal axis of the frame. The covering further includes a second woven portion extending circumferentially around the frame and spaced apart from the first woven portion along the longitudinal axis of the frame. The texturized strands extend along the longitudinal
(Continued)

axis of the frame from the first woven portion to the second woven portion and form a floating portion between the first woven portion and the second woven portion.

24 Claims, 43 Drawing Sheets

Related U.S. Application Data is a continuation-in-part of application No. 15/876,053, filed on Jan. 19, 2018.

(60) Provisional application No. 62/703,363, filed on Jul. 25, 2018, provisional application No. 62/535,724, filed on Jul. 21, 2017, provisional application No. 62/520,703, filed on Jun. 16, 2017, provisional application No. 62/449,320, filed on Jan. 23, 2017.

(52) U.S. Cl.
CPC .......... *A61F 2/2433* (2013.01); *A61F 2/2436* (2013.01); *A61F 2/2415* (2013.01); *A61F 2220/0075* (2013.01); *A61F 2230/0054* (2013.01); *A61F 2230/0091* (2013.01); *A61F 2250/006* (2013.01); *A61F 2250/0028* (2013.01); *A61F 2250/0069* (2013.01)

(58) Field of Classification Search
CPC .................. A61F 2/2442; A61F 2/2415; A61F 2220/0075; A61F 2230/0054; A61F 2230/0091; A61F 2250/0028; A61F 2250/006; A61F 2250/0069
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,790,843 A | 12/1988 | Carpentier et al. |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,165 A | 9/1996 | Block et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,419,696 B1 | 7/2002 | Ortiz et al. |

(56) References Cited

U.S. PATENT DOCUMENTS

| | | |
|---|---|---|
| 6,425,916 B1 | 7/2002 | Garrison et al. |
| 6,432,134 B1 | 8/2002 | Anson et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,797,002 B2 | 9/2004 | Spence et al. |
| 6,830,564 B2 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,096,554 B2 | 8/2006 | Austin et al. |
| 7,101,395 B2 | 9/2006 | Tremulis et al. |
| 7,125,421 B2 | 10/2006 | Tremulis et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,445,632 B2 | 11/2008 | McGuckin, Jr. et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,637,946 B2 | 12/2009 | Solem et al. |
| 7,655,034 B2 | 2/2010 | Mitchell et al. |
| 7,708,775 B2 | 5/2010 | Rowe et al. |
| 7,737,060 B2 | 6/2010 | Strickler et al. |
| 7,785,366 B2 | 8/2010 | Maurer et al. |
| 7,951,195 B2 | 5/2011 | Antonsson et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,142,492 B2 | 3/2012 | Forster et al. |
| 8,167,932 B2 | 5/2012 | Bourang et al. |
| 8,236,049 B2 | 8/2012 | Rowe et al. |
| 8,291,570 B2 | 10/2012 | Eidenscriink et al. |
| 8,323,335 B2 | 12/2012 | Rowe et al. |
| 8,348,998 B2 | 1/2013 | Pintor et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,747,463 B2 | 6/2014 | Fogarty et al. |
| 8,801,776 B2 | 8/2014 | House et al. |
| 9,078,747 B2 | 7/2015 | Conklin |
| 9,078,781 B2 | 7/2015 | Ryan et al. |
| 9,095,434 B2 | 8/2015 | Rowe |
| 9,119,718 B2 | 9/2015 | Keranen |
| 9,192,471 B2 | 11/2015 | Bolling |
| 9,237,886 B2 | 1/2016 | Seguin et al. |
| 9,314,335 B2 | 4/2016 | Konno |
| 9,364,326 B2 | 6/2016 | Yaron |
| 9,370,418 B2 * | 6/2016 | Pintor .................. A61F 2/2412 |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0107535 A1 | 8/2002 | Wei et al. |
| 2002/0138135 A1 | 9/2002 | Duerig et al. |
| 2002/0143390 A1 | 10/2002 | Ishii |
| 2002/0151970 A1 | 10/2002 | Garrison et al. |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2003/0225420 A1 | 12/2003 | Wardle |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0111006 A1 | 6/2004 | Alferness et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Larnbrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0119682 A1 | 6/2005 | Nguyen et al. |
| 2005/0119735 A1 | 6/2005 | Spence et al. |
| 2005/0137691 A1 | 6/2005 | Salahieh et al. |
| 2005/0182486 A1 | 8/2005 | Gabbay |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058672 A1 | 3/2006 | Saiahien et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0195134 A1 | 8/2006 | Crittenden |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2007/0293808 A1 | 12/2007 | Williams et al. |

(56) References Cited

U.S. PATENT DOCUMENTS

| | | |
|---|---|---|
| 2008/0021546 A1 | 1/2008 | Patz et al. |
| 2008/0033542 A1 | 2/2008 | Antonsson et al. |
| 2008/0077235 A1 | 3/2008 | Kirson |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0208330 A1 | 8/2008 | Keranen |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0192601 A1 | 7/2009 | Rafiee et al. |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0036484 A1 | 2/2010 | Hariton et al. |
| 2010/0049313 A1 | 2/2010 | Alon et al. |
| 2010/0082094 A1 | 4/2010 | Quadri et al. |
| 2010/0145440 A1 | 6/2010 | Keranen |
| 2010/0168844 A1 | 7/2010 | Toomes et al. |
| 2010/0185277 A1 | 7/2010 | Braido |
| 2010/0198347 A1 | 8/2010 | Zakay et al. |
| 2010/0204781 A1 | 8/2010 | Alkhatib |
| 2010/0312333 A1 | 12/2010 | Navia et al. |
| 2010/0318184 A1 | 12/2010 | Spence |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton |
| 2012/0059458 A1 | 3/2012 | Buchbinder et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2012/0283820 A1 | 11/2012 | Tseng et al. |
| 2012/0296418 A1 | 11/2012 | Bonyuet et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0190862 A1 | 7/2013 | Pintor et al. |
| 2013/0190865 A1 | 7/2013 | Anderson |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0074299 A1 | 3/2014 | Endou et al. |
| 2014/0081394 A1 | 3/2014 | Keranen et al. |
| 2014/0172070 A1 | 6/2014 | Seguin |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2015/0190227 A1 | 7/2015 | Johnson et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0317305 A1 | 11/2016 | Pelled et al. |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0014229 A1 | 1/2017 | Nguyen-Thien-Nhon et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2018/0000580 A1 | 1/2018 | Wallace et al. |
| 2018/0028310 A1 | 2/2018 | Gurovich et al. |
| 2018/0085217 A1 | 3/2018 | Lashinski et al. |
| 2018/0153689 A1 | 6/2018 | Maimon et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0592410 B1 | 10/1995 |
| EP | 0850607 A1 | 7/1998 |
| EP | 1057460 A1 | 12/2000 |
| EP | 1088529 A2 | 4/2001 |
| EP | 1432369 A1 | 6/2004 |
| EP | 1521550 A2 | 4/2005 |
| EP | 1570809 A1 | 9/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 99/40964 A1 | 8/1999 |
| WO | 99/47075 A1 | 9/1999 |
| WO | 0018333 A1 | 4/2000 |
| WO | 0041652 A1 | 7/2000 |

(56) References Cited

FOREIGN PATENT DOCUMENTS

| | | |
|---|---|---|
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03028558 A2 | 4/2003 |
| WO | 03047468 A1 | 6/2003 |
| WO | 2005034812 | 4/2005 |
| WO | 2005055883 A1 | 6/2005 |
| WO | 2005084595 A1 | 9/2005 |
| WO | 2005102015 A2 | 11/2005 |
| WO | 2006011127 A2 | 2/2006 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A3 | 3/2007 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009155561 A2 | 12/2009 |
| WO | 2010011699 A2 | 1/2010 |
| WO | 2010121076 A2 | 10/2010 |
| WO | 2012063228 A1 | 5/2012 |
| WO | 2013106565 A1 | 7/2013 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015085218 A1 | 6/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017103833 A1 | 6/2017 |
| WO | 2018222799 A1 | 12/2018 |
| WO | 2019032992 A2 | 2/2019 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Trancatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150, pp. 1185-1187. 1986.

\* cited by examiner

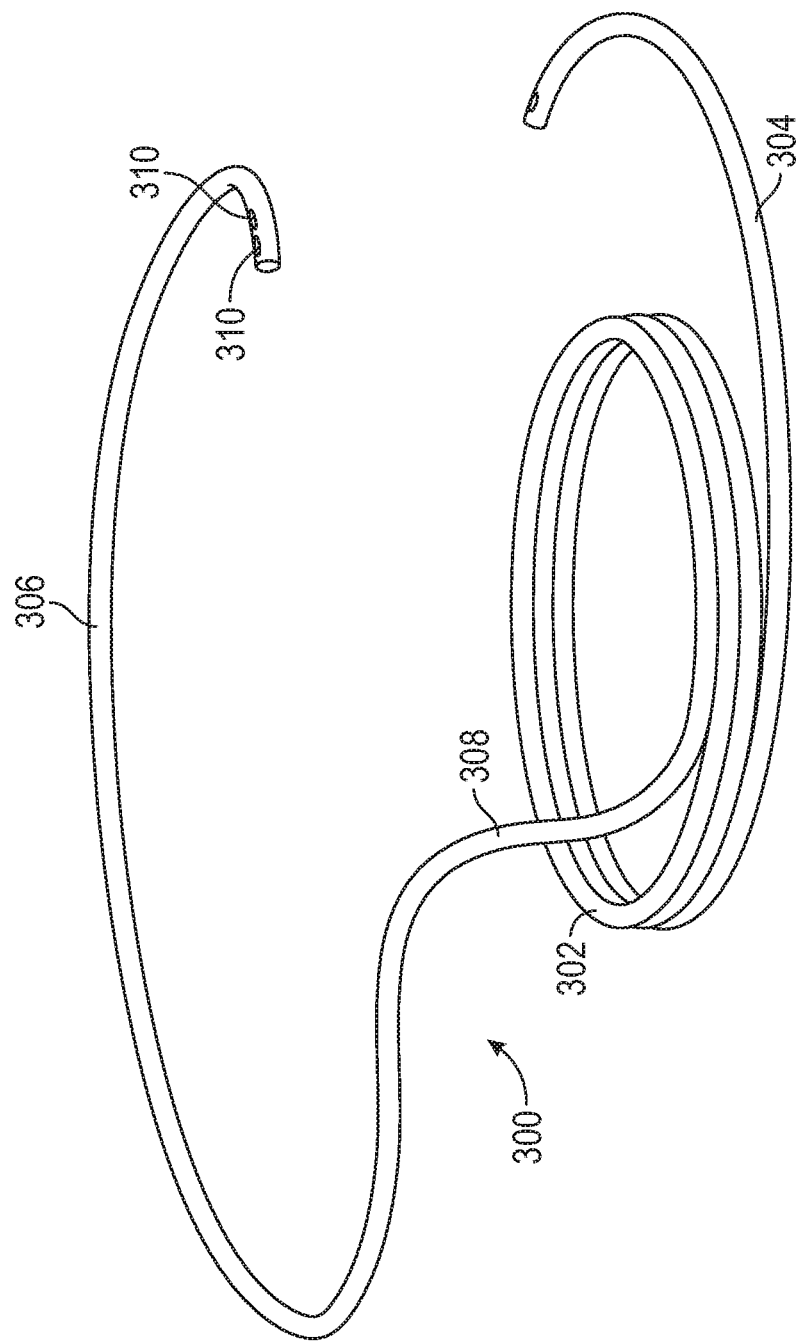

COVERED PROSTHETIC HEART VALVE

CROSS-REFERENCE TO RELATED APPLICATION

The present application is a continuation of PCT Application No. PCT/US2019/014338, filed on Jan. 18, 2019, which is continuation-in-part of U.S. application Ser. No. 15/876,053, filed on Jan. 19, 2018, and which also claims the benefit of U.S. Provisional Application No. 62/703,363, filed on Jul. 25, 2018. Application Ser. No. 15/876,053 claims the benefit of U.S. Provisional Application 62/535,724 filed on Jul. 21, 2017. Application Ser. No. 15/876,053 claims the benefit of U.S. Provisional Application 62/520,703 filed on Jun. 16, 2017. Application Ser. No. 15/876,053 claims the benefit of U.S. Provisional Application 62/449,320 filed on Jan. 23, 2017. Each of the foregoing applications is incorporated by reference in their entirety herein.

FIELD

The present disclosure relates to prosthetic heart valves, and in particular to prosthetic heart valves including a covering.

BACKGROUND

In a procedure to implant a transcatheter prosthetic heart valve, the prosthetic heart valve can be positioned in the annulus of a native heart valve and expanded or allowed to expand to its functional size. In order to retain the prosthetic heart valve at the desired location, the prosthetic heart valve may be larger than the diameter of the native valve annulus such that it applies force to the surrounding tissue in order to prevent the prosthetic heart valve from becoming dislodged. In other configurations, the prosthetic heart valve may be expanded within a support structure that is located within the native annulus and configured to retain the prosthetic heart valve at a selected position with respect to the annulus. Over time, relative motion of the prosthetic heart valve and tissue of the native heart valve (e.g., native valve leaflets, chordae tendineae, etc.) in contact with the prosthetic heart valve may cause damage to the tissue. Accordingly, there is a need for improvements to prosthetic heart valves.

SUMMARY

Certain disclosed embodiments concern coverings for prosthetic heart valves and methods of making and using the same. This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure can be included in the examples summarized here.

In a representative embodiment, a prosthetic heart valve comprises a frame comprising a plurality of strut members, the frame being radially collapsible and expandable between a collapsed configuration and an expanded configuration, the frame having an inflow end and an outflow end, and defining a longitudinal axis. The prosthetic heart valve further comprises a leaflet structure situated at least partially within the frame, and a covering disposed around the frame (e.g., around some, a portion, or all of the frame). The covering can comprise or be formed of a sealing member or cover member, which can be disposed around some or all of the frame to form some or all of the covering. In some embodiments, the covering and/or sealing member/cover member comprises a first woven portion extending circumferentially around the frame and including a plurality of texturized strands (e.g., yarns, threads, sutures, or other elongated materials usable in a similar way to those described herein) extending along the longitudinal axis of the frame. In some embodiments, the covering and/or sealing member/cover member further comprises a second woven portion extending circumferentially around the frame and spaced apart from the first woven portion along the longitudinal axis of the frame. The texturized strands (e.g., yarns, etc.) extend along the longitudinal axis of the frame from the first woven portion to the second woven portion and form a floating portion, such as a floating yarn portion, etc., between the first woven portion and the second woven portion.

In some embodiments, the covering and/or sealing member/cover member is resiliently stretchable between a first state corresponding to the radially expanded configuration of the frame, and a second state corresponding to the radially collapsed configuration of the frame.

In some embodiments, the floating portion/floating yarn portion is resiliently stretchable between the first state and the second state of the covering and/or sealing member/cover member.

In some embodiments, the texturized strands, such as texturized yarns, are configured to provide compressible volume to the floating portion, or to a floating yarn portion, of the covering and/or sealing member/cover member when the frame is in the expanded configuration.

In some embodiments, the texturized strands (e.g., yarns, etc.) are woven into a leno weave pattern in the first woven portion and in the second woven portion.

In some embodiments, the covering and/or sealing member/cover member defines a plurality of circumferentially spaced-apart openings.

In some embodiments, the openings in the covering and/or sealing member/cover member overlie openings defined by strut members of the frame.

In some embodiments, the openings have been cut into a portion of the sealing member made of a bias cloth or bias fabric to inhibit fraying around the openings.

In some embodiments, the covering and/or sealing member/cover member further comprises a third woven portion on the opposite side of the first woven portion from the floating portion/floating yarn portion, the third woven portion comprising the texturized strands/texturized yarns of the first woven portion.

In some embodiments, the texturized strands/texturized yarns are woven into a plain weave pattern in the third woven portion.

In some embodiments, the third woven portion is folded over apices of strut members at the inflow end of the frame.

In some embodiments, the covering and/or sealing member/cover member further comprises a fourth woven portion on the opposite side of the second woven portion from the floating portion/floating yarn portion. The fourth woven portion comprises the texturized strands/texturized yarns, and the texturized strands/texturized yarns are woven into a plain weave pattern in the fourth woven portion.

In some embodiments, the fourth woven portion comprises a plurality of extension portions that overlie openings defined by the strut members of the frame when the frame is in the expanded configuration.

In some embodiments, the extension portions are tapered in a direction toward the outflow end of the frame.

In some embodiments, the covering and/or sealing member/cover member comprises a first protective portion folded over apices of the strut members at the inflow end of the frame, and the covering and/or sealing member/cover member further comprises a second protective portion folded over apices of the strut members at the outflow end of the frame.

In some embodiments, the frame is a mechanically-expandable frame.

In some embodiments, the frame is a plastically-expandable frame.

In some embodiments, the covering and/or sealing member/cover member comprises a plurality of floating portions (e.g., floating yarn portions, etc.) spaced apart from each other along the longitudinal axis of the frame.

The floating portions or floating yarn portions can be heat set to obtain a desired size and texture, e.g., to make them softer and more texturized.

The prosthetic heart valve can use twisted PET yarns in a warp direction and textured PET yarns in a weft direction. The twisted PET yarns in the warp direction can be arranged to weave in leno pattern and the textured PET yarns in the weft direction can form the floating yarn portion without any weave structure. The sealing members can be heat shrunk to achieve a stretchability between 80-160%. The frame can be a mechanically-expandable frame with the above covering or sealing member thereon.

The covering and/or sealing member can comprises at least one of a low-friction layer or low-friction coating on a least a portion thereof. This can include a low-friction layer over another layer of material and/or low-friction strips or layer over portions of another layer. The low-friction layer or low-friction coating can be formed via electrospinning a low-friction material onto the frame or another layer of the covering and/or sealing member.

The prosthetic heart valve can also comprise strips of material that are helically wrapped around struts and/or apices at one or both ends of the frame.

In another representative embodiment, a prosthetic heart valve comprises a frame comprising a plurality of strut members, the frame having an inflow end and an outflow end, the strut members defining a plurality of openings in the frame at the outflow end of the frame. The prosthetic heart valve further comprises a leaflet structure situated at least partially within the frame, and a covering disposed around the frame (e.g., around some, a portion, or all of the frame). The covering can comprise and can be formed from a sealing member or cover member, which can be disposed around some or all of the frame to form some or all of the covering. The covering and/or sealing member/cover member defines a plurality of openings that are aligned with the openings in the frame.

In some embodiments, the frame comprises an outer surface, and the covering or sealing member/cover member covers the entire outer surface of the frame.

In some embodiments, the covering and/or sealing member/cover member comprises a first portion adjacent the inflow end of the frame including a plush pile layer. The covering and/or sealing member/cover member further comprises a second portion without a pile layer adjacent the outflow end of the frame, and the second portion of the covering and/or sealing member/cover member defines the openings of the covering and/or sealing member/cover member.

The foregoing and other objects, features, and advantages of the disclosed technology will become more apparent from the following detailed description, which proceeds with reference to the accompanying figures.

BRIEF DESCRIPTION OF THE DRAWINGS

FIG. 4C is a perspective view of a representative embodiment of an anchor or docking device.

FIGS. 29-31A are perspective views illustrating a representative method of making the covering of FIG. 27.

DETAILED DESCRIPTION

The present disclosure concerns embodiments of implantable prosthetic heart valves and methods of making and using such devices. In one aspect, a prosthetic heart valve includes a covering or outer covering having a backing layer and a main cushioning layer disposed on the backing layer such that the cushioning layer is oriented radially outward about the circumference of the valve. The cushioning layer can be soft and compliant in order to reduce damage to native tissues of the heart valve and/or of the surrounding anatomy at the implantation site due to, for example, relative movement or friction between the prosthetic valve and the tissue as the heart expands and contracts. The covering can also include an inflow protective portion and an outflow protective portion to cushion the surrounding anatomy and prevent the native tissue of the heart valve from contacting the apices of the strut members of the frame, thereby protecting the surrounding tissue. In one embodiment, the covering can include an inflow strip member and an outflow strip member secured to the cushioning layer and folded over the apices of the strut members to form the inflow and outflow protective portions.

Figure 1:
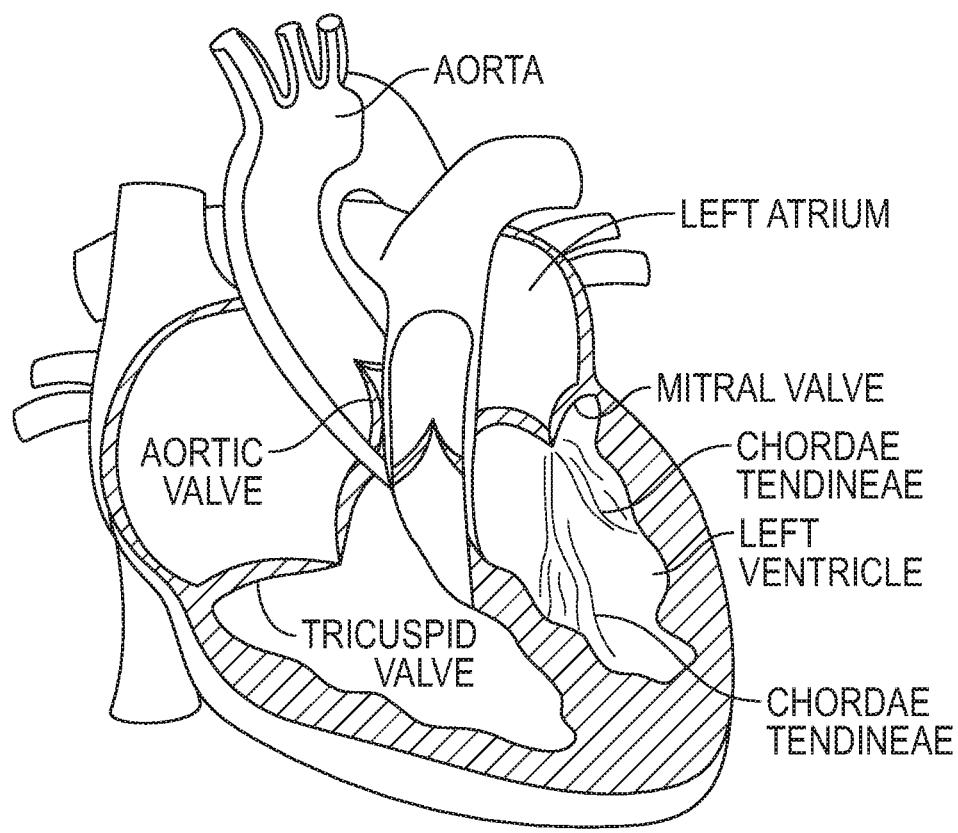
FIG. 1 shows a schematic cross-sectional view of a human heart.
Figure 2:
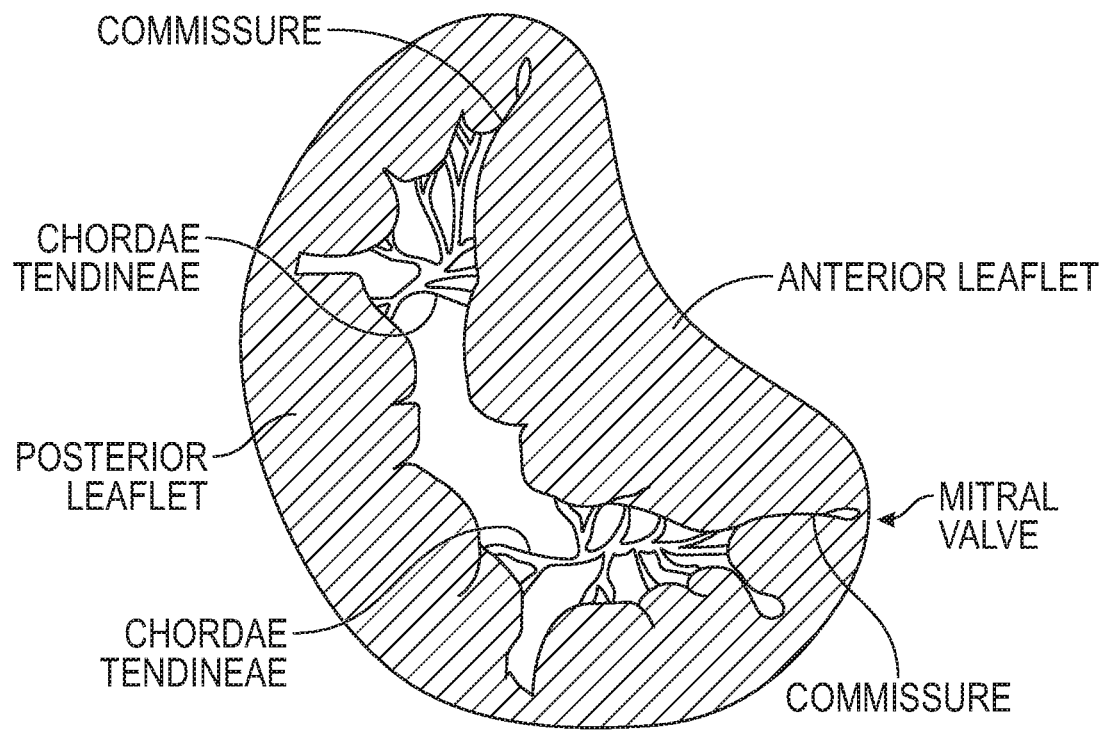
FIG. 2 shows a schematic top view of a mitral valve annulus of a heart.

Embodiments of the disclosed technology can be used in combination with various prosthetic heart valves configured for implantation at various locations within the heart. A representative, non-limiting example is a prosthetic heart valve for replacing the function of the native mitral valve. FIGS. 1 and 2 illustrate the mitral valve of the human heart. The mitral valve controls the flow of blood between the left atrium and the left ventricle. After the left atrium receives oxygenated blood from the lungs via the pulmonary veins, the mitral valve permits the flow of the oxygenated blood from the left atrium into the left ventricle. When the left ventricle contracts, the oxygenated blood that was held in the left ventricle is delivered through the aortic valve and the aorta to the rest of the body. Meanwhile, the mitral valve closes during ventricular contraction to prevent any blood from flowing back into the left atrium.

When the left ventricle contracts, the blood pressure in the left ventricle increases substantially, which urges the mitral valve closed. Due to the large pressure differential between the left ventricle and the left atrium during this time, a possibility of prolapse, or eversion of the leaflets of the mitral valve back into the atrium, arises. A series of chordae tendineae therefore connect the leaflets of the mitral valve to papillary muscles located on the walls of the left ventricle, where both the chordae tendineae and the papillary muscles are tensioned during ventricular contraction to hold the leaflets in the closed position and to prevent them from extending back towards the left atrium. This generally prevents backflow of oxygenated blood back into the left atrium. The chordae tendineae are schematically illustrated in both the heart cross-section of FIG. 1 and the top view of the mitral valve of FIG. 2.

A general shape of the mitral valve and its leaflets as viewed from the left atrium is shown in FIG. 2. Various complications of the mitral valve can potentially cause fatal heart failure. One form of valvular heart disease is mitral valve leak or mitral regurgitation, characterized by abnormal leaking of blood from the left ventricle through the mitral valve back into the left atrium. This can be caused by, for example, dilation of the left ventricle, which can cause incomplete coaptation of the native mitral leaflets resulting in leakage through the valve. Mitral valve regurgitation can also be caused by damage to the native leaflets. In these circumstances, it may be desirable to repair the mitral valve, or to replace the functionality of the mitral valve with that of a prosthetic heart valve, such as a transcatheter heart valve.

Figure 3:
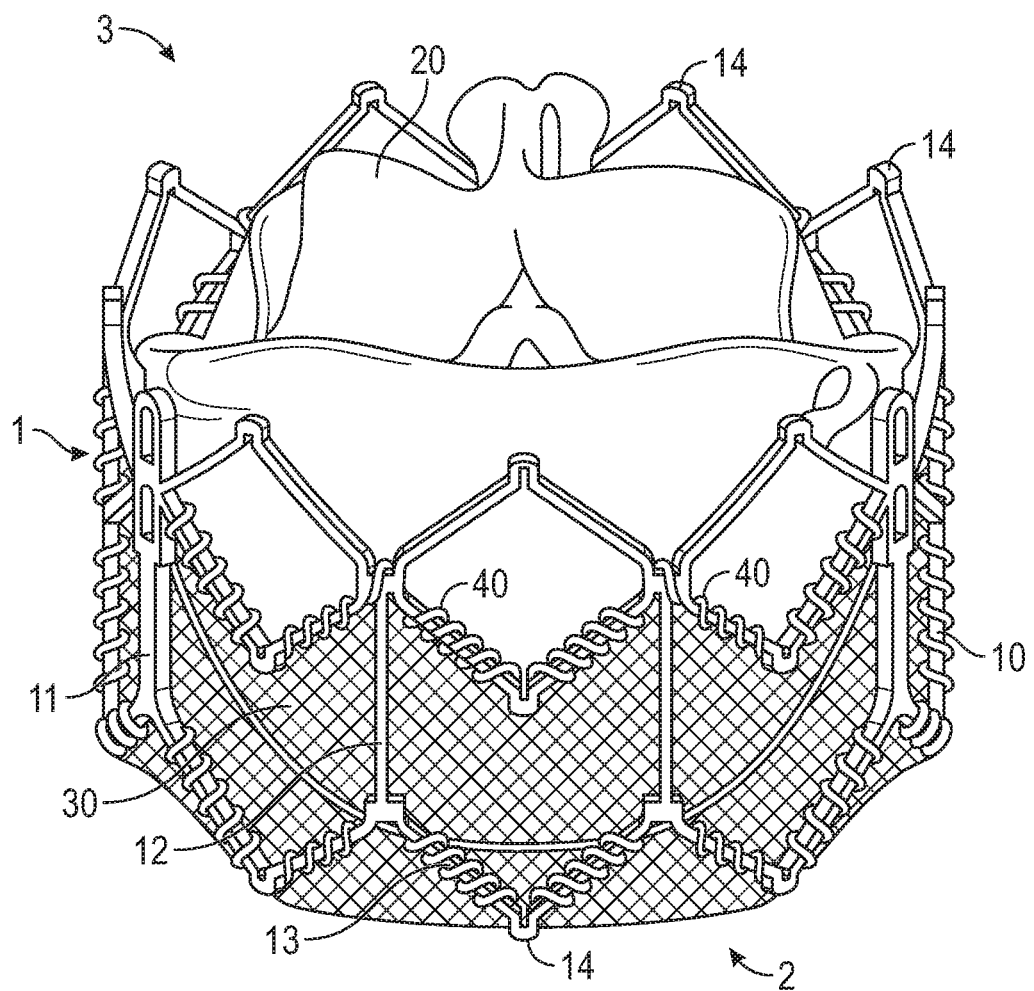
FIG. 3 is a perspective view of an embodiment of a prosthetic heart valve.

Some transcatheter heart valves are designed to be radially crimped or compressed to facilitate endovascular delivery to an implant site at a patient's heart. Once positioned at a native valve annulus, the replacement valve is then expanded to an operational state, for example, by an expansion balloon, such that a leaflet structure of the prosthetic heart valve regulates blood flow through the native valve annulus. In other cases, the prosthetic valve can be mechanically expanded or radially self-expand from a compressed delivery state to the operational state under its own resiliency when released from a delivery sheath. One embodiment of a prosthetic heart valve is illustrated in FIG. 3. A transcatheter heart valve with a valve profile similar to the prosthetic valve shown in FIG. 3 is the Edwards Lifesciences SAPIEN XT™ valve. The prosthetic valve 1 in FIG. 3 has an inflow end 2 and an outflow end 3, includes a frame or stent 10, and a leaflet structure 20 supported inside the frame 10. In some embodiments, a skirt 30 is attached to an inner surface of the frame 10 to form a more suitable attachment surface for the valve leaflets of the leaflet structure 20.

The frame 10 can be made of any body-compatible expandable material that permits both crimping to a radially collapsed state and expansion back to the expanded functional state illustrated in FIG. 3. For example, in embodiments where the prosthetic valve is a self-expandable prosthetic valve that expands to its functional size under its own resiliency, the frame 10 can be made of Nitinol or another self-expanding material. In some embodiments, the prosthetic valve can be a plastically expandable valve that is expanded to its functional size by a balloon or another expansion device, in which case the frame can be made of a plastically expandable material, such as stainless steel or a cobalt chromium alloy. Other suitable materials or combinations of materials can also be used.

The frame 10 can comprise an annular structure having a plurality of vertically extending commissure attachment posts 11, which attach and help shape the leaflet structure 20 therein. Additional vertical posts or strut members 12, along with circumferentially extending strut members 13, help form the rest of the frame 10. The strut members 13 of the frame 10 zig-zag and form edged crown portions or apices 14 at the inflow and outflow ends 2, 3 of the valve 1. Furthermore, the attachment posts 11 can also form edges at one or both ends of the frame 10.

In prosthetic valve 1, the skirt 30 can be attached to an inner surface of the valve frame 10 via one or more threads 40, which generally wrap around to the outside of various struts 11, 12, 13 of the frame 10, as needed. The skirt 30 provides a more substantive attachment surface for portions of the leaflet structure 20 positioned closer to the inflow end 2 of the valve 1.

Figure 4A:
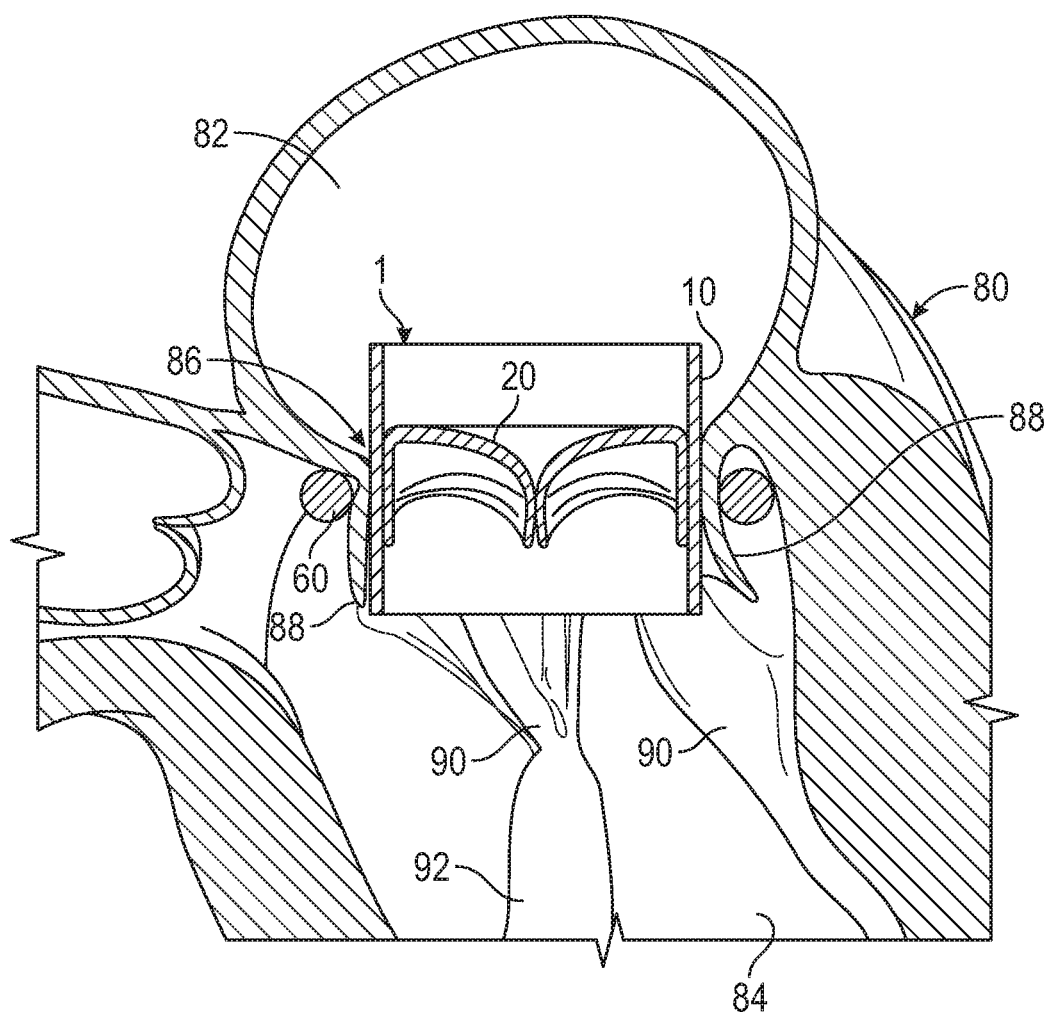
FIG. 4A is a cross-sectional side view of a ring anchor or docking device deployed in a mitral position of the heart, with an implanted valve prosthesis, according to one embodiment.
Figure 4B:
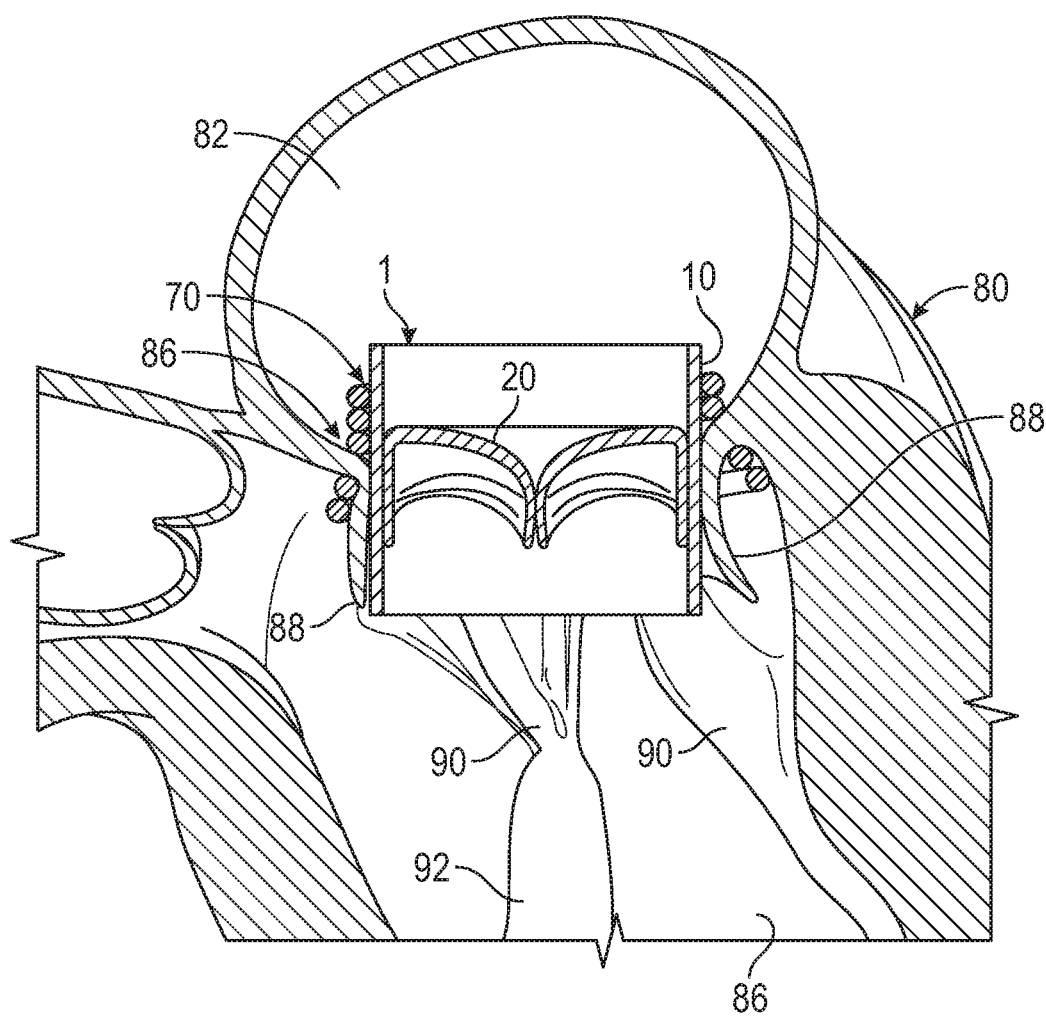
FIG. 4B illustrates a cross-sectional side view of an example of a coil anchor or docking device deployed in the mitral position of the heart, with an implanted valve prosthesis.

FIGS. 4A and 4B show side cross-sectional views of embodiments of different anchors that can be used to facilitate implantation of the valve 1 at a native valve, such as at the mitral valve position or tricuspid valve position of a an animal or patient. As shown, for example, in FIGS. 4A and 4B, a left side of a heart 80 includes a left atrium 82, a left ventricle 84, and a mitral valve 86 connecting the left atrium 82 and the left ventricle 84. The mitral valve 86 includes anterior and posterior leaflets 88 that are connected to an inner wall of the left ventricle 84 via chordae tendineae 90 and papillary muscles 92.

In FIG. 4A, a first anchoring device includes a flexible ring or halo 60 that surrounds the native leaflets 88 of the native valve 86 and/or the chordae tendineae 90. The ring 60 pinches or urges portions of the leaflets inwards, in order to form a more circular opening at the native valve, for more effective implantation of the prosthetic valve 1. The valve prosthesis 1 is retained at the native valve 86 by the ring anchor 60 (which acts as a docking device), and can be delivered to the position shown, for example, by positioning the valve 1 in the native valve 86 while the prosthetic valve 1 is delivered and expanded once it is positioned as shown in FIG. 4A. Once expanded, the prosthetic valve 1 pushes outwardly against the ring anchor 60 to secure the positions of both the valve 1 and the ring anchor 60. In some embodiments, an undersized ring anchor 60 with an inner diameter that is slightly smaller than the diameter of the prosthetic valve 1 in its expanded state can be used, to provide stronger friction between the parts, leading to more secure attachment. As can be seen in FIG. 4A, at least a portion of the native valve leaflets 88 and/or a portion of the chordae tendineae 90 are pinched or sandwiched between the valve 1 and the ring anchor 60 to secure the components to the native anatomy.

FIG. 4B is similar to FIG. 4A, except instead of a ring anchor 60, a helical or coiled anchor or docking device 70 is utilized instead. The helical anchor 70 can include more coils or turns than the ring anchor 60, and can extend both upstream and downstream of the native valve 86. The helical anchor 70 in some situations can provide a greater and more secure attachment area against which the prosthetic valve 1 can abut. Similar to the ring anchor 60 in FIG. 4A, at least a portion of the native valve leaflets 88 and/or the chordae 90 are pinched between the valve 1 and the helical anchor 70. Methods and devices for implanting anchors/docking devices and prosthetic valves, which can be used with the inventions in this disclosure, are described in U.S. application Ser. No. 15/682,287, filed on Aug. 21, 2017 and published as US 2018/0055628, U.S. application Ser. No. 15/684,836, filed on Aug. 23, 2017 and published as US 2018/0055630, and U.S. application Ser. No. 15/984,661, filed on May 21, 2018 and published as US 2018/0318079, which are each incorporated herein by reference.

FIG. 4C illustrates another representative embodiment of an anchor or docking device 300 that can be used in combination with any of the prosthetic valves described herein. The anchor 300 has a functional coil/turn region or central region 302 and an encircling turn or lower region 304. The anchor 300 can also, optionally, have an upper region 306. The lower region 304 includes one or more turns that can be configured to encircle or capture the chordae tendineae and/or the leaflets of a native valve, such as the mitral valve or tricuspid valve. The central region 302 includes a plurality of turns configured to retain the prosthetic valve at the native valve. The upper region 306 can include one or more turns, and can be configured to keep the anchor from being dislodged from the valve annulus prior to implantation of the prosthetic valve. In some embodiments, the upper region 306 can be positioned over the floor of the atrium, and can be configured to keep the turns of the central region 302 positioned high within the native valve apparatus.

The anchor 300 can, optionally, also include an extension portion 308 positioned between the central region 302 and the upper region 306. In some embodiments, the extension portion 308 can instead be positioned, for example, wholly in the central region 302 (e.g., at an upper portion of the central region) or wholly in the upper region 306. The extension portion 308 includes a part of the coil that extends substantially parallel to a central axis of the anchor. In some embodiments, the extension portion 308 can be angled relative to the central axis of the anchor. In some embodiments, the extension portions 308 can be longer or shorter than that shown and can have a larger or smaller angle relative to region 302 and/or region 306. The extension portion 308 can serve to space the central region 302 and the upper region 306 apart from one another in a direction along the central axis so that a gap is formed between the atrial side and the ventricular side of the anchor.

The extension portion 308 of the anchor can be configured to be positioned through, near, and/or around the native valve annulus, in order to reduce the amount of the anchor that passes through, pushes, or rests against the native annulus and/or the native leaflets when the anchor is implanted. This can reduce the force applied by the anchor on the native valve and reduce abrasion of the native leaflets. In one arrangement, the extension portion 308 is positioned at and passes through one of the commissures of the native valve. In this manner, the extension portion 308 can space the upper region 306 apart from the native leaflets of the native valve to prevent the upper region 306 from interacting with the native leaflets from the atrial side. The extension portion 308 also elevates the upper region 306 such that the upper region contacts the atrial wall above the native valve, which can reduce the stress on and around the native valve, as well as provide for better retention of the anchor.

As shown in FIG. 4C, the anchor 300 can further include one or more openings configured as through holes 310 at or near one or both of the proximal and distal ends of the anchor. The through holes 310 can serve, for example, as suturing holes for attaching a cover layer over the coil of the anchor, and/or as an attachment site or tethering holes for delivery tools such as a pull wire, retention member, retention suture, etc. In some embodiments, a width or thickness of the coil of the anchor 300 can also be varied along the length of the anchor. For example, a central portion of the anchor and/or extension 308 can be made thinner than end portions of the anchor. This can allow the central portion and/or extension 308 to exhibit greater flexibility, while the end portions can be stronger or more robust. In certain examples, making the end portions of the coil relatively thicker can also provide more surface area for suturing or otherwise attaching a cover layer to the coil of the anchor.

In certain embodiments, the anchor or docking device 300 can be configured for insertion through the native valve annulus in a counter-clockwise direction. For example, the anchor can be advanced through commissure A3P3, commissure A1P1, or through another part of the native mitral valve. The counter-clockwise direction of the coil of the anchor 300 can also allow for bending of the distal end of the delivery catheter in a similar counter-clockwise direction, which can be easier to achieve than to bend the delivery catheter in the clockwise direction. However, it should be understood that the anchor can be configured for either clockwise or counter-clockwise insertion through the valve, as desired.

Returning to the prosthetic valve example of FIG. 3, the prosthetic valve 1 generally includes a metal frame 10 that forms a number of edges. In addition, many frames 10 are constructed with edged crowns or apices 14 and protruding commissure attachment posts 11, as well as threads 40 that can be exposed along an outer surface of the frame 10. These features can cause damage to the native tissue, such as tissue lodged between the prosthetic valve 1 and the anchor 60, 70, for example, by movement or friction between the native tissue and the various abrasive surfaces of the prosthetic valve 1. In addition, other native tissue in close proximity to the prosthetic valve 1, such as the chordae tendineae, can also potentially be damaged.

Figure 5:
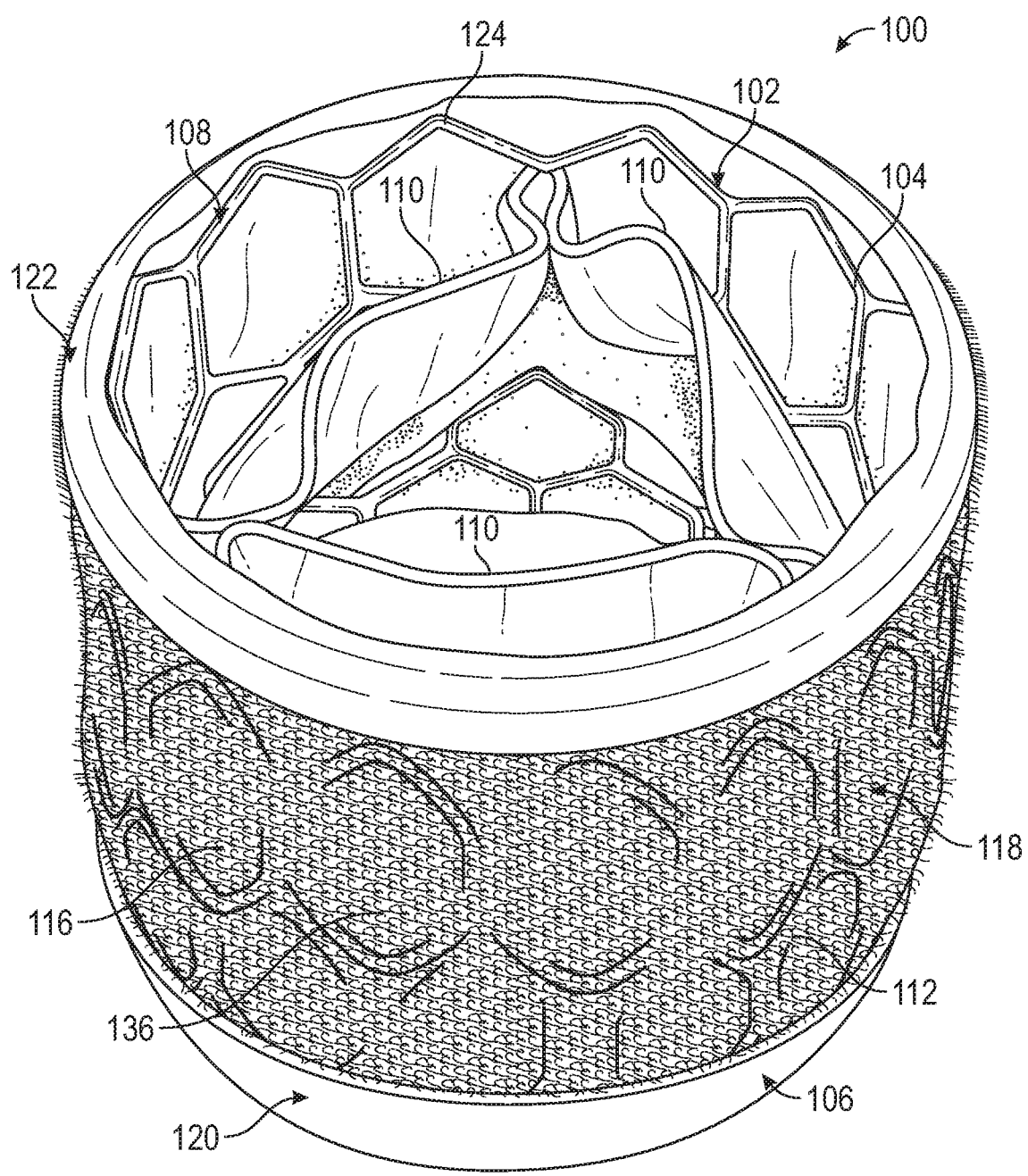
FIG. 5 is a perspective view of a prosthetic heart valve including a representative embodiment of a covering.
Figure 6:
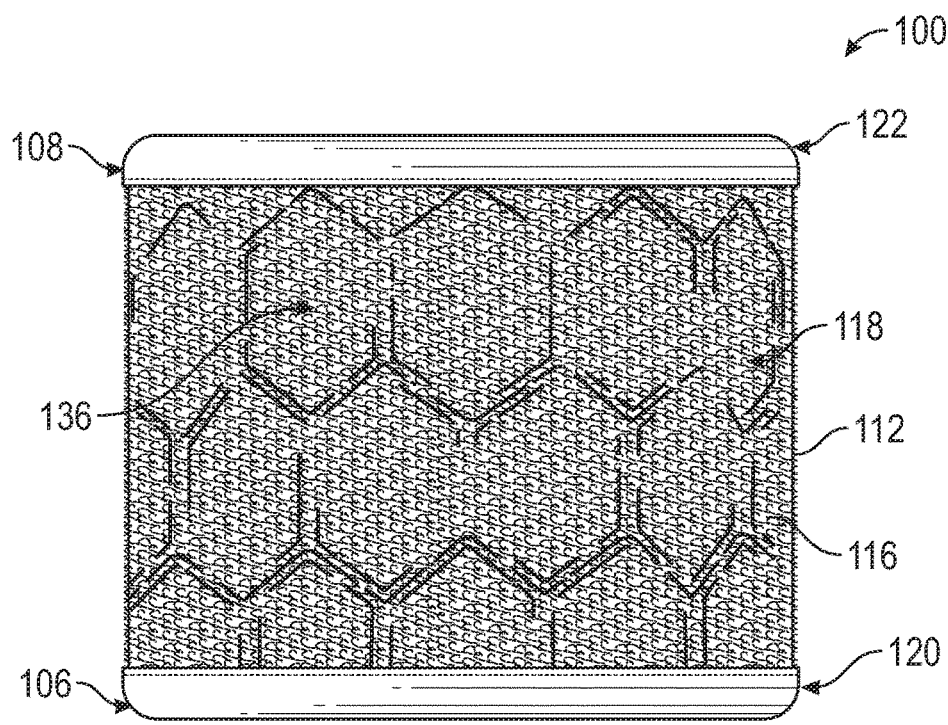
FIG. 6 is a side-elevation view of the prosthetic heart valve of FIG. 5.
Figure 7:
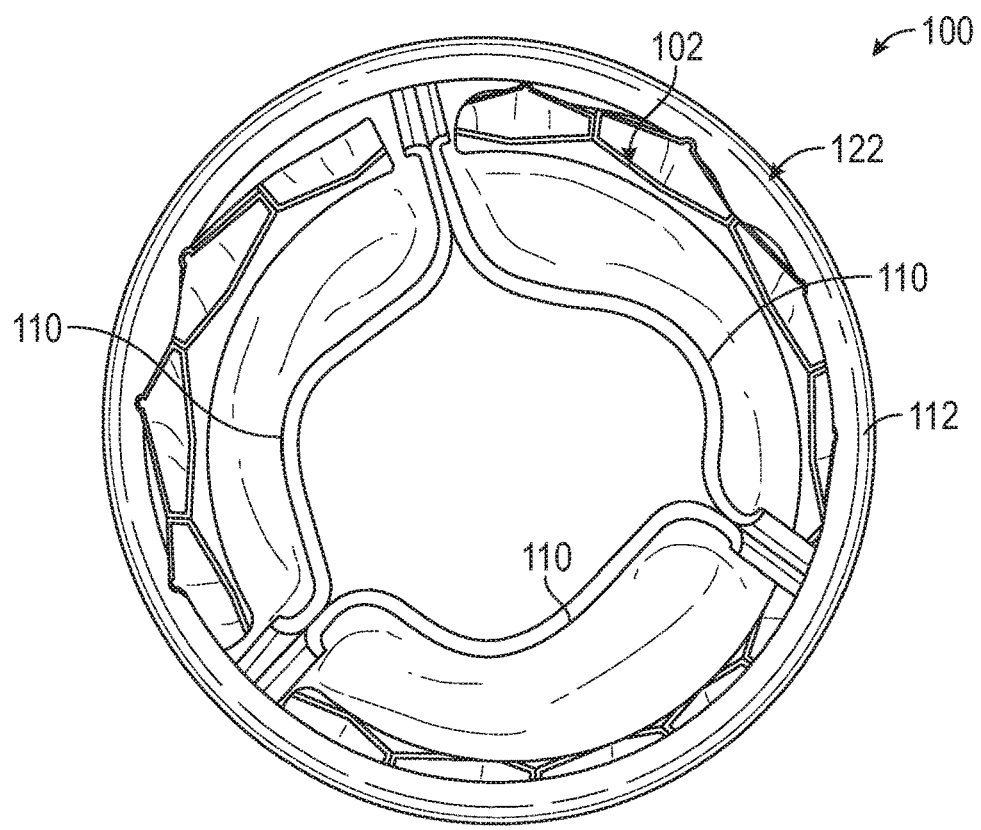
FIG. 7 is a top plan view of the prosthetic heart valve of FIG. 5.

FIGS. 5-7 illustrate a representative embodiment of a prosthetic heart valve 100 similar to the Edwards Lifesciences SAPIEN™ 3 valve, which is described in detail in U.S. Pat. No. 9,393,110, which is incorporated herein by reference. The prosthetic valve 100 includes a frame 102 formed by a plurality of angled strut members 104, and having an inflow end 106 and an outflow end 108. The prosthetic valve 100 also includes a leaflet structure comprising three leaflets 110 situated at least partially within the frame 102 and configured to collapse in a tricuspid arrangement similar to the aortic valve, although the prosthetic valve can also include two leaflets configured to collapse in a bicuspid arrangement in the manner of the mitral valve, or more than three leaflets, as desired. The strut members 104 can form a plurality of apices 124 arranged around the inflow and outflow ends of the frame.

The prosthetic heart valve can include a covering or outer covering 112 configured to cushion (protect) native tissue in contact with the prosthetic valve after implantation, and to reduce damage to the tissue due to movement or friction between the tissue and surfaces of the valve. The covering 112 can also reduce paravalvular leakage. In the embodiment of FIG. 5, the covering 112 includes a first layer configured as a backing layer 114 (see, e.g., FIG. 8), and a second layer configured as a cushioning layer 116. The cushioning layer 116 can be disposed on the backing layer 114, and can comprise a soft, plush surface 118 oriented radially outward so as to protect tissue or objects in contact with the cushioning layer. In the illustrated configuration, the covering 112 also includes an atraumatic inflow protective portion 120 extending circumferentially around the inflow end 106 of the frame, and an atraumatic outflow protective portion 122 extending circumferentially around the outflow end 108 of the frame. The portion of the cushioning layer 116 between the inflow and outflow protective portions 120, 122 can define a main cushioning portion 136. The first layer 114 and the second layer 116 can together form a sealing member or cover member that can be placed around the frame to form the covering 112. The sealing member/cover member can also comprise the protective portions 120, 122.

Figure 8:
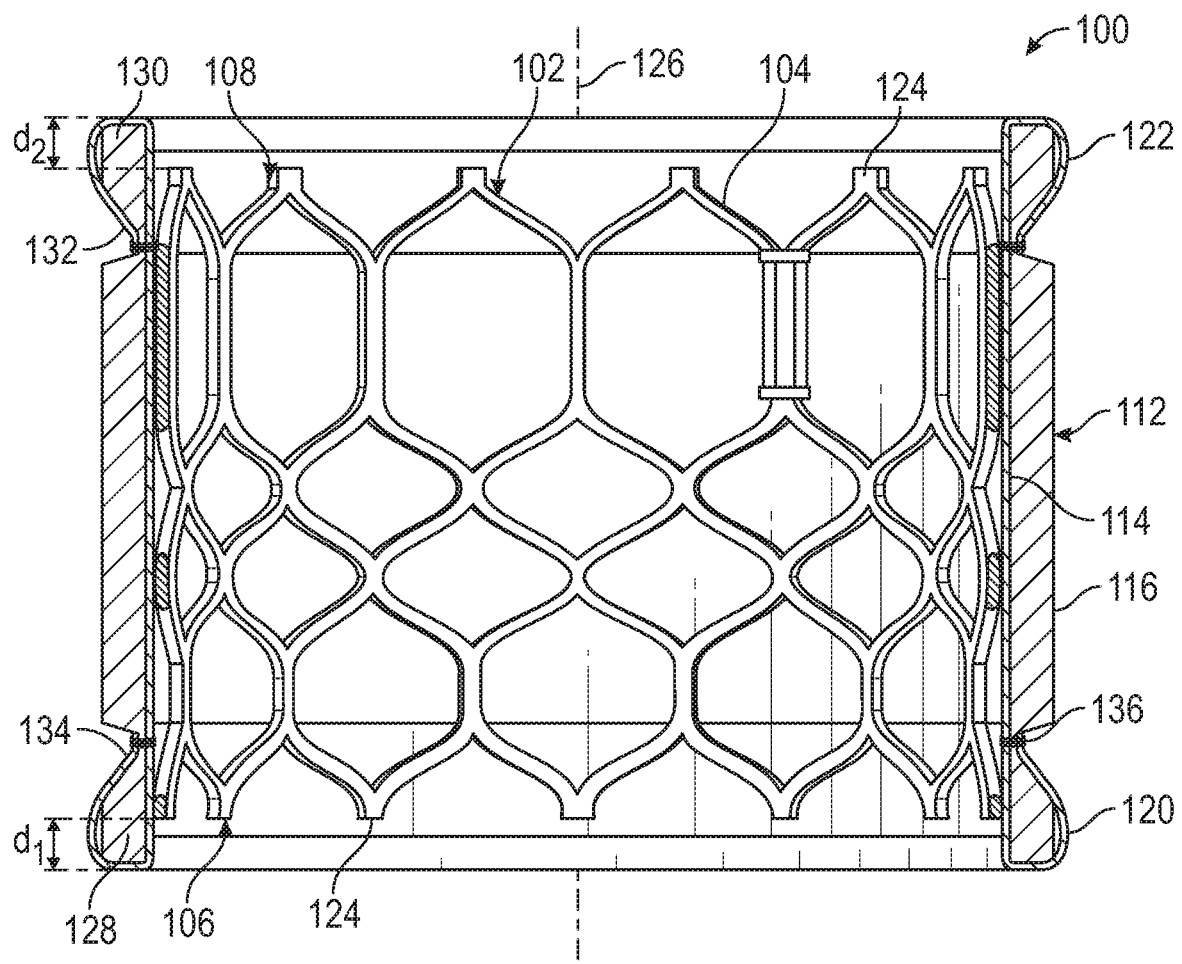
FIG. 8 is a cross-sectional side elevation view of the prosthetic heart valve of FIG. 5.

FIG. 8 is a cross-sectional view schematically illustrating the prosthetic valve 100 with the leaflet structure removed for purposes of illustration. The covering 112 extends around the exterior of the frame 102, such that an interior surface of the backing layer 114 is adjacent or against the exterior surfaces of the strut members 104. As illustrated in FIG. 8, the cushioning layer 116 can have a length that is greater than the length of the frame as measured along a longitudinal axis 126 of the frame. Thus, the covering 112 can be situated such that the cushioning layer 116 extends distally (e.g., in the upstream direction) beyond the apices 124 of the strut members at the inflow end 106 of the frame, with the portion of the cushioning layer extending beyond the apices being referred to herein as distal end portion 128. At the opposite end of the valve, the cushioning layer 116 can extend proximally (e.g., in the downstream direction) beyond the apices 124 of the strut members, with the portion located beyond the apices being referred to as proximal end portion 130. The distances by which the proximal and distal end portions 128, 130 of the cushioning layer 116 extend beyond the apices at the respective end of the valve can be the same or different depending upon, for example, the dimensions of the valve, the particular application, etc.

The backing layer 114 can have sufficient length in the axial direction such that a proximal end portion or flap 132 of the backing layer 114 can be folded over the proximal end portion 130 of the cushioning layer 116 in the manner of a cuff to form the outflow protective portion 122. Meanwhile, a distal end portion or flap 134 of the backing layer 114 can be folded over the distal end portion 128 of the cushioning layer 116 to form the inflow protective portion 120. The proximal and distal flaps 132, 134 of the backing layer 116 can be secured to the underlying section of the backing layer by attachment means, for example, sutures 136, adhesive, clips, etc. In this manner, the inflow and outflow protective portions 120, 122 are constructed such that the proximal and distal end portions 130, 128 of the cushioning layer 116 are at least partially enclosed by the flaps 132, 134 of the backing layer 116. This construction provides sufficient strength and resistance to bending to the inflow and outflow protective portions 120, 122 so that they extend along the longitudinal axis 126 of the valve without bending or otherwise protruding into the inner diameter of the valve (e.g., by bending under their own weight, by blood flow, or by blood pressure). In this manner, the inflow and outflow protective portions 120, 122 minimally impact flow through the prosthetic valve and avoid interfering with the prosthetic valve leaflets, reducing flow disturbances, and potentially reducing the risk of thrombus.

In the illustrated configuration, the inflow protective portion 120 can extend beyond the apices 124 of the strut members at the inflow end of the frame by a distance $d_1$, and the outflow protective portion 122 can extend beyond the apices 124 of the strut members at the outflow end of the frame by a distance $d_2$. The distances $d_1$ and $d_2$ can be the same or different, depending upon the type of prosthetic valve, the treatment location, etc. For example, for a 29 mm prosthetic valve, the distances $d_1$ and $d_2$ can be from about 0.5 mm to about 3 mm. In a representative embodiment, the distances $d_1$ and $d_2$ can be from about 1 mm to about 2 mm. Because the inflow and outflow protective portions 120, 122 extend beyond the apices 124 of the respective ends of the frame, the inflow and outflow protective portions can shield adjacent tissue and/or another implant adjacent the prosthetic valve from contacting the apices 124 of the frame.

Figure 10:
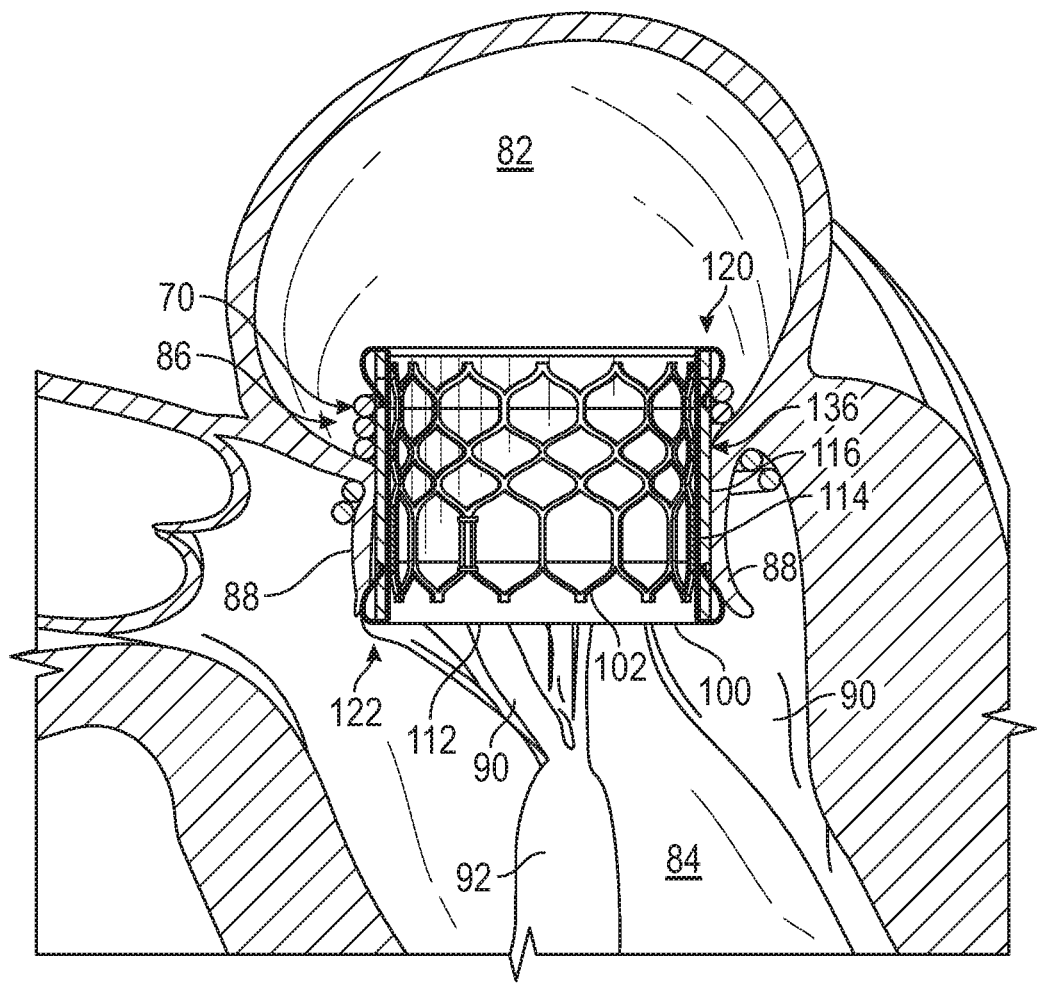
FIG. 10 is a cross-sectional side view of the prosthetic heart valve of FIG. 5 deployed in the mitral position of the heart.

For example, FIG. 10 illustrates the prosthetic valve 100 implanted within an anchor or docking device 70 in the native valve 86, similar to FIGS. 4A and 4B above. In the illustrated example, the inflow end portion of the prosthetic valve is shown positioned above the superior surface of the native valve annulus and spaced from surrounding tissue. However, in other implementations, depending on the axial positioning of the prosthetic valve, which can be varied, the inflow protective portion 120 can contact the native leaflets 88 and prevent them from directly contacting the apices 124 at the inflow end of the frame. Depending on the diameter of the prosthetic valve at the inflow end, the inflow protective portion 120 can serve to prevent the atrium wall from directly contacting the apices 124 at the inflow end of the frame.

As shown in FIG. 10, the anchor 70 can also rest against the compliant inflow protective portion 120. Meanwhile, the portions of the native leaflets 88 captured between the anchor 70 and the prosthetic valve 100 can be cushioned by the plush surface 118 of the main cushioning portion 136. In certain embodiments, the soft, compliant nature and texture of the cushioning layer 116 can increase friction between the native leaflets and the prosthetic valve. This can reduce relative movement of the native leaflets and the prosthetic valve as the left ventricle expands and contracts, reducing the likelihood of damage to the native leaflets and the surrounding tissue. The cushioning layer 116 can also provide increased retention forces between the anchor 70 and the prosthetic valve 100. The plush, compressible nature of the cushioning layer 116 can also reduce penetration of the covering 112 through the openings in the frame 102 caused by application of pressure to the covering, thereby reducing interference with the hemodynamics of the valve. Additionally, the outflow cushioning portion 122 can protect the chordae tendineae 90 from contacting the strut members of the frame, and in particular the apices 124 at the outflow end of the frame, thereby reducing the risk of injury or rupture of the chordae.

The backing layer 114 can comprise, for example, any of various woven fabrics, such as gauze, polyethylene terephthalate (PET) fabric (e.g., Dacron), polyester fabric, polyamide fabric, or any of various non-woven fabrics, such as felt. In certain embodiments, the backing layer 114 can also comprise a film including any of a variety of crystalline or semi-crystalline polymeric materials, such as polytetrafluoroethylene (PTFE), PET, polypropylene, polyamide, polyetheretherketone (PEEK), etc. In this manner, the backing layer 114 can be relatively thin and yet strong enough to allow the covering 112 to be sutured to the frame, and to allow the prosthetic valve to be crimped, without tearing.

Figure 9:
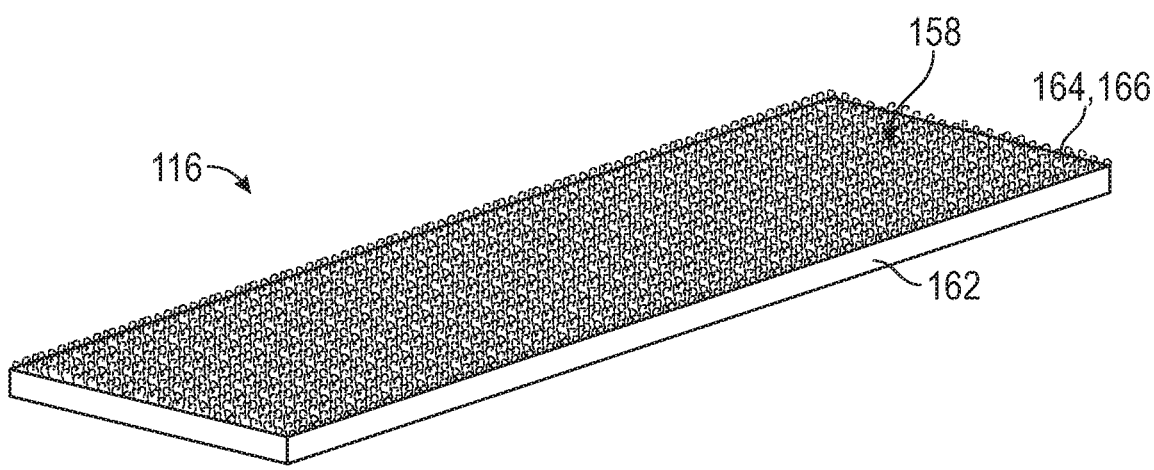
FIG. 9 is a perspective view of a representative embodiment of a cushioning layer including a plush pile.

As stated above, the cushioning layer 116 can comprise at least one soft, plush surface 118. In certain examples, the cushioning layer 116 can be made from any of a variety of woven or knitted fabrics wherein the surface 116 is the surface of a plush nap or pile of the fabric. Exemplary fabrics having a pile include velour, velvet, velveteen, corduroy, terrycloth, fleece, etc. FIG. 9 illustrates a representative embodiment of the cushioning layer 116 in greater detail. In the embodiment of FIG. 9, the cushioning layer 116 can have a base layer 162 (a first layer) from which the pile 158 (a second layer) extends. The base layer 162 can comprise warp and weft strands (e.g., yarns, etc.) woven or knitted into a mesh-like structure. For example, in a representative configuration, the strands/yarns of the base layer 162 can be flat strands/yarns with a denier range of from about 7 dtex to about 100 dtex, and can be knitted with a density of from about 20 to about 100 wales per inch and from about 30 to about 110 courses per inch. The strands/yarns can be made from, for example, biocompatible thermoplastic polymers such as PET, Nylon, ePTFE, etc., other suitable natural or synthetic fibers, or soft monolithic materials.

Figure 11:
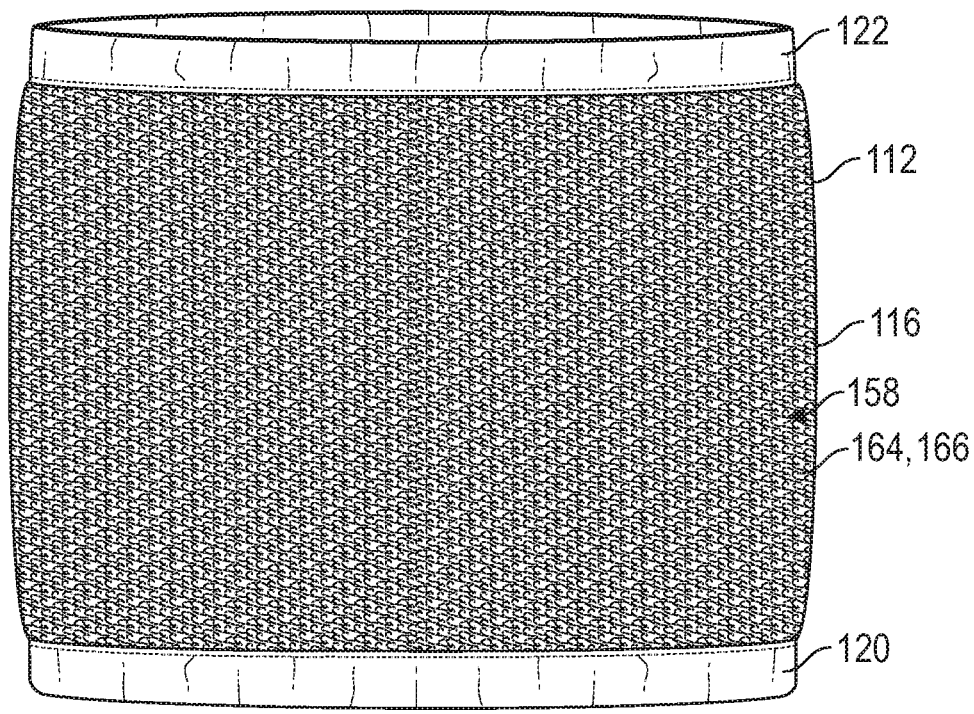
FIG. 11 is a side elevation view of a prosthetic heart valve including an example of a covering.

The pile 158 can comprise pile strands or pile yarns 164 woven or knitted into loops. In certain configurations, the pile strands or pile yarns 164 can be the warp strands/yarns or the weft strands/yarns of the base layer 162 woven or knitted to form the loops. The pile strands or pile yarns 164 can also be separate strands/yarns incorporated into the base layer, depending upon the particular characteristics desired. In certain embodiments, the loops can be cut such that the pile 158 is a cut pile in the manner of, for example, a velour fabric. FIGS. 5-8 illustrate a representative embodiment of the cushioning layer 116 configured as a velour fabric. In some embodiments, the loops can be left intact to form a looped pile in the manner of, for example, terrycloth. FIG. 9 illustrates a representative embodiment of the cushioning layer 116 in which the pile strands or pile yarns 164 are knitted to form loops 166. FIG. 11 illustrates an embodiment of the covering 112 incorporating the cushioning layer 116 of FIG. 9.

In some configurations, the pile strands or pile yarns 164 are textured strands/yarns having an increased surface area due to, for example, a wavy or undulating structure. In configurations such as the looped pile embodiment of FIG. 11, the loop structure and the increased surface area provided by the textured strands or textured yarn of the loops 166 can allow the loops to act as a scaffold for tissue growth into and around the loops of the pile. Promoting tissue growth into the pile 158 can increase retention of the valve at the implant site and contribute to long-term stability of the valve.

The cushioning layer embodiments described herein can also contribute to improved compressibility and shape memory properties of the covering 112 over known valve coverings and skirts. For example, the pile 158 can be compliant such that it compresses under load (e.g., when in contact with tissue, implants, or the like), and returns to its original size and shape when the load is relieved. This can help to improve sealing between the cushioning layer 116 and, for example, support structures or other devices such as the helical anchor 70 in which the prosthetic valve is deployed, or between the cushioning layer and the walls of the native annulus. The compressibility provided by the pile 158 of the cushioning layer 116 is also beneficial in reducing the crimp profile of the prosthetic valve. Additionally, the covering 112 can prevent the leaflets 110 or portions thereof from extending through spaces between the strut members 104 as the prosthetic valve is crimped, thereby reducing damage to the prosthetic leaflets due to pinching of the leaflets between struts.

In some embodiments, the cushioning layer 116 is made of non-woven fabric such as felt, or fibers such as non-woven cotton fibers. The cushioning layer 116 can also be made of porous or spongey materials such as, for example, any of a variety of compliant polymeric foam materials, or woven or knitted fabrics, such as woven or knitted PET. In some embodiments, the proximal and distal end portions of the cushioning layer 116 of the embodiment of FIG. 11 are free of loops 166, and the inflow and outflow protective portions 120, 122 are formed by folding the base layer 162 back on itself to form cuffs at the inflow and outflow ends of the valve.

Figure 12:
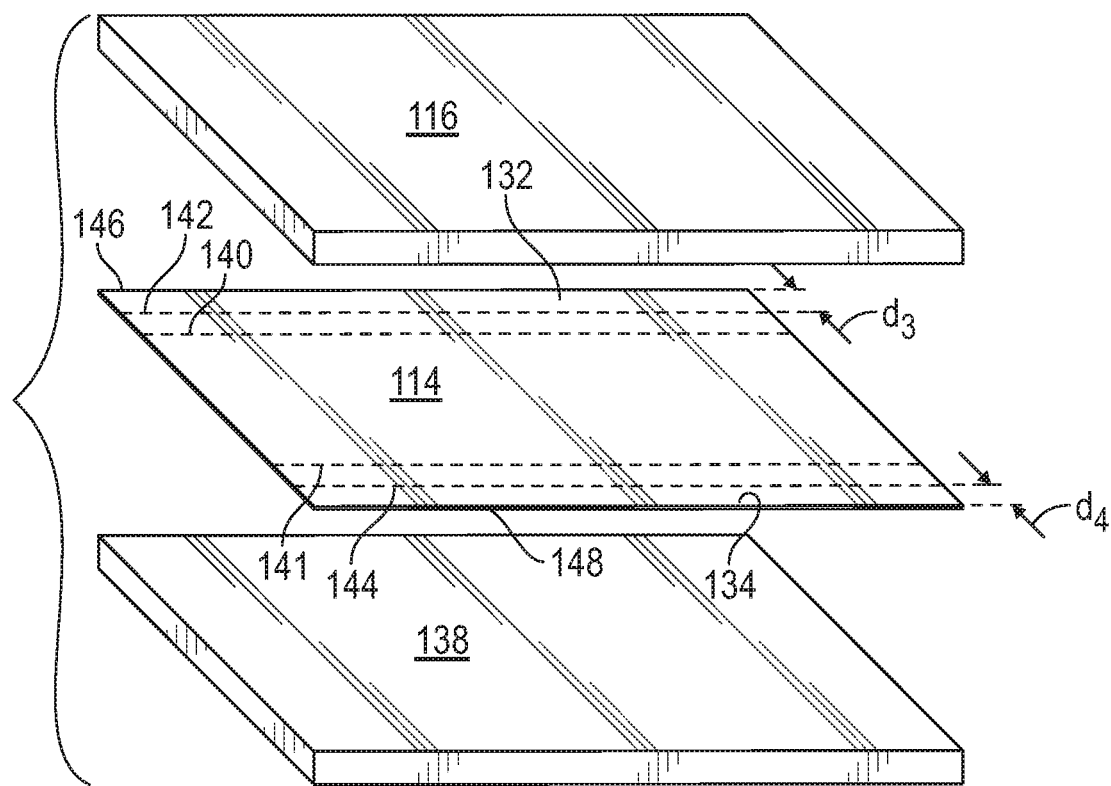
FIG. 12 is a perspective view of a backing layer, a stencil for producing the backing layer, and a cushioning layer, before the backing layer and the cushioning layer are secured together.
Figure 18:
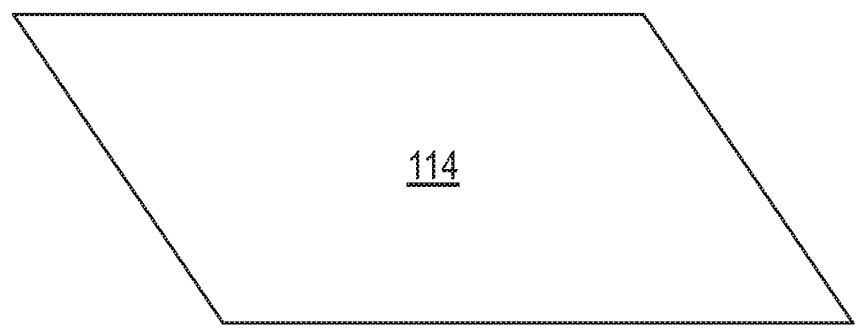
FIG. 18 is a top plan view of an embodiment of a backing layer after it is cut using a parallelogram stencil.

In a representative example illustrated in FIG. 12, the covering 112 of FIGS. 5-8 is made, at least in part, by cutting a fabric material (e.g., a PET fabric) with a stencil 138 to form the backing layer 114. In the illustrated embodiment, the stencil 138 is shaped like a parallelogram, although other configurations and shapes are possible. The angles of the corners of the stencil 138 can be shaped such that the fabric material is cut at about a 45 degree angle relative to the direction of the fibers of the fabric. This can improve the crimpability of the resulting backing layer 114 by, for example, allowing the backing layer to stretch along a direction diagonal to the warp and weft strands/yarns. FIG. 18 illustrates a plan view of a representative example of the backing layer 114 after being cut using the parallelogram stencil 138.

The cushioning layer 116 can be attached (e.g., by sutures, adhesive, etc.) to the backing layer 114. In FIG. 12, the location of the proximal and distal ends of the frame 102 when the covering is attached to the frame are represented as dashed lines 140, 141 on the backing layer 114. Meanwhile, dashed lines 142, 144 represent the location of the proximal and distal edges of the cushioning layer 116 once the cushioning layer is secured to the backing layer. For example, the cushioning layer 116 can be sutured to the backing layer 114 along the proximal and distal edges at or near lines 142, 144. As shown in FIG. 12, line 142 representing the proximal edge of the cushioning layer 116 can be offset from the proximal edge 146 of the backing layer 114 by a distance $d_3$ to create the proximal flap 132. Meanwhile, line 144 representing the distal edge of the cushioning layer 116 can be offset from the distal edge 148 of the backing layer 114 by a distance $d_4$ to create the distal flap 134. The distances $d_3$ and $d_4$ can be the same or different, as desired. For example, depending upon the size of the valve and the size of the inflow and outflow cushioning portions, the distances $d_3$ and $d_4$ can be, for example, about 3-5 mm. In some embodiments, the distances $d_3$ and $d_4$ can be about 3.5 mm.

Once the cushioning layer 116 is secured to the backing layer 114, the resulting swatch can be folded and sutured into a cylindrical shape. The flaps 132, 134 of the backing layer 114 can be folded over the edges of the cushioning layer 116 and sutured to form the inflow and outflow protective portions 120, 122. The resulting covering 112 can then be secured to the frame 102 by attachment means, for example, suturing, clipping, adhering, etc. it to the strut members 104.

Figure 13:
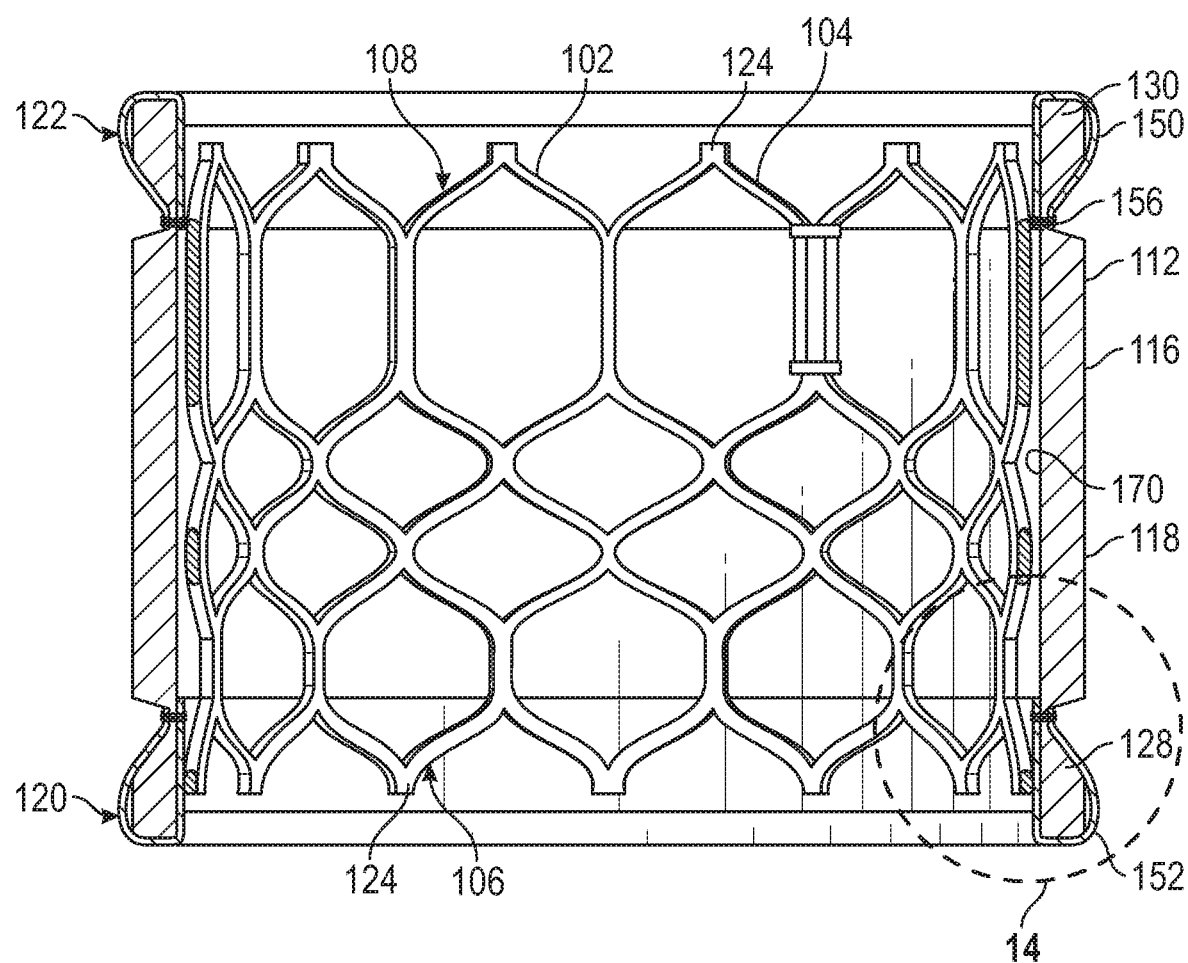
FIG. 13 is a cross-sectional side elevation view of a prosthetic heart valve including an example of a covering.
Figure 14:
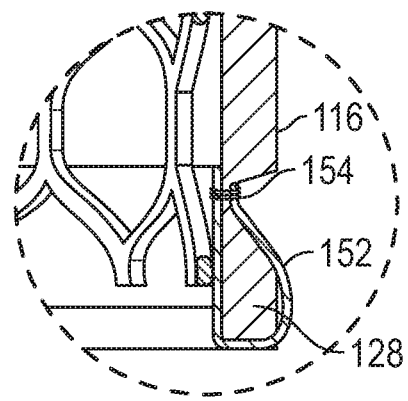
FIG. 14 is a detail view of an inflow protective portion of the covering of FIG. 13.

FIGS. 13 and 14 illustrate an example of the covering 112 in which the inflow and outflow protective portions 120, 122 are formed with separate pieces of material that wrap around the ends of the cushioning layer 116 at the inflow and outflow ends of the valve. For example, the proximal end portion 130 of the cushioning layer 116 can be covered by a member configured as a strip 150 of material that wraps around the cushioning layer from the interior surface 170 (e.g., the surface adjacent the frame) of the cushioning layer 116, over the circumferential edge of the proximal end portion 130, and onto the exterior surface 118 of the cushioning layer to form the outflow protective portion 122.

Likewise, a material strip member 152 can extend from the interior surface 170 of the cushioning layer, over the circumferential edge of the distal end portion 128, and onto the exterior surface of the cushioning layer to form the inflow protective portion 120. The strip members 150, 152 can be sutured to the cushioning layer 116 along the proximal and distal edge portions 130, 128 of the cushioning layer at suture lines 154, 156, respectively.

In certain configurations, the strip members 150, 152 can be made from any of various natural materials and/or tissues, such as pericardial tissue (e.g., bovine pericardial tissue). The strip members 150, 152 can also be made of any of various synthetic materials, such as PET and/or expanded polytetrafluoroethylene (ePTFE). In some configurations, making the strip members 150, 152 from natural tissues such as pericardial tissue can provide desirable properties such as strength, durability, fatigue resistance, and compliance, and cushioning and reduced friction with materials or tissues surrounding the implant.

Figure 15:
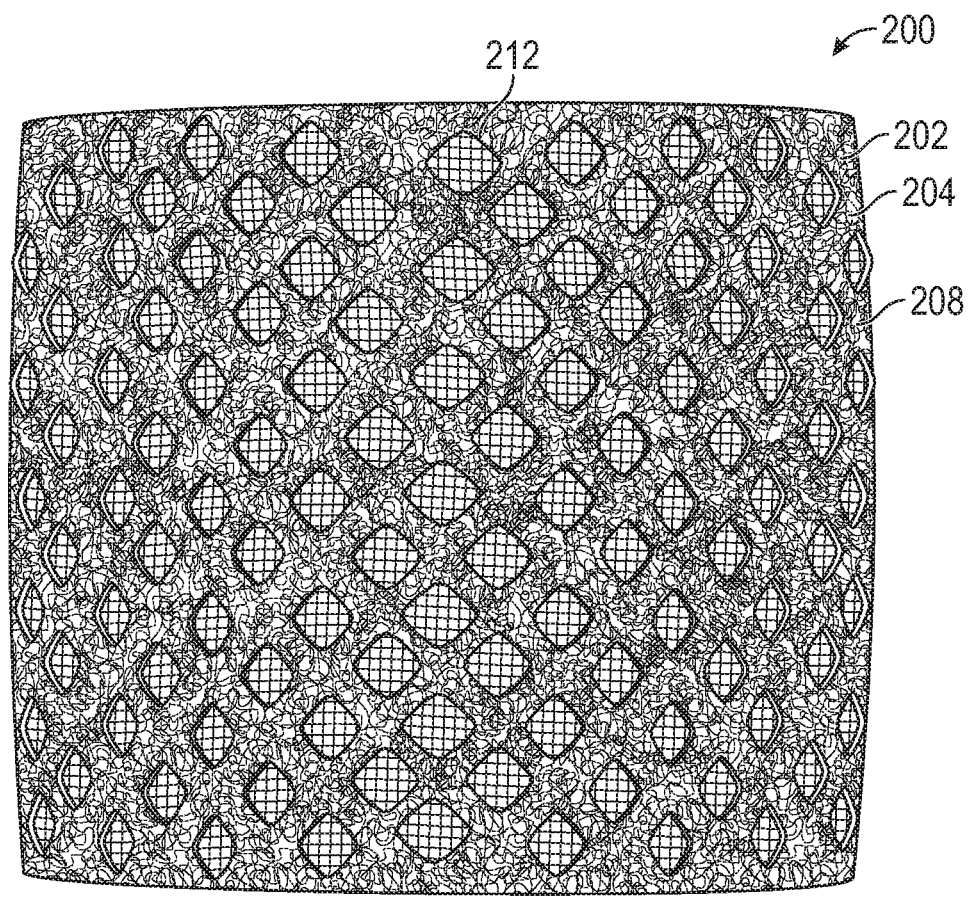
FIG. 15 is a side elevation view of a prosthetic heart valve including an example of a covering comprising a spacer fabric.

FIG. 15 illustrates a prosthetic valve 200 including an example of an outer cover or covering 202 comprising a cushioning layer 204 made of a spacer fabric. In the illustrated embodiment, the outer covering 202 is shown without inflow and outflow protective portions, and with the cushioning layer 204 extending along the full length of the frame from the inflow end to the outflow end of the valve. However, the outer covering 202 may also include inflow and/or outflow protective portions, as described elsewhere herein. The cushioning layer 204 can be or form a sealing member or cover member, which can be attached to the frame to form the covering 202.

Figure 16:
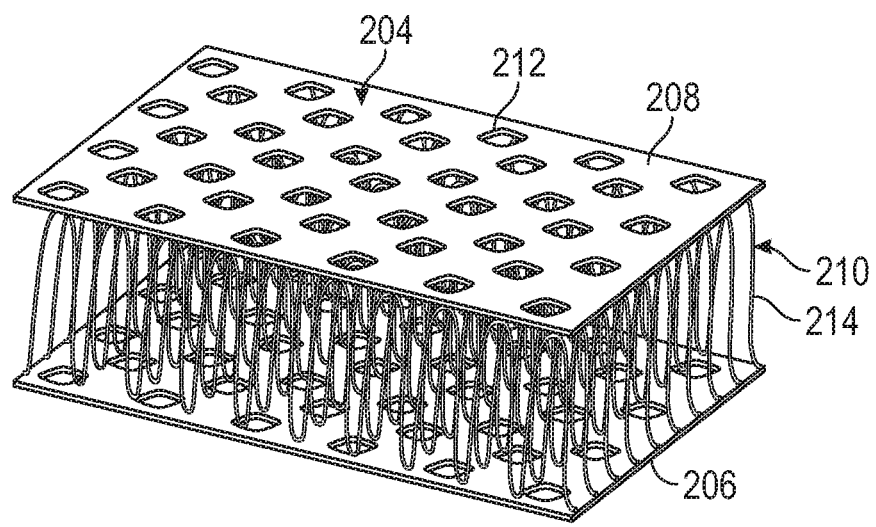
FIG. 16 is a perspective view of a representative embodiment of a spacer cloth including looped pile yarns.
Figure 17:
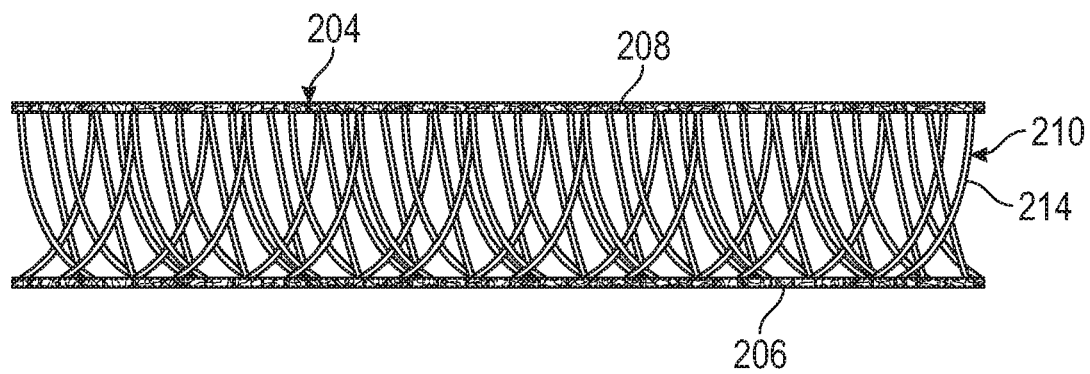
FIG. 17 is a side elevation view of the spacer fabric of FIG. 16.

Referring to FIGS. 16 and 17, the spacer fabric cushioning layer or sealing member/cover member can comprise a first layer 206, a second layer 208, and a spacer layer 210 extending between the first and second layers to create a three-dimensional fabric. The first and second layers 206, 208 can be woven fabric or mesh layers. In certain configurations, one or more of the first and second layers 206, 208 can be woven such that they define a plurality of openings 212. In some examples, openings such as the openings 212 can promote tissue growth into the covering 202. In some embodiments, the layers 206, 208 need not define openings, but can be porous, as desired.

The spacer layer 210 can comprise a plurality of pile strands or pile yarns 214. The pile strands or pile yarns 214 can be, for example, monofilament strands/yarns arranged to form a scaffold-like structure between the first and second layers 206, 208. For example, FIGS. 16 and 17 illustrate an embodiment in which the pile strands or pile yarns 214 extend between the first and second layers 206, 208 in a sinusoidal or looping pattern.

In certain examples, the pile strands or pile yarns 214 can have a rigidity that is greater than the rigidity of the fabric of the first and second layers 206, 208 such that the pile strands or pile yarns 214 can extend between the first and second layers 206, 208 without collapsing under the weight of the second layer 208. The pile strands or pile yarns 214 can also be sufficiently resilient such that the pile strands or pile yarns can bend or give when subjected to a load, allowing the fabric to compress, and return to their non-deflected state when the load is removed.

The spacer fabric can be warp-knitted, or weft-knitted, as desired. Some configurations of the spacer cloth can be made on a double-bar knitting machine. In a representative example, the strands/yarns of the first and second layers 206, 208 can have a denier range of from about 10 dtex to about 70 dtex, and the strands/yarns of the monofilament pile strands/yarns 214 can have a denier range of from about 2 mil to about 10 mil. The pile strands or pile yarns 214 can have a knitting density of from about 20 to about 100 wales per inch, and from about 30 to about 110 courses per inch. Additionally, in some configurations (e.g., warp-knitted spacer fabrics) materials with different flexibility properties may be incorporated into the spacer cloth to improve the overall flexibility of the spacer cloth.

Figure 19:
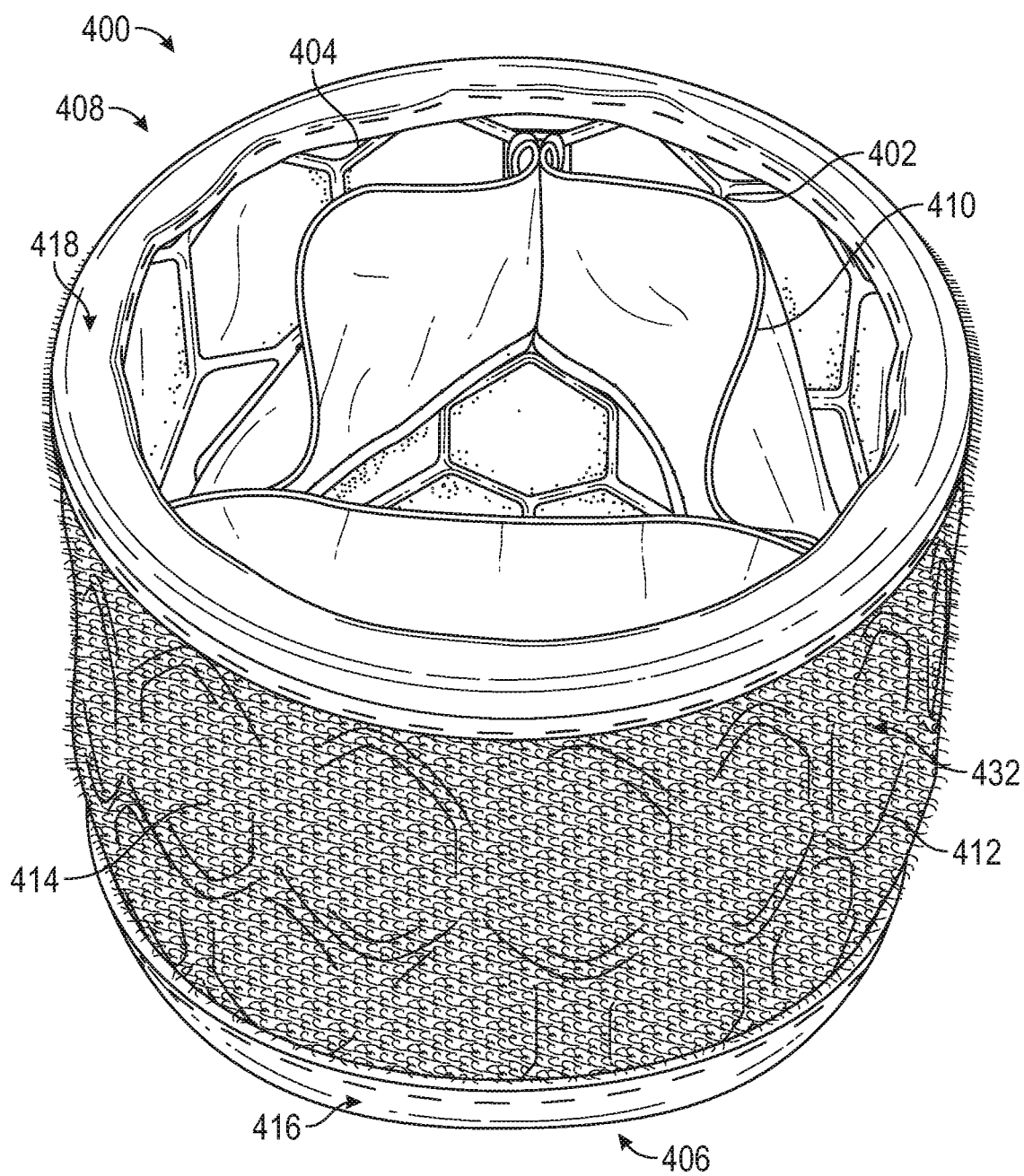
FIG. 19 is a perspective view of a prosthetic heart valve including an example of a covering.
Figure 20:
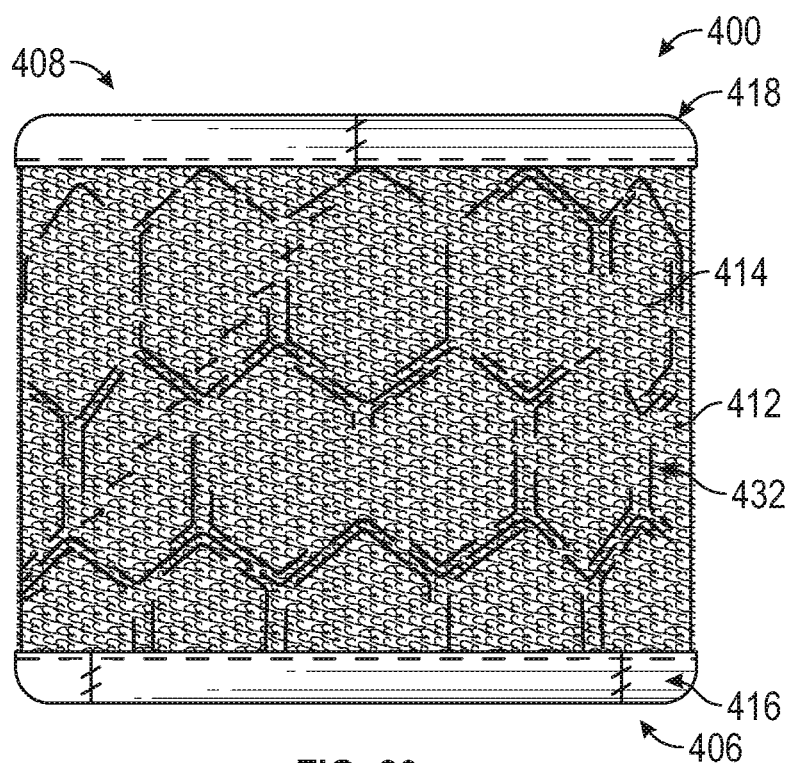
FIG. 20 is a side elevation view of the prosthetic heart valve of FIG. 19.
Figure 21:
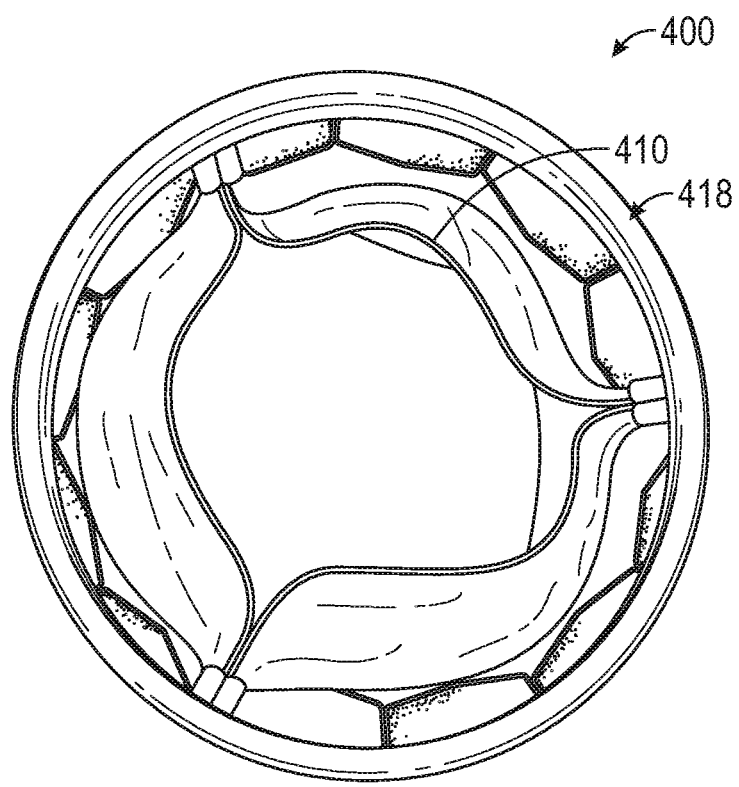
FIG. 21 is a plan view of an outflow end of the prosthetic heart valve of FIG. 19.

FIGS. 19-21 illustrate an example of a prosthetic heart valve 400 including an outer covering with inflow and outflow protective portions that encapsulate the apices of the strut members. For example, the prosthetic valve can include a frame 402 formed by a plurality of strut members 404 defining apices 420 (FIGS. 22 and 24), and can have an inflow end 406 and an outflow end 408. A plurality of leaflets 410 can be situated at least partially within the frame 402.

The prosthetic valve can include a covering or outer covering 412 situated about the frame 402. The outer covering 412 can include a main layer or main cushioning layer 414 including a plush exterior surface 432 (e.g., a first surface), similar to the cushioning layer 116 of FIG. 13 above. The covering 412 can also include an inflow protective portion 416 extending circumferentially around the inflow end 406 of the valve, and an outflow protective portion 418 extending circumferentially around the outflow end 408 of the valve. The inflow and outflow protective portions 416, 418 can be formed with separate pieces of material that are folded around the circumferential ends of the cushioning layer 414 at the inflow and outflow ends of the valve such that the protective portions encapsulate the apices 420 of the strut members. The layer 414 alone or together with protective portions 416, 418 can form a sealing member or cover member that can be placed around the frame to form the covering 412.

Figure 22:
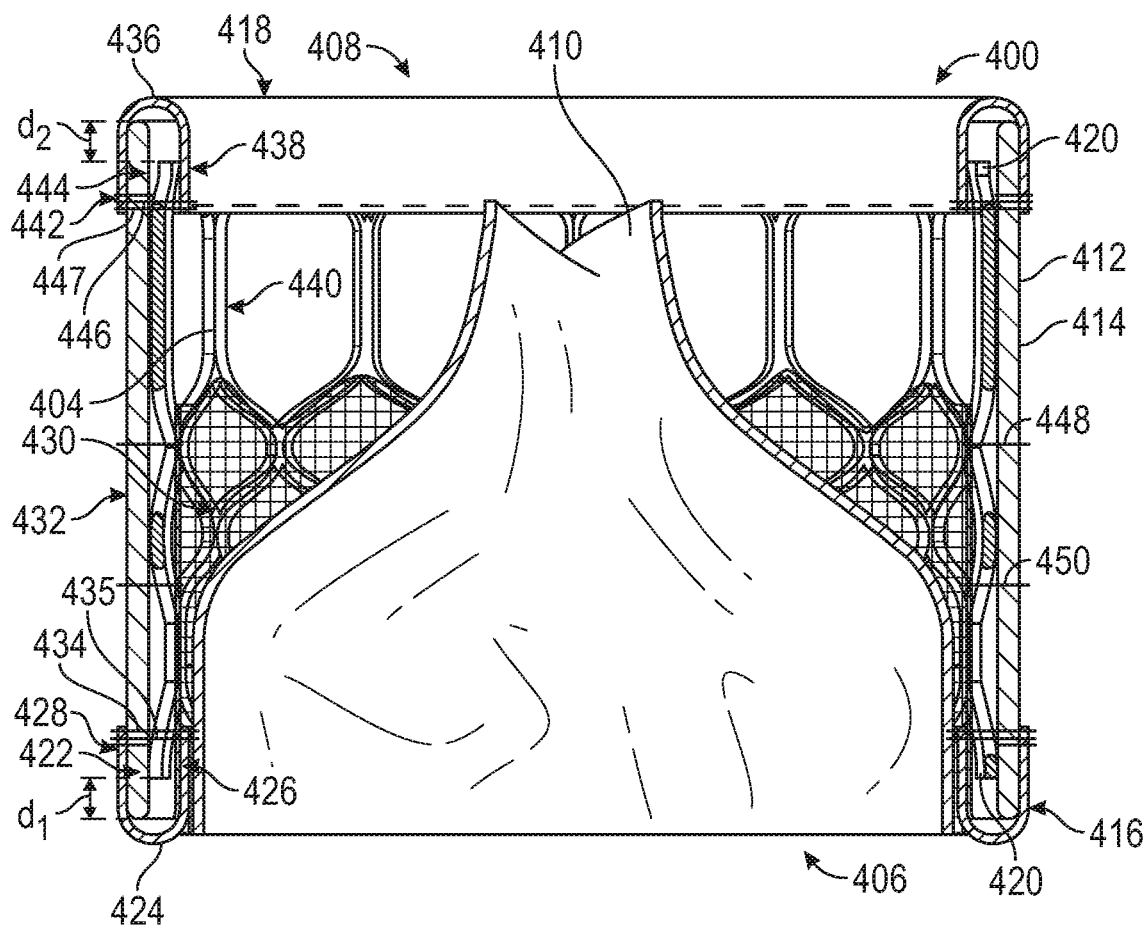
FIG. 22 is a cross-sectional side elevation view of the prosthetic heart valve of FIG. 19.

For example, with reference to FIG. 22, the inflow protective portion 416 can comprise a member configured as a strip 424 of material including a first circumferential edge portion 426 and a second circumferential edge portion 428. The strip member 424 of material can be folded such that the first circumferential edge portion 426 is adjacent (e.g., contacting) an inner skirt 430 disposed within the frame 402. The first circumferential edge portion 426 thereby forms a first or inner layer of the inflow protective portion 416. The strip member 424 can extend over the apices 420 of the strut members, and over an inflow end portion 422 of the cushioning layer 414 such that the second circumferential edge portion 428 is disposed on the exterior surface 432 of the cushioning layer 414. In this manner, the inflow end portion 422 of the cushioning layer 414 can form a second layer of the inflow protective portion 414, and the second circumferential edge portion 428 can form a third or outer layer of the inflow protective portion. The first and second circumferential edge portions 426, 428 of the strip member 424 can be secured to the strut members 404 (e.g., the rung of struts nearest the inflow end 406) with attachment means, such as sutures 434, 435, adhesive, etc. Thus, the strip member 424 can encapsulate the apices 420, along with the inflow end portion 422 of the cushioning layer 414, between the first and second circumferential edge portions 426, 428.

In the illustrated configuration, the inflow protective portion 416 extends beyond the apices 420 of the frame, similar to the embodiments above. In particular, the inflow end portion 422 of the cushioning layer 414 can extend beyond the apices 420 of the frame and into the inflow protective portion 416 within the folded strip 424. In this manner, the inflow end portion 422 of the cushioning layer 414, together with the strip member 424, can impart a resilient, cushioning quality to the inflow protective portion 416. This can also allow the inflow protective portion 416 to resiliently deform to accommodate and protect, for example, native tissue, other implants, etc., that come in contact with the inflow protective portion.

Optionally, one or more additional materials or layers can be included under and/or to form any of the protective portions (e.g., 120, 122, 416, 418, 518, 520, etc.) to provide added cushioning and/or protection at the apices of the frame.

In the illustrated embodiment, the inflow end portion 422 can extend beyond the apices 420 by a distance $d_1$. The distance $d_1$ can be configured such the inflow end portion 422 can extend over or cover the apices 420 when the inflow protective portion 416 comes in contact with, for example, native tissue at the treatment site. The strip member 424 can also form a dome over the edge of the of the inflow end portion 422 such that the edge of the inflow end portion 422 is spaced apart from the domed portion of the strip member 424. In some embodiments, the strip member 424 is folded such that it contacts the edge of the inflow edge portion 422, similar to the embodiment of FIG. 13.

The outflow protective portion 418 can include a member configured as a strip 436 of material folded such that a first circumferential edge portion 438 is adjacent (e.g., contacting) inner surfaces 440 of the strut members, and a second circumferential edge portion 442 is disposed on the exterior surface 432 of the cushioning layer 414, similar to the inflow protective portion 416. An outflow end portion 444 of the cushioning layer 414 can extend beyond the apices 420 by a distance $d_2$, and can be encapsulated by the strip member 436 together with the apices 420 between the first and second circumferential edge portions 438, 442. The distance $d_2$ can be the same as distance $d_1$ or different, as desired. The strip member 436 can be secured to the strut members 404 with attachment means, such as sutures 446, 447, adhesive, etc. The strip member 436 can also form a domed shape similar to the strip member 424.

In certain configurations, the cushioning layer 414 can be a fabric including a plush pile, such as a velour fabric, or any other type of plush knitted, woven, or non-woven material, as described above. In some embodiments, the cushioning layer 414 may also comprise a relatively low thickness woven fabric without a plush pile. In certain configurations, the strip members 424, 436 can be made of resilient natural tissue materials such as pericardium. Optionally, the strip members can also be made from fabric or polymeric materials such as PTFE or ePTFE.

Figure 23:
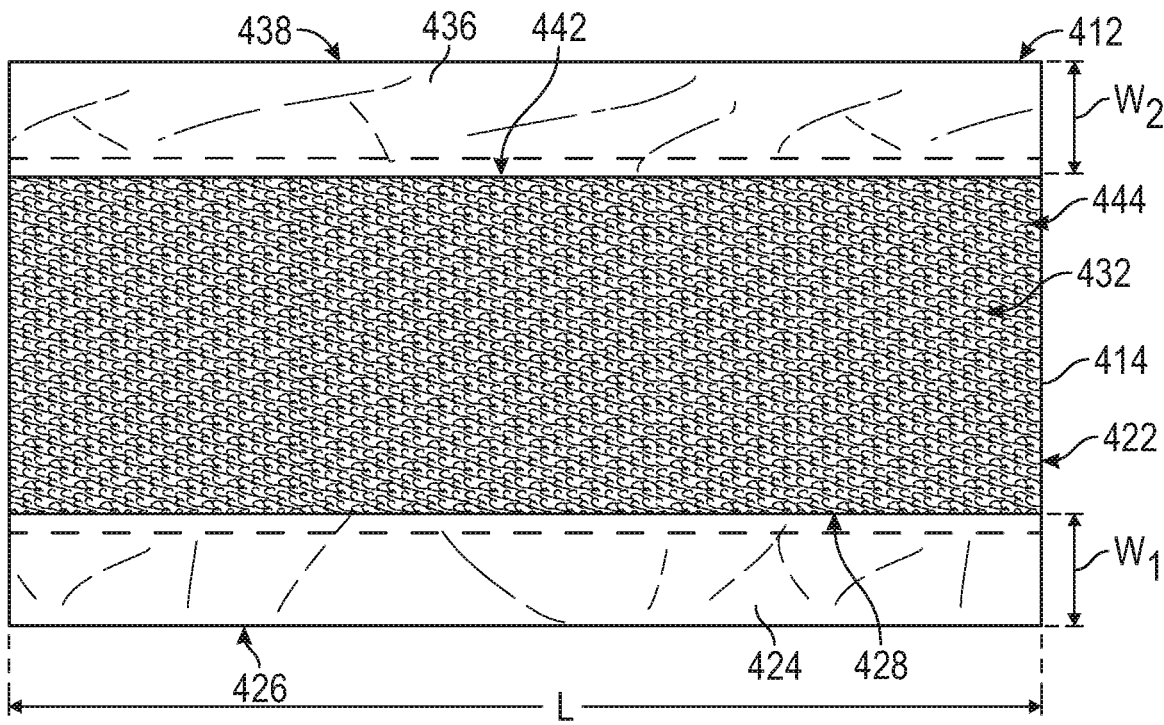
FIG. 23 is a top plan view of the covering of FIG. 19 in an unfolded configuration.

FIGS. 23-26 illustrate a representative method of making the covering or outer covering 412 and attaching the covering to the prosthetic valve 400 to form the inflow and outflow protective portions 416, 418. FIG. 23 illustrates the outer covering 412 in an unfolded configuration prior to securing the covering to the frame 402. As illustrated in FIG. 23, the second circumferential edge portion 428 of the strip member 424 can be sutured to the plush surface 432 (e.g., the first surface) of the cushioning layer 414 at the inflow end portion 422 of the cushioning layer. The second circumferential edge portion 442 of the strip member 436 can be sutured to the plush surface 432 of the cushioning layer 414 at the outflow end portion 444 of the cushioning layer.

In the illustrated configuration, the cushioning layer 414 and the strip members 424, 436 can have a length dimension L corresponding to a circumference of the frame 402. In a representative example, the length dimension L can be about 93 mm. The strip members 424, 436 can also have respective width dimensions $W_1, W_2$. Referring to width dimension $W_1$ for purposes of illustration, the width dimension $W_1$ can be configured such that the strip member 424 extends from the interior of the valve to the exterior of the valve without contacting the apices 420 of the strut members, as shown in FIG. 22. For example, the width dimension $W_1$ can be configured such that the strip member 424 extends from adjacent the rung of strut members 404 at the inflow end 406 of the frame to the exterior of the valve adjacent the same rung of strut members and forms a domed shape over the apices 420. In certain configurations, the width dimension $W_1$ can be about 6 mm. The width dimension $W_2$ can be the same as $W_1$ or different, as desired.

Figure 24:
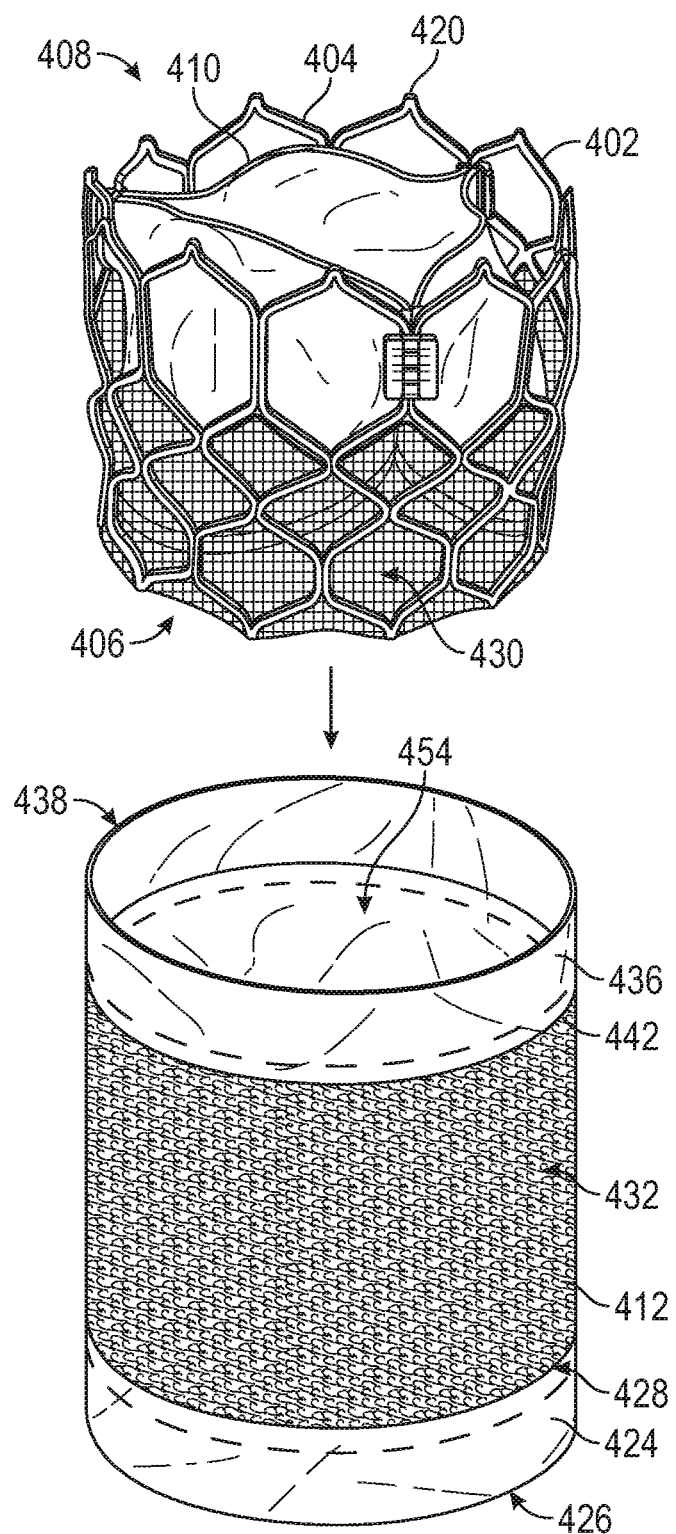
FIG. 24 is a perspective view illustrating placement of the prosthetic heart valve of FIG. 19 into the covering after the covering is formed into a cylindrical shape.

Referring to FIG. 24, the outer covering 412 can be folded and sutured into a cylindrical shape. The outer covering 412 can then be situated around the frame 402 such that a second or interior surface 454 of the cushioning layer 414 is oriented toward the frame. In certain configurations, the frame 402 can already include the inner skirt 430 and the leaflet structure 410, as shown in FIG. 24.

Figure 25:
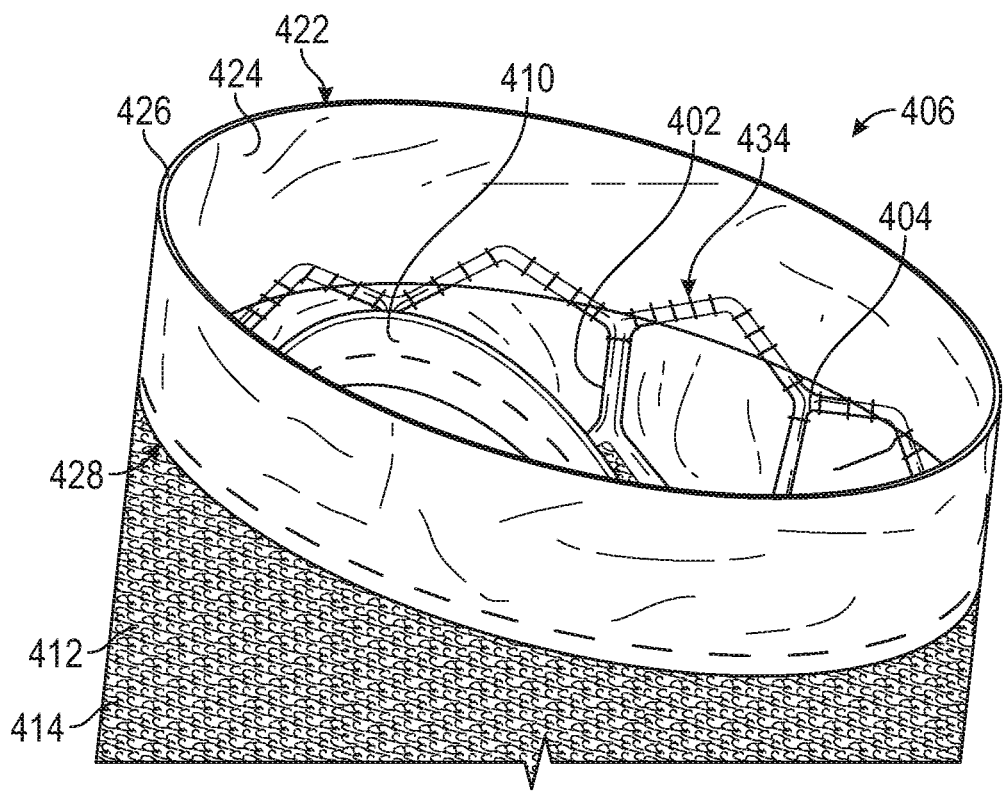
FIG. 25 is a perspective view of the inflow end of the prosthetic heart valve of FIG. 19 illustrating attachment of the covering to the strut members of the valve frame.
Figure 26:
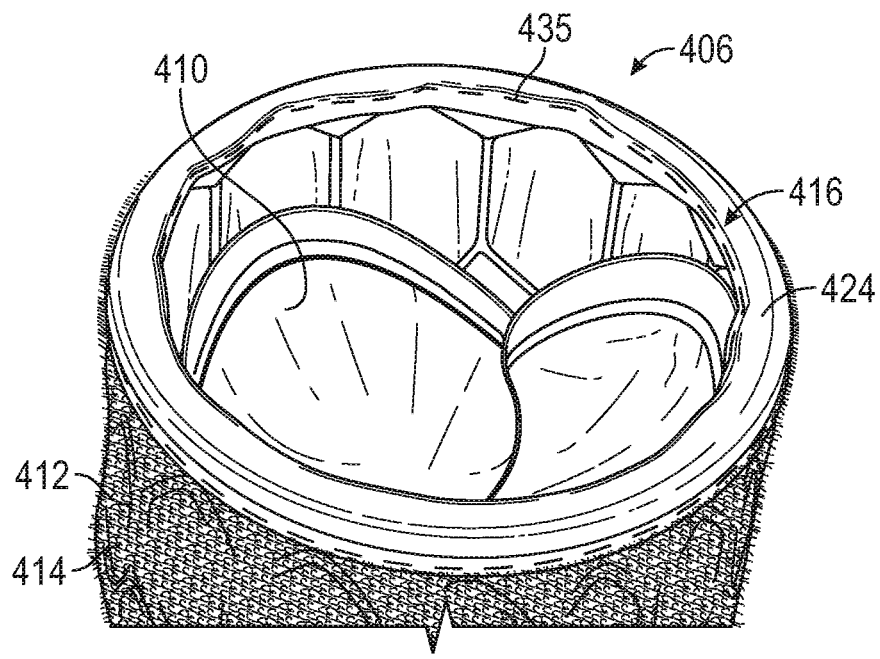
FIG. 26 is a perspective view of the inflow end of the prosthetic heart valve of FIG. 19 illustrating a strip member of the covering folded over the strut members of the valve frame to form an inflow protective portion.

Referring to FIGS. 25 and 26, the outer covering 412 can then be sutured to the frame. For example, as illustrated in FIG. 25, the strip member 424 can be aligned with an adjacent rung of strut members 404 (e.g., the rung of strut members nearest the inflow end of the frame). The cushioning layer 414 and/or the strip member 424 can then be sutured to the strut members 404 at suture line 434. The strip member 424 can then be folded over the apices 420 at the inflow end of the frame, and the first and second circumferential edge portions 426, 428 can be sutured to each other at suture line 435 to form the inflow protective portion 416. In some embodiments, the strip member 424 is folded and sutured to form the inflow protective portion 416 before the outer covering 412 is sutured to the frame.

The outflow protective portion 418 can be formed in a similar manner. For example, the strip member 426 can be aligned with the rung of strut members 404 adjacent the outflow end 408 of the frame, and the strip member 426 and/or the cushioning layer 414 can be sutured to the strut members. The strip member 436 can then be folded over the apices 420 and the cushioning layer 414 at the outflow end of the frame, and the first and second circumferential edge portions 438, 442 can be sutured together, and to the rung of strut members 404 adjacent the outflow end of the frame, to form the outflow protective portion 418. The covering 412 can also be sutured to the frame at one or more additional locations, such as at suture lines 448 and 450, as shown in FIG. 22.

Figure 27:
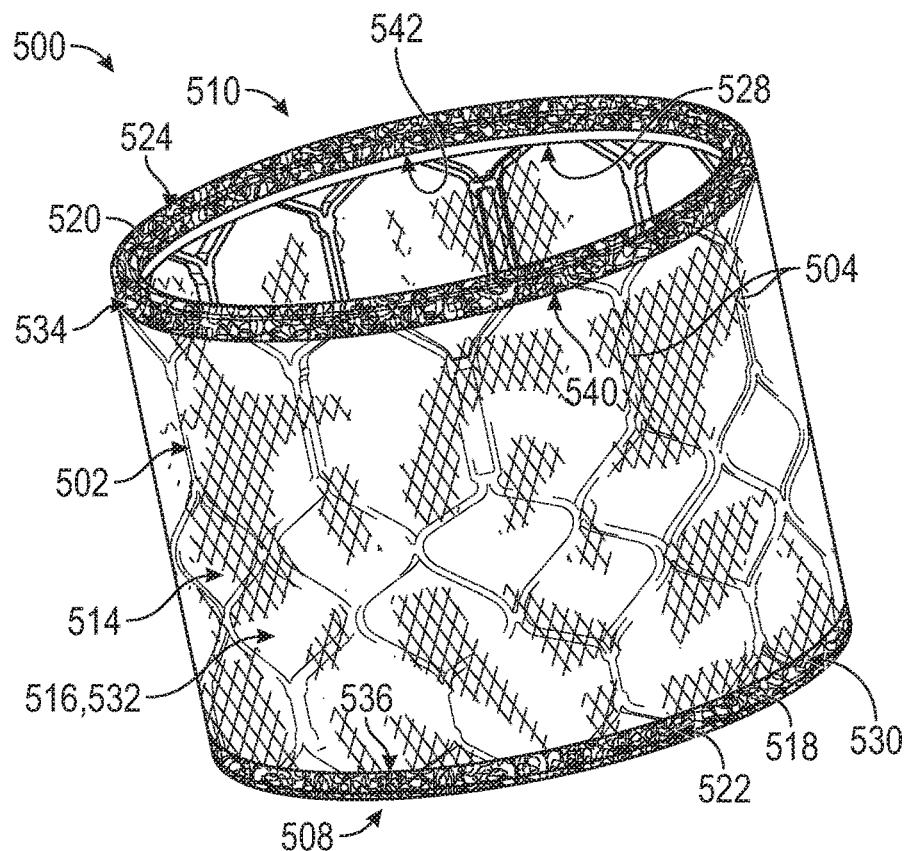
FIG. 27 is a perspective view of a frame for a prosthetic heart valve including an example of a covering.
Figure 28:
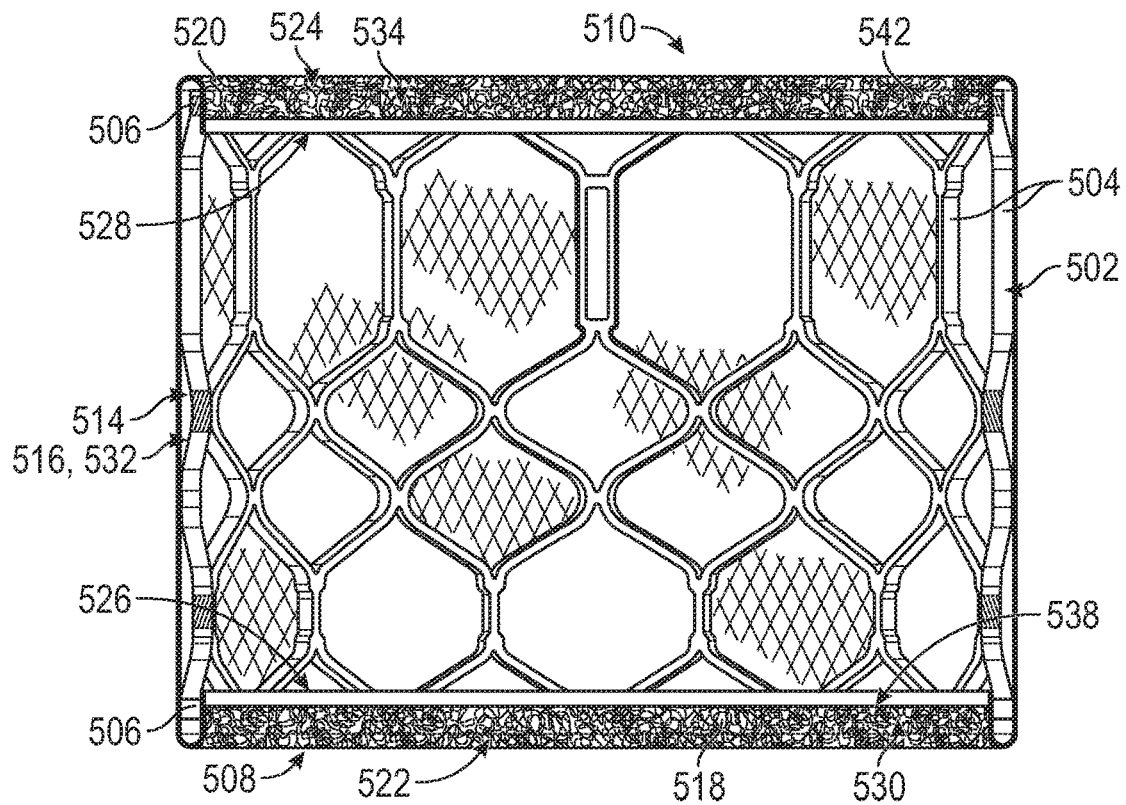
FIG. 28 is a cross-sectional side elevation view of the frame and covering of FIG. 27.

FIGS. 27 and 28 illustrates an example of a prosthetic heart valve 500 including a frame 502 formed by a plurality of strut members 504 defining apices 506 (FIG. 28), similar to the frame 102 described above and in U.S. Pat. No. 9,393,110. The prosthetic valve 500 can have an inflow end 508 and an outflow end 510, and can include a leaflet structure (not shown) situated at least partially within the frame.

The prosthetic valve can include an outer covering 514 situated about the frame 502. The covering or outer covering 514 can include a main cushioning layer 516 (also referred to as a main layer) having a cylindrical shape, and made from a woven, knitted, or braided fabric (e.g., a PET fabric, an ultra-high molecular weight polyethylene (UHMWPE) fabric, a PTFE fabric, etc.). In some embodiments, the fabric of the main cushioning layer 516 can include a plush pile. In some embodiments, the fabric of the main cushioning layer 516 can comprise texturized strands (e.g., texturized yarns, etc.) in which the constituent fibers of the strands/yarns have been bulked by, for example, being twisted, heat set, and untwisted such that the fibers retain their deformed, twisted shape and create a voluminous fabric. The volume contributed by the texturized strands/yarns can improve the cushioning properties of the covering, as well as increase friction between the fabric and the surrounding anatomy and/or an anchoring device into which the valve is deployed. The layer 516 alone or together with protective portions 518, 520 and/or layers 530, 534 can form a sealing member or cover member that can be placed around the frame to form the covering 514.

The outer covering 514 can include an inflow protective portion 518 extending circumferentially around the inflow end 508 of the frame, and an outflow protective portion 520 extending circumferentially around the outflow end 510 of the frame. In certain embodiments, the inflow and outflow protective portions 518 and 520 can be formed on the fabric of the main cushioning layer 516 such that the outer covering 514 is a one-piece, unitary construction, as described further below.

Referring to FIG. 28, the main cushioning layer 516 can include a first circumferential edge portion 522 (also referred to as an inflow edge portion) located adjacent the inflow end 508 of the valve, which can form a part of the inflow protective portion 518. The cushioning layer 516 can further include a second circumferential edge portion 524 (also referred to as an outflow edge portion) located adjacent the outflow end 510 of the valve, and which can form a part of the outflow protective portion 520. Referring still to FIG. 28, the first circumferential edge portion 522 can comprise an edge 526, and the second circumferential edge portion 524 can comprise an edge 528. The first circumferential edge portion 522 can be folded or wrapped over the apices 506 of the strut members 504 such that the edge 526 is disposed on the inside of the frame 502. The second circumferential edge portion 524 can be folded around the apices 506 at the outflow end 510 of the frame in a similar fashion such that the edge 528 is also disposed on the inside of the frame opposite the edge 522.

In the illustrated configuration, the inflow protective portion 518 can include a second or outer layer configured as a lubricious layer 530 of material disposed on an outer surface 532 of the main cushioning layer 516. The outflow protective portion 520 can also include a second or outer lubricious layer 534 of material disposed on the outer surface 532 of the main cushioning layer 516. In some embodiments, the layers 530 and 534 can be smooth, low-thickness coatings comprising a low-friction or lubricious material. For example, in certain configurations one or both of the layers 530, 534 can comprise PTFE or ePTFE.

In the illustrated configuration, the lubricious layer 530 can have a first circumferential edge 536 (FIG. 27) and a second circumferential edge 538 (FIG. 28). The lubricious layer 530 can extend from the outer surface 532 of the main cushioning layer 516 and over the apices 506 such that the first circumferential edge 536 is disposed on the outside of the frame and the second circumferential edge 538 is disposed on the inside of the frame. The lubricious layer 534 can be configured similarly, such that a first circumferential edge 540 (FIG. 27) is disposed outside the frame, the layer 534 extends over the apices 506 of the outflow end 510 of the frame, and a second circumferential edge 542 (FIG. 28) is disposed inside the frame. Once implanted in a native heart valve, the protection portions 518 and 520 can prevent direct contact between the apices 506 and the surrounding anatomy. The lubricious material of the layers 530 and 534 can also reduce friction with tissue of the native valve (e.g., chordae) in contact with the inflow and outflow ends of the prosthetic valve, thereby preventing damage to the tissue. In some embodiments, the entire outer surface 532 of the main cushioning layer 516, or a portion thereof, is covered with a lubricious coating such as ePTFE in addition to the inflow and outflow protective portions 518 and 520 such that the lubricious coating extends axially from the inflow end to the outflow end of the covering. In some embodiments, the cushioning layer 516 is formed from woven, knitted, braided, or electrospun fibers of lubricious material, such as PTFE, ePTFE, etc., and can form the inflow and outflow protective portions.

Figure 29:
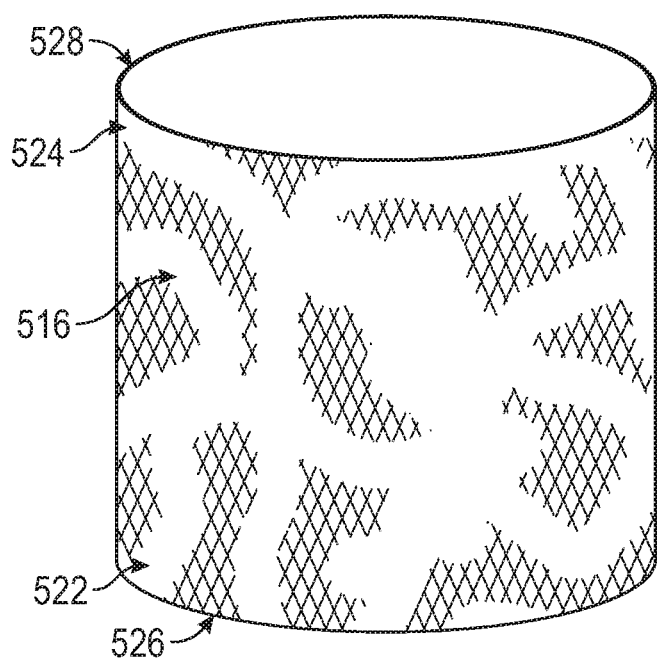
Figure 30:
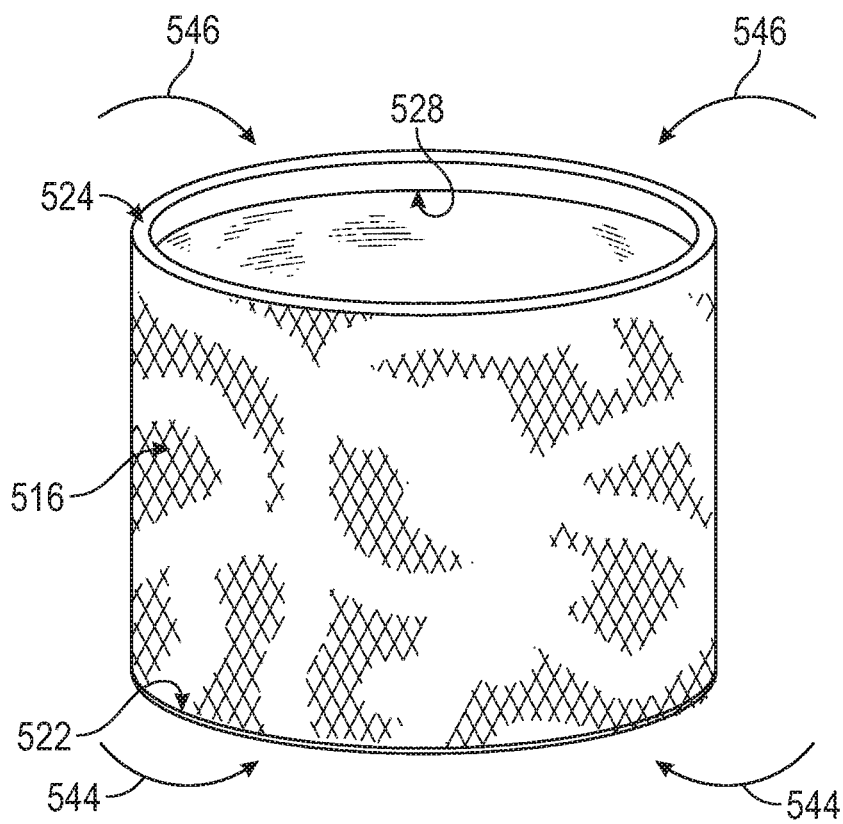

FIGS. 29-31B illustrate a representative method of making the covering 514. FIG. 29 illustrates the main cushioning layer 516 formed into a cylindrical, tubular body. Referring to FIG. 30, the first circumferential edge portion 522 of the cushioning layer 516 can then be folded over (e.g., inward toward the interior surface of the tubular body) in the direction of arrows 544 such that the lower edge 526 is inside the tubular body and disposed against the interior surface of the tubular body. The edge portion 524 can be folded in a similar manner as indicated by arrows 546 such that the top edge 528 is inside the tubular body and disposed against the interior surface.

Figure 31A:
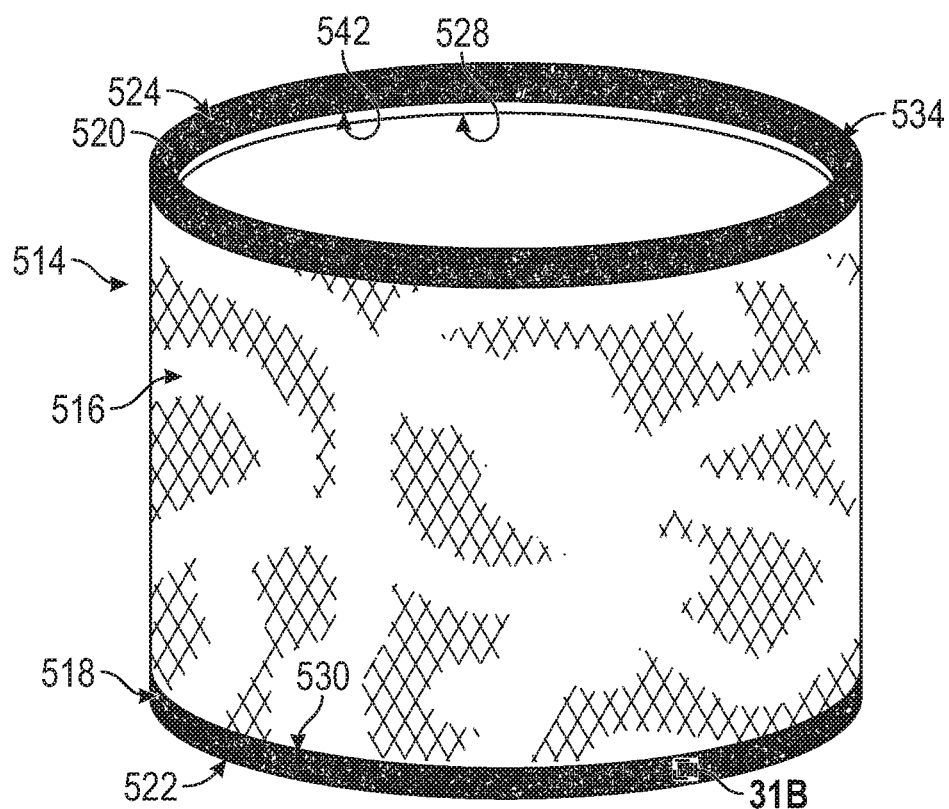
Figure 31B:
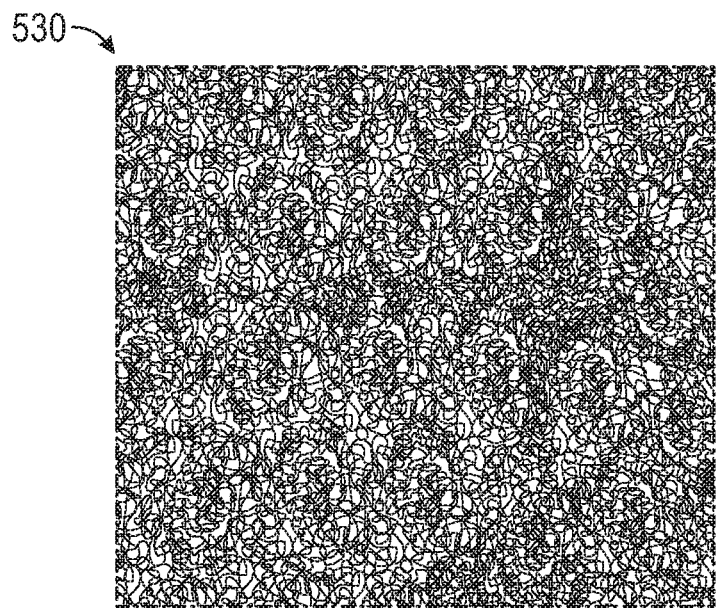
FIG. 31B is a detail view of the electrospun layer of the inflow end portion of the covering of FIG. 31A.

Referring to FIGS. 31A and 31B, the lubricious layers 530, 534 can then be applied to the main layer 516 to form the inflow and outflow protection portions 518 and 520. In certain embodiments, the lubricious layers 530, 534 can be formed by electrospinning a low-friction material (e.g., PTFE, ePTFE, etc.) onto the first and second circumferential edge portions 522 and 524. In certain embodiments, forming the layers 530, and 534 by electrospinning can provide a smooth, uniform surface, and keep the thickness of the layers within strictly prescribed specifications.

For example, the layers 530 and 534 can be made relatively thin, which can reduce the overall crimp profile of the valve. In certain embodiments, a thickness of the layers 530 and 534 can be from about 10 μm to about 500 μm, about 100 μm to about 500 μm, about 200 μm to about 300 μm, about 200 μm, or about 300 μm. They layers 530 and 534 can be made and/or modified in a variety of ways. In some embodiments, the layer 530 and/or 534 is made by dip-coating, spray-coating, or any other suitable method for applying a thin layer of lubricious material to the main cushioning layer 516. The finished covering or outer covering 514 can then be situated about and secured to the frame 502 using attachment means, for example, sutures, adhesive, ultrasonic welding, or any other suitable attachment method or means. In some embodiments, the main cushioning layer 516 is situated about the frame 502 before the edges are folded, and/or before the lubricious layers 530 and 534 are applied. In some embodiments, one or both of the lubricious layers 530 and/or 534 can be omitted from the first and second circumferential edge portions 522 and 524. In some embodiments, one or both of the first and second circumferential edge portions 522, 524 need not be folded inside the frame, but can extend to the respective inflow or outflow end of the frame, or beyond the ends of the frame on the exterior of the frame, as desired.

In addition to covering the frame 502 and the apices 506, the outer covering 514 can provide a number of other significant advantages. For example, the covering 514 can be relatively thin, allowing the prosthetic valve to achieve a low crimp profile (e.g., 23 Fr or below). The one-piece, unitary construction of the outer covering 514 and the protective portions 518 and 520 can also significantly reduce the time required to produce the covering and secure it to the frame, and can increase production yield.

In some embodiments, one or both of the inflow and outflow protection portions can be configured as separate coverings or covers that are spaced apart from the main layer or main cushioning layer, and may or may not be coupled to the main layer or main cushioning layer. For example, FIGS. 32-36 illustrate an example of a prosthetic heart valve 600 including a frame 602 formed by a plurality of strut members 604 defining apices 606, similar to the frame 102 described above and in U.S. Pat. No. 9,393,110. The prosthetic valve 600 can have an inflow end 608 and an outflow end 610, and can include a plurality of leaflets 612 situated at least partially within the frame.

Figure 34:
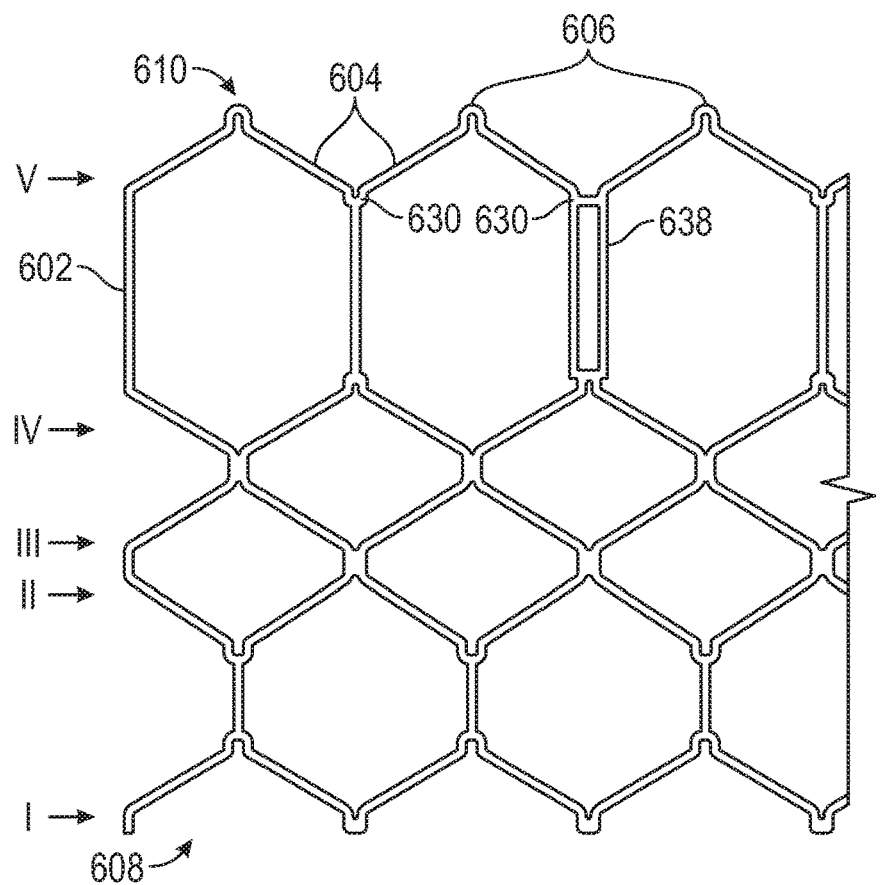
FIG. 34 is a plan view of a portion of the frame of the prosthetic valve of FIG. 32 in a laid-flat configuration.

FIG. 34 illustrates a portion of the frame 602 in a laid-flat configuration for purposes of illustration. The strut members 604 can be arranged end-to-end to form a plurality of rows or rungs of strut members that extend circumferentially around the frame 602. For example, with reference to FIG. 34, the frame 602 can comprise a first or lower row I of angled strut members forming the inflow end 608 of the frame; a second row II of strut members above the first row; a third row III of strut members above the second row; a fourth row IV of strut members above the third row, and a fifth row V of strut members above the fourth row and forming the outflow end 610 of the frame. At the outflow end 610 of the frame, the strut members 604 of the fifth row V can be arranged at alternating angles in a zig-zag pattern. The strut members 604 of the fifth row V can be joined together at their distal ends (relative to the direction of implantation, for example, in the mitral valve) to form the apices 606, and joined together at their proximal ends at junctions 630, which may form part of the commissure windows 638. Additional structure and characteristics of the rows I-V of strut members 604 are described in greater detail in U.S. Pat. No. 9,393,110, incorporated by reference above.

Returning to FIGS. 32 and 33, the prosthetic valve can include a first covering or first layer 614 (also referred to as a main covering or main layer) situated about the frame 602. The valve can also include an outflow protective portion configured as a second covering or cover 616 disposed about the strut members 604 and the apices 606 of the fifth row V of strut members at the outflow end 610 of the frame. The first covering or layer 614 can comprise a woven or knitted fabric made from, for example, PET, UHMWPE, PTFE, etc. Referring to FIG. 33, the first covering or layer 614 can include an inflow end portion 618 located at the inflow end 608 of the valve, and an outflow end portion 620 located at the outflow end 610 of the valve. In the illustrated embodiment, the outflow end portion 620 of the first covering or layer 614 can be offset toward the inflow end of the frame (e.g., in the upstream direction) from the fifth row V of strut members 604. Stated differently, the strut members 604 of the fifth row V can extend beyond an uppermost circumferential edge 622 of the first covering or layer 614 (e.g., distally beyond the edge 622 when the prosthetic valve is implanted in the native valve). A lowermost circumferential edge 624 of the main covering or layer 614 can be disposed adjacent the first row I of strut members 604 at the inflow end 608 of the valve. In some embodiments, the first covering or layer 614 can extend over and cover the apices 606 at the inflow end 608 of the frame.

Figure 35:
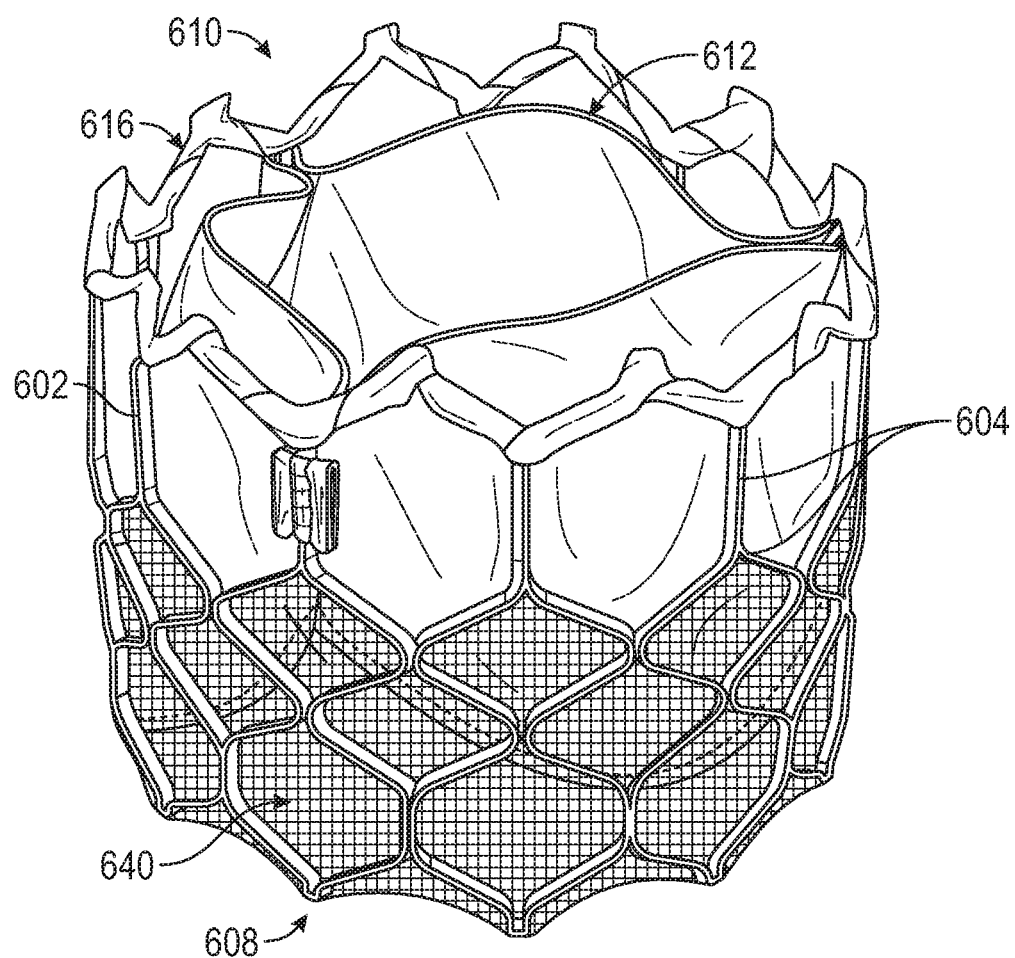
FIG. 35 is a perspective view of the prosthetic heart valve of FIG. 32 without the main outer covering.
Figure 36:
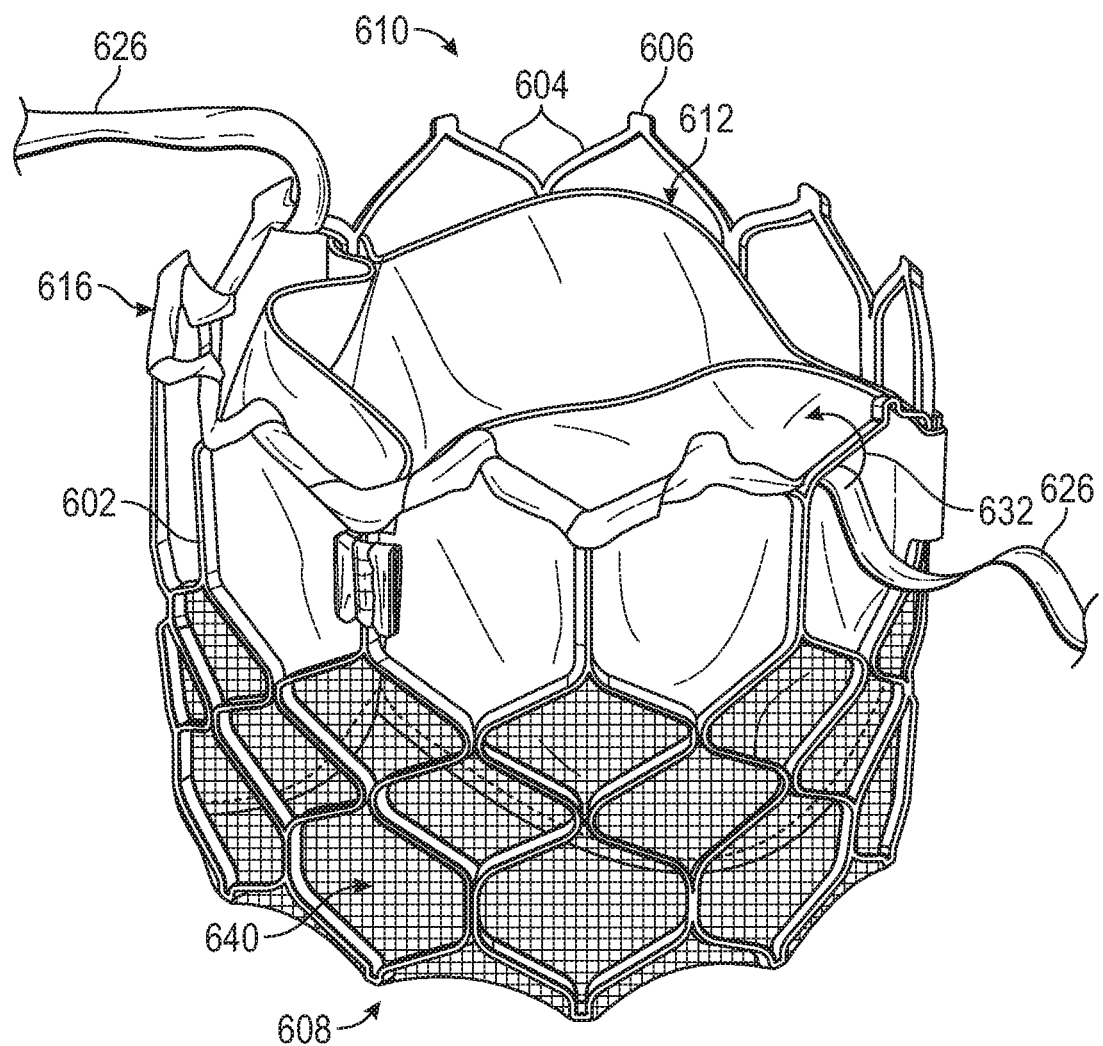
FIG. 36 is a perspective view of the prosthetic heart valve of FIG. 32 illustrating how the second covering is wrapped around the apices of the frame.

FIG. 35 illustrates the frame 602 including the second covering or cover 616 and an inner skirt 640, and without the first covering or layer 614 for purposes of illustration. In certain embodiments, the second covering or cover 616 can be configured as a wrapping that extends around the circumference of the frame 602 and surrounds the fifth row V of strut members 604. For example, with reference to FIG. 36, the covering or cover 616 can be configured as one or more straps or strips 626 of material that are helically wrapped around the struts 604 and the apices 606 of the fifth row V of strut members at the outflow end 610 of the frame in the direction such as indicated by arrow 632. In certain configurations, second covering or cover 616 is made of a lubricious or low-friction polymeric material, such as PTFE, ePTFE, UHMWPE, polyurethane, etc. In this manner, the second covering or cover 616 can reduce friction between the second covering or cover and native tissue that is in contact with the outflow end 610 of the valve. The covering or cover 616 can also prevent injury to native tissue by preventing it from directly contacting the apices 606.

In some embodiments, the strip 626 can be relatively thick to improve the cushioning characteristics of the second covering or cover 616. For example, in some embodiments, the strip 626 can be a PTFE strip having a thickness of from about 0.1 mm to about 0.5 mm, and a width of from about 3 mm to about 10 mm. In a representative embodiment, the strip 626 can have a thickness of about 0.25 mm, and a width of about 6 mm. The second covering or cover 616 can also include one or multiple layers. For example, the second covering or cover 616 can include a single layer (e.g., a single strip 626) wrapped around a row of struts of the frame. The second covering or cover may also include two layers, three layers, or more of strips wrapped around a row of struts of the frame. In some embodiments, the second covering or cover 616 can comprise multiple layers made of different materials. In certain configurations, the second covering or cover 616 can also be porous, and can have a pore size and pore density configured to promote tissue ingrowth into the material of the second covering/cover.

In some embodiments, the first covering or layer 614 and/or the second covering or cover 616 can be secured to the frame by attachment means, for example, suturing, adhesive, etc. In some embodiments, the first and second coverings 614, 616 can also be secured to each other with attachment means. For example, with reference to FIGS. 32 and 33, the first covering or layer 614 can include one or more sutures 628 extending circumferentially around the outflow end portion 620 of the first covering in, for example, a running stitch. At or near the junctions 630 (FIG. 34) of the fifth row V of strut members 604, the suture 628 can extend out of the stitch line (e.g., from the radially outward surface of the covering 614), and loop over the second covering/cover 616. The suture 628 can then reenter the covering 614 (e.g., on the radially inward surface of the covering/layer 614) and resume the running stitch. In the illustrated embodiment, the suture 628 can loop over the second covering/cover 616 at the junctions 630. The loops of suture 628 thereby rest in "valleys" between the apices 606, and can serve to hold the second covering/cover 616 in place on the strut members 602. The suture 628 can also hold the first covering 614 in place while the valve is being crimped.

Figure 32:
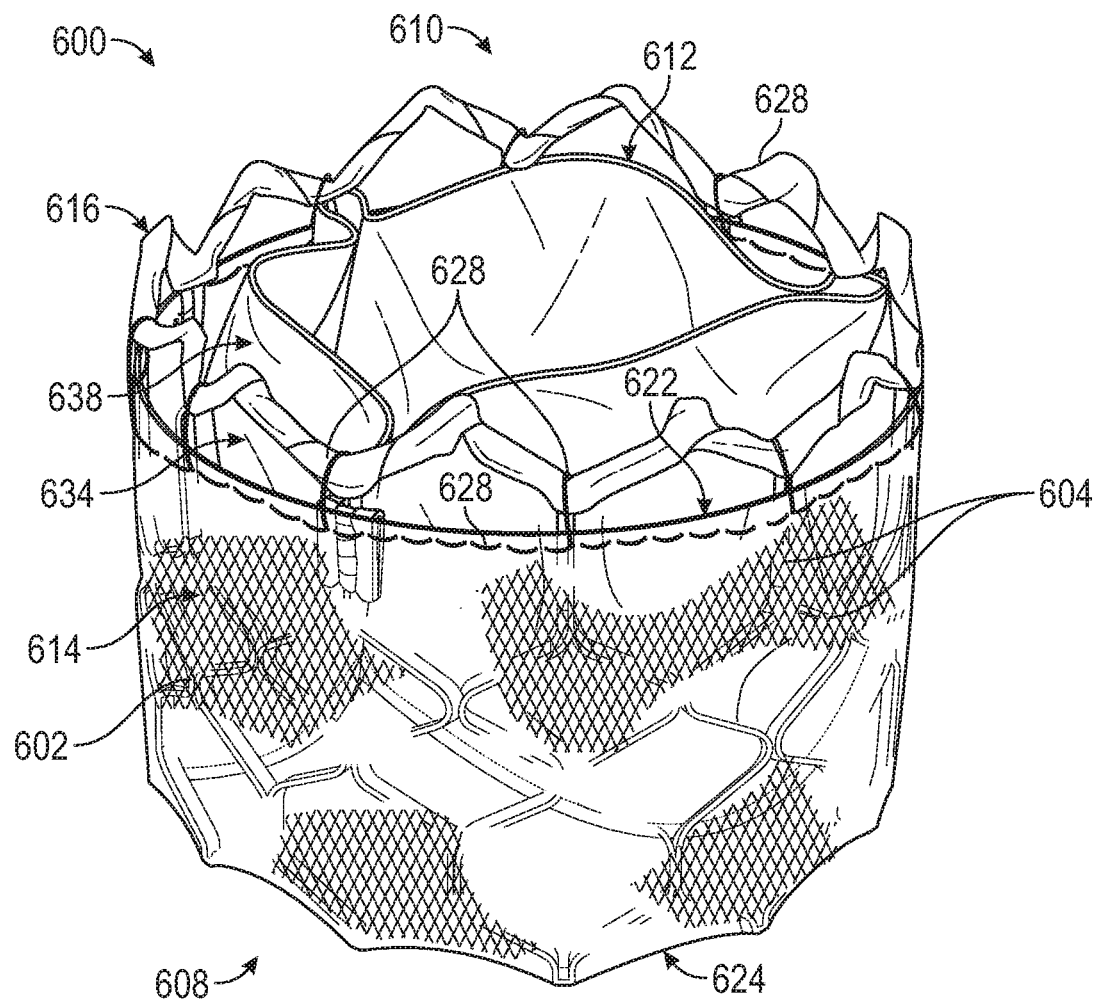
FIG. 32 is a perspective view of a prosthetic heart valve including a main covering and a second covering extending over the apices of the frame.
Figure 33:
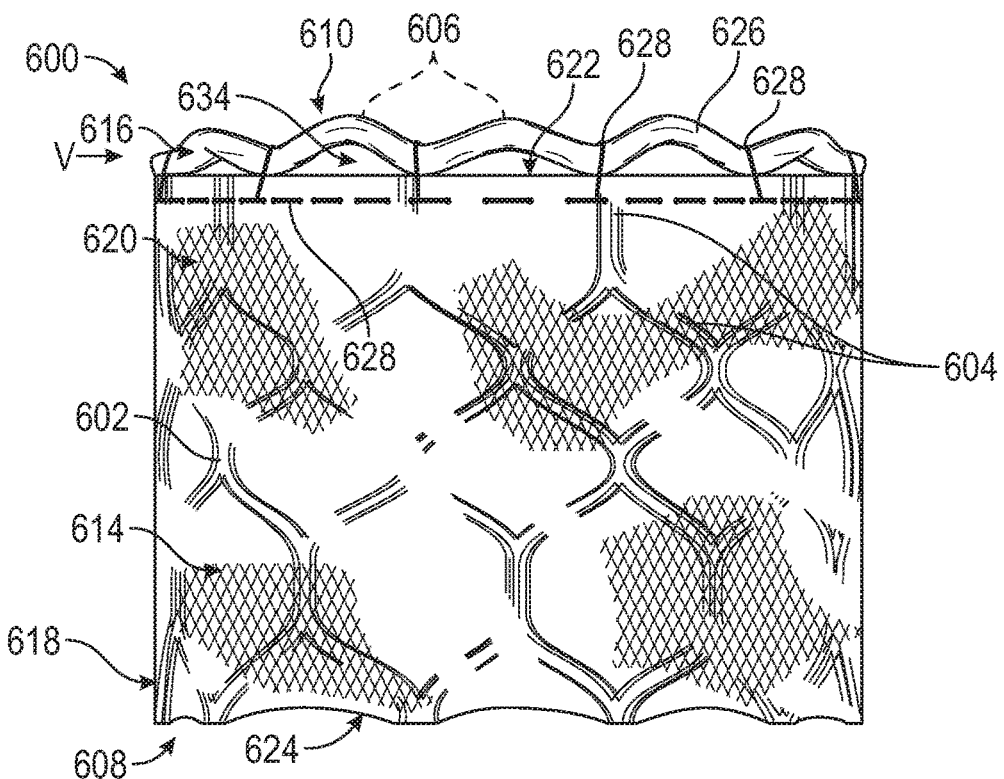
FIG. 33 is a side elevation view of the prosthetic heart valve of FIG. 32.

Still referring to FIGS. 32 and 33, the circumferential edge 622 of the first covering/layer 614 can be relatively straight, while the second covering/cover 616 can conform to the angled or zig-zag pattern of the fifth row V of strut members 604. In this manner, the first and second coverings 614 and 616 can define a plurality of gaps or openings 634 through the frame 602 between the first and second coverings. In the illustrated embodiment, the openings 634 have a triangular shape, with the base of the triangle being defined by the edge 622 of the first covering 614, and the sides being defined by the second covering/cover 616. The openings 634 can be configured such that after the valve 600 is implanted, blood can flow in and/or out of the frame 602 through the openings. In this manner, the space between the interior of the frame 602 and the ventricular surfaces 638 of the leaflets 612 can be flushed or washed by blood flowing into and out of the openings 634 during operation of the prosthetic valve. This may potentially reduce the risk of thrombus formation and left ventricular outflow tract obstruction.

Figure 37:
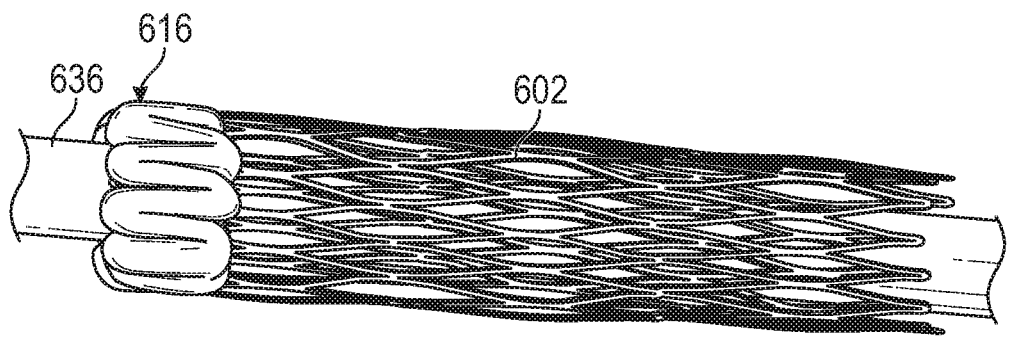
FIG. 37 is a perspective view illustrating the frame of the prosthetic valve of FIG. 32 including the second covering crimped onto a shaft of a delivery apparatus.

FIG. 37 illustrates the frame 602 including the second covering/cover 616 in a radially collapsed or crimped delivery configuration on a shaft 636 of a delivery apparatus. As shown in FIG. 37, the second covering/cover 616 can conform to the closely-packed, serpentine shape of the strut members 604 as they move to the radially collapsed configuration. In certain configurations, the second covering/cover 616 can closely mimic the shape and direction of the strut members 604 without bulging, pleating, creasing, or bunching to maintain a low crimp profile. In some embodiments, the inflow end of the frame includes a separate covering similar to the covering/cover 616.

FIGS. 38A, 38B, 39A, and 39B illustrate the prosthetic valve 400 of FIGS. 19-26 including an example covering or outer covering 700. The outer covering 700 can include a main layer or main cushioning layer 702 having a plush exterior surface 704. The covering 700 can also include an inflow protection portion 706 extending circumferentially around the inflow end 406 of the valve, and an outflow protection portion 708 extending circumferentially around the outflow end 408 of the valve. As in the embodiment of FIGS. 19-26, the inflow and outflow protection portions 706, 708 can be formed with separate pieces of material that are folded around the circumferential ends of the main layer 702 such that the cushioning portions encapsulate the apices 420 of the strut members at the inflow and outflow ends of the valve. For example, the inflow and outflow protection portions 706, 708 can be constructed from strips of material (e.g., polymeric materials such as PTFE, ePTFE, etc., or natural tissues such as pericardium, etc.) folded such that one circumferential edge of the strips is disposed against the interior of the frame 402 (or an inner skirt within the frame), and the other circumferential edge is disposed against the outer surface of the main layer 702. The outer covering 700 can be secured to the frame 402 using attachment means, for example, sutures, ultrasonic welding, or any other suitable attachment method or means. The layer 702 alone or together with protective portions 706, 708 can form a sealing member or cover member that can be placed around the frame to form the covering 700.

The main layer 702 of the outer covering 700 can comprise a woven or knitted fabric. The fabric of the main layer 702 can be resiliently stretchable between a first, natural, or relaxed configuration (FIGS. 38A and 38B), and a second, elongated, or tensioned configuration (FIGS. 39A and 39B). When disposed on the frame 402, the relaxed configuration can correspond to the radially expanded, functional configuration of the prosthetic valve, and the elongated configuration can correspond to the radially collapsed delivery configuration of the valve. Thus, with reference to FIG. 38A, the outer covering 700 can have a first length $L_1$ when the prosthetic valve is in the expanded configuration, and a second length $L_2$ (FIG. 39A) that is longer than $L_1$ when the valve is crimped to the delivery configuration, as described in greater detail below.

The fabric can comprise a plurality of circumferentially extending warp strands/yarns 712 and a plurality of axially extending weft strands/yarns 714. In some embodiments, the warp strands/yarns 712 can have a denier of from about 1 D to about 300 D, about 10 D to about 200 D, or about 10 D to about 100 D. In some embodiments, the warp strands/ yarns 712 can have a thickness $t_1$ (FIG. 40A) of from about 0.01 mm to about 0.5 mm, about 0.02 mm to about 0.3 mm, or about 0.03 mm to about 0.1 mm. In some embodiments, the warp strands/yarns 712 can have a thickness $t_1$ of about 0.03 mm, about 0.04 mm, about 0.05 mm, about 0.06 mm, about 0.07 mm, about 0.08 mm, about 0.09 mm, or about 0.1 mm. In a representative embodiment, the warp strands/yarns 712 can have a thickness of about 0.06 mm.

The weft strands/yarns 714 can be texturized strands/ yarns comprising a plurality of texturized filaments 716. For example, the filaments 716 of the weft strands/yarns 714 can be bulked, wherein, for example, the filaments 716 are twisted, heat set, and untwisted such that the filaments retain their deformed, twisted shape in the relaxed, non-stretched configuration. The filaments 716 can also be texturized by crimping, coiling, etc. When the weft strands/yarns 714 are in a relaxed, non-tensioned state, the filaments 716 can be loosely packed and can provide compressible volume or bulk to the fabric, as well as a plush surface. In some embodiments, the weft strands/yarns 714 can have a denier of from about 1 D to about 500 D, about 10 D to about 400 D, about 20 D to about 350 D, about 20 D to about 300 D, or about 40 D to about 200 D. In certain embodiments, the weft strands/yarns 714 can have a denier of about 150 D. In some embodiments, a filament count of the weft strands/ yarns 714 can be from 2 filaments per strand/yarn to 200 filaments per strand/yarn, 10 filaments per strand/yarn to 100 filaments per strand/yarn, 20 filaments per strand/yarn to 80 filaments per strand/yarn, or about 30 filaments per strand/yarn to 60 filaments per yarn. Additionally, although the axially-extending textured strands/yarns 714 are referred to as weft strands/yarns in the illustrated configuration, the fabric may also be manufactured such that the axially-extending textured strands/yarns are warp strands/yarns and the circumferentially-extending strands/yarns are weft strands/yarns.

Figure 40A:
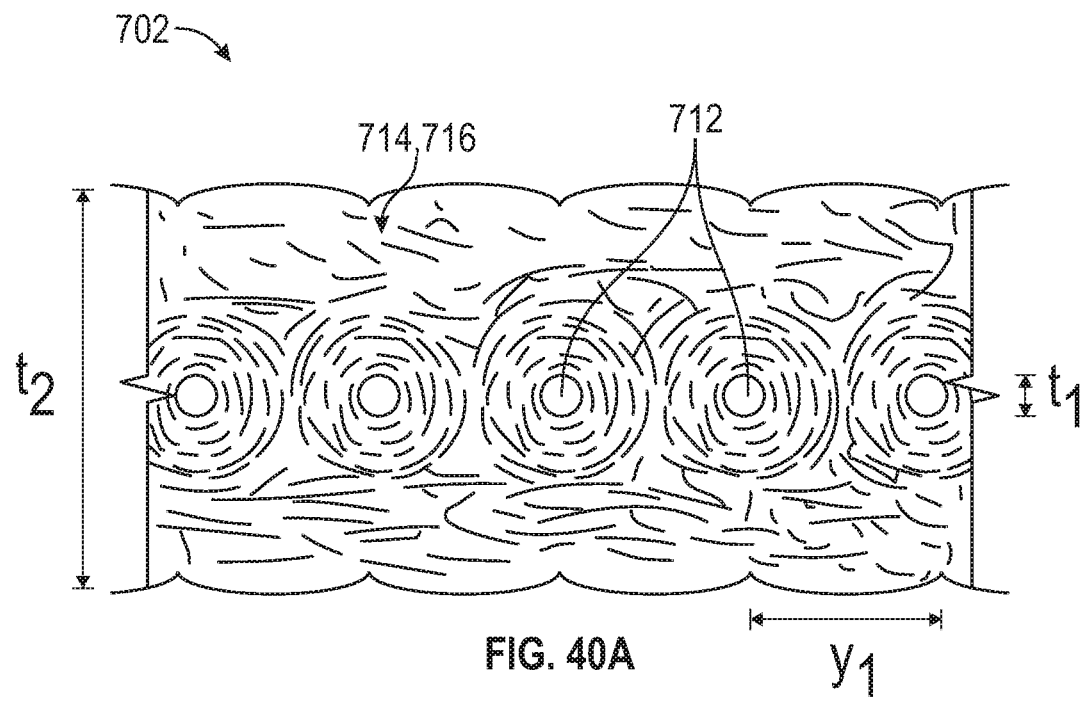
FIG. 40A is a cross-sectional side elevation view of the fabric of the outer covering of FIG. 38A in a relaxed state.
Figure 40B:
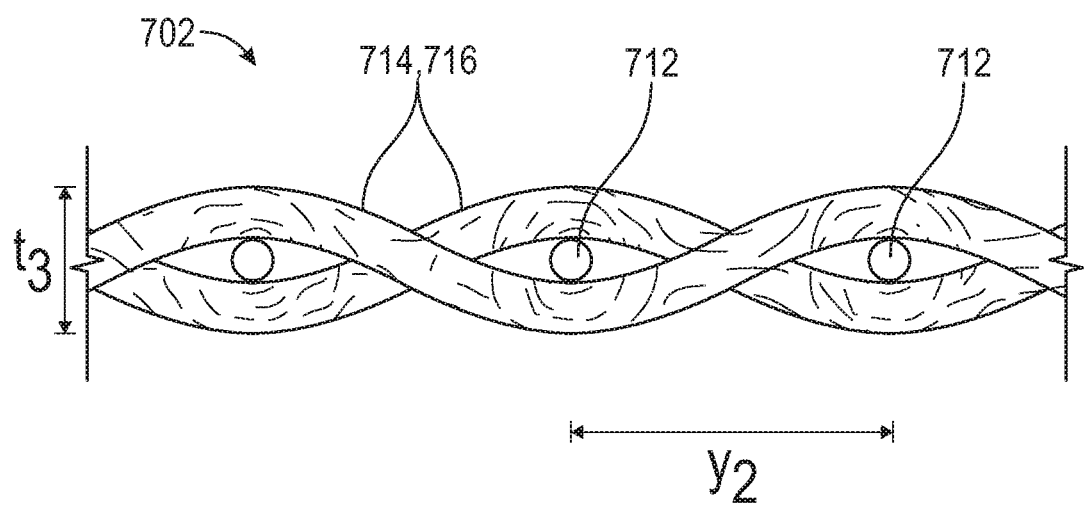
FIG. 40B is a cross-sectional side elevation view of the fabric of the outer covering of FIG. 38A in a tensioned state.

FIGS. 40A and 40B illustrate a cross-sectional view of the main layer 702 in which the weft strands/yarns 712 extend into the plane of the page. With reference to FIG. 40A, the fabric of the main layer 702 can have a thickness $t_2$ of from about 0.1 mm to about 10 mm, about 1 mm to about 8 mm, about 1 mm to about 5 mm, about 1 mm to about 3 mm, about 0.5 mm, about 1 mm, about 1.5 mm, about 2 mm, about 2.5 mm, or about 3 mm when in a relaxed state and secured to a frame. In some embodiments, the main layer 702 can have a thickness of about 0.1 mm, about 0.2 mm, about 0.3 mm, about 0.4 mm, or about 0.5 mm as measured in a relaxed state with a weighted drop gauge having a presser foot. In a representative example, the main layer 702 can have a thickness of about 1.5 mm when secured to a prosthetic valve frame in the relaxed state. This can allow the fabric of the main layer 702 to cushion the leaflets between the valve body and an anchor or ring into which the valve is implanted, as well as to occupy voids or space in the anatomy. The texturized, loosely packed filaments 716 of the weft strands/yarns 714 in the relaxed state can also promote tissue growth into the main layer 702.

Figure 38A:
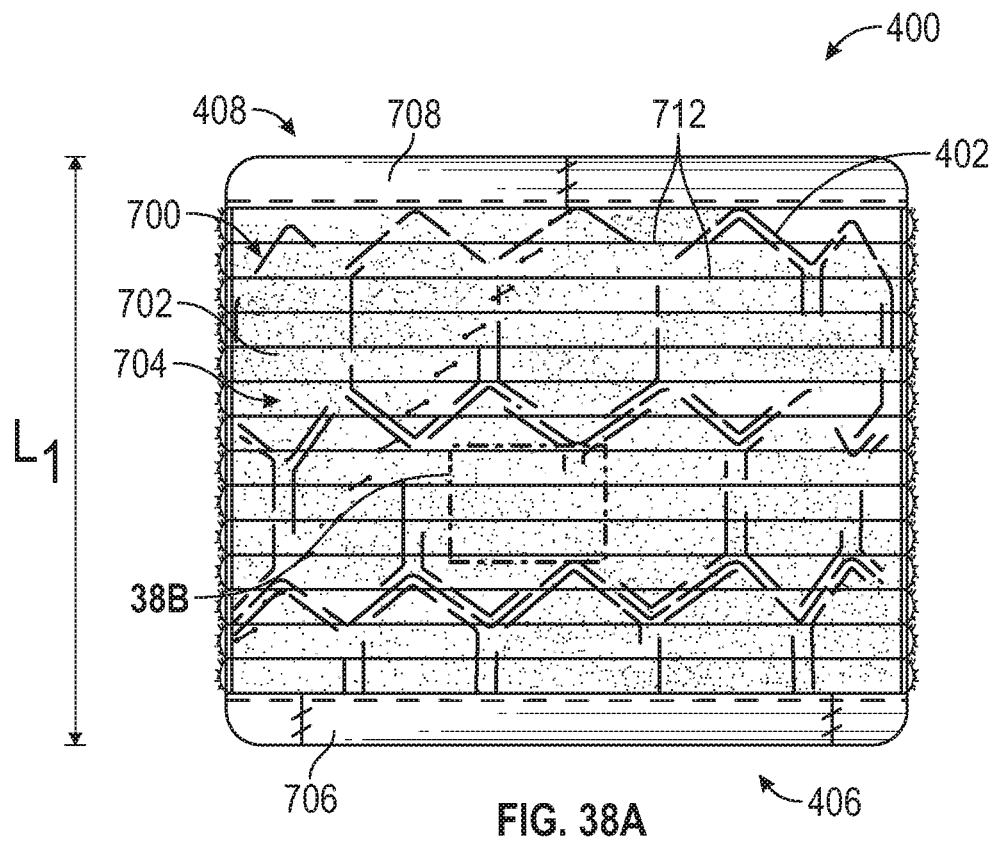
FIG. 38A is a side elevation view of the prosthetic valve of FIG. 19 including an example of an outer covering.
Figure 38B:
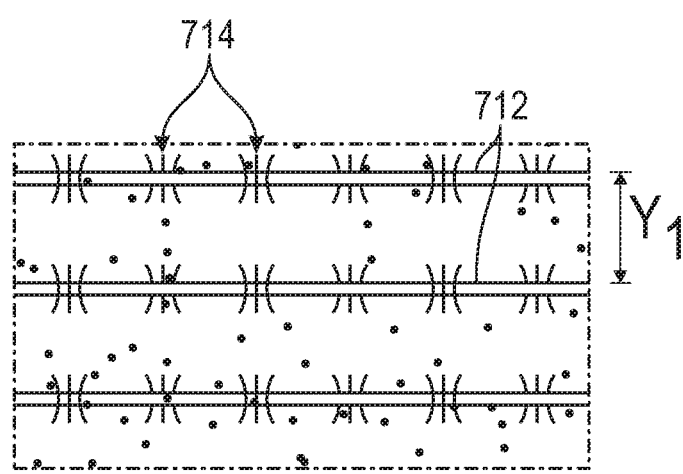
FIG. 38B is a detail view of the fabric of the outer covering of FIG. 38A.
Figure 39A:
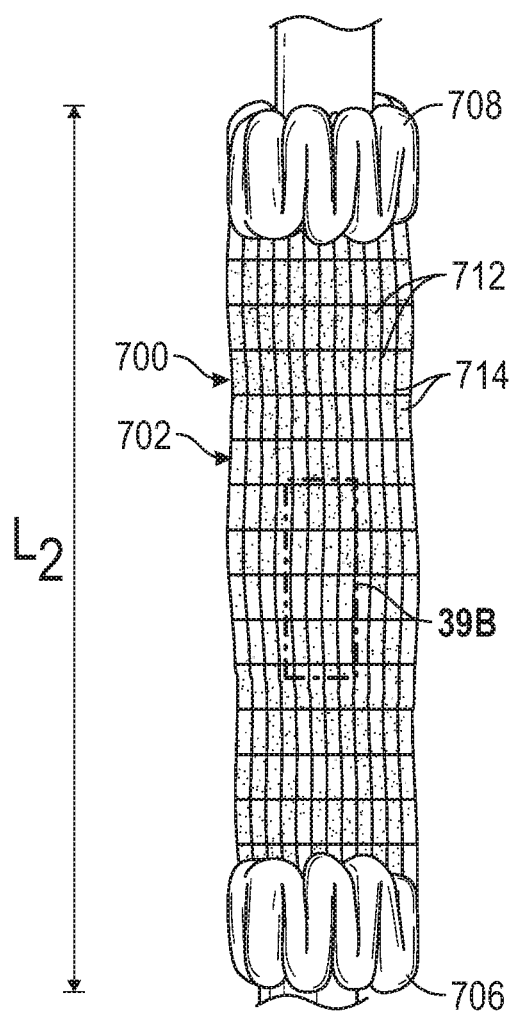
FIG. 39A is a plan view illustrating the prosthetic heart valve of FIG. 38A crimped onto a shaft of a delivery device.
Figure 39B:
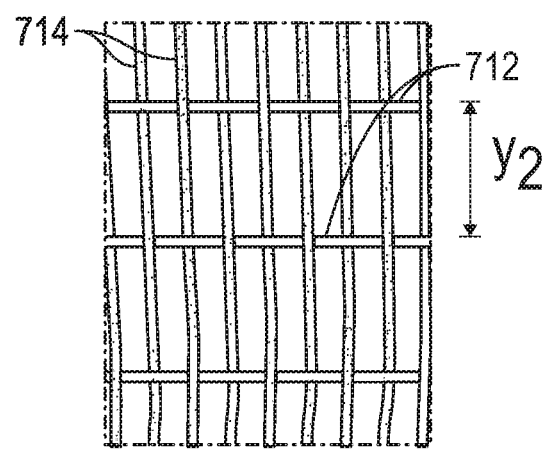
FIG. 39B is a detail view of the outer covering of the prosthetic heart valve in FIG. 39A.

When the fabric is in the relaxed state, the textured filaments 716 of the weft strands/yarns 714 can be widely dispersed such that individual weft strands/yarns are not readily discerned, as in FIGS. 38A and 38B. When tensioned, the filaments 716 of the weft strands/yarns 714 can be drawn together as the weft strands/yarns elongate and the kinks, twists, etc., of the filaments are pulled straight such that the fabric is stretched and the thickness decreases. In certain embodiments, when sufficient tension is applied to the fabric in the axial (e.g., weft) direction, such as when the prosthetic valve is crimped onto a delivery shaft, the textured fibers 716 can be pulled together such that individual weft strands/yarns 714 become discernable, as best shown in FIGS. 39B and 40B.

Thus, for example, when fully stretched, the main layer 702 can have a second thickness $t_3$, as shown in FIG. 40B that is less than the thickness $t_2$. In certain embodiments, the thickness of the tensioned weft strands/yarns 714 may be the same or nearly the same as the thickness $t_1$ of the warp strands/yarns 712. Thus, in certain examples, when stretched the fabric can have a thickness $t_3$ that is the same or nearly the same as three times the thickness $t_1$ of the warp strands/yarns 712 depending upon, for example, the amount of flattening of the weft strands/yarns 714. Accordingly, in the example above in which the warp strands/yarns 712 have a thickness of about 0.06 mm, the thickness of the main layer 702 can vary between about 0.2 mm and about 1.5 mm as the fabric stretches and relaxes. Stated differently, the thickness of the fabric can vary by 750% or more as the fabric stretches and relaxes.

Additionally, as shown in FIG. 40A, the warp strands/yarns 712 can be spaced apart from each other in the fabric by a distance $y_1$ when the outer covering is in a relaxed state. As shown in FIGS. 39B and 40B, when tension is applied to the fabric in the direction perpendicular to the warp strands/yarns 712 and parallel to the weft strands/yarns 714, the distance between the warp strands/yarns 712 can increase as the weft strands/yarns 714 lengthen. In the example illustrated in FIG. 40B, in which the fabric has been stretched such that the weft strands/yarns 714 have lengthened and narrowed to approximately the diameter of the warp strands/yarns 712, the distance between the warp strands/yarns 712 can increase to a new distance $y_2$ that is greater than the distance $y_1$.

In certain embodiments, the distance $y_1$ can be, for example, about 1 mm to about 10 mm, about 2 mm to about 8 mm, or about 3 mm to about 5 mm. In a representative example, the distance $y_1$ can be about 3 mm. In some embodiments, when the fabric is stretched as in FIGS. 39B and 40B, the distance $y_2$ can be about 6 mm to about 10 mm. Thus, in certain embodiments, the length of the outer covering 700 can vary by 100% or more between the relaxed length $L_1$ and the fully stretched length (e.g., $L_2$). The fabric's ability to lengthen in this manner can allow the prosthetic valve to be crimped to diameters of, for example, 23 Fr, without being limited by the outer covering's ability to stretch. Thus, the outer covering 700 can be soft and voluminous when the prosthetic valve is expanded to its functional size, and relatively thin when the prosthetic valve is crimped to minimize the overall crimp profile of the prosthetic valve.

Figure 41A:
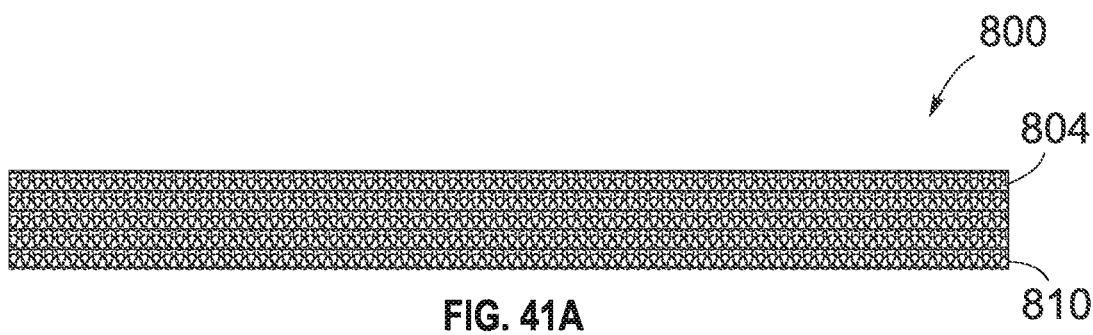
FIG. 41A is a plan view of an example of a fabric outer covering for a prosthetic valve in a laid-flat configuration and including an outer surface defined by a pile layer.
Figure 41B:
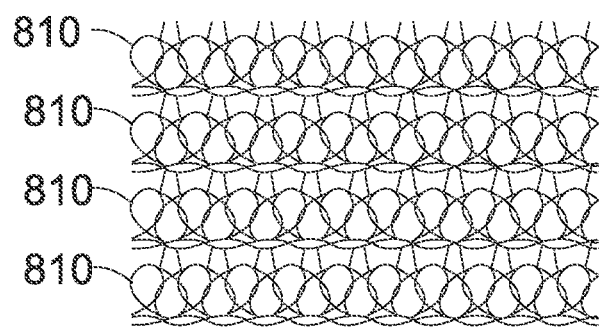
FIG. 41B is a magnified view of the outer covering of FIG. 41A.
Figure 42A:
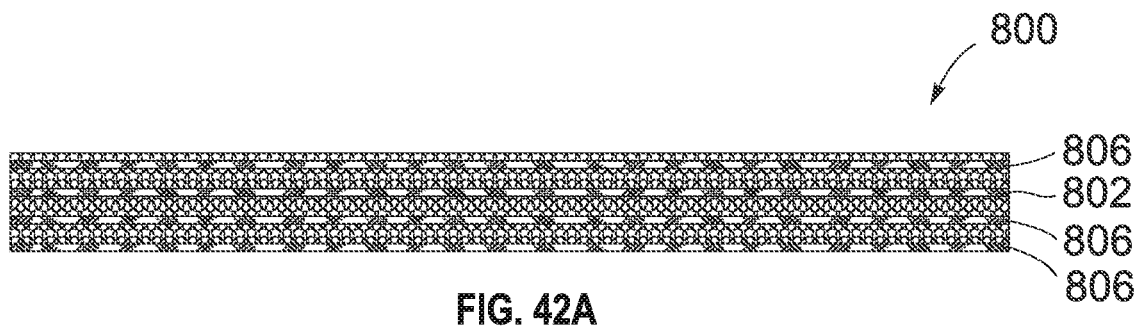
FIG. 42A is a plan view of a base layer of the outer covering of FIG. 41A.
Figure 42B:
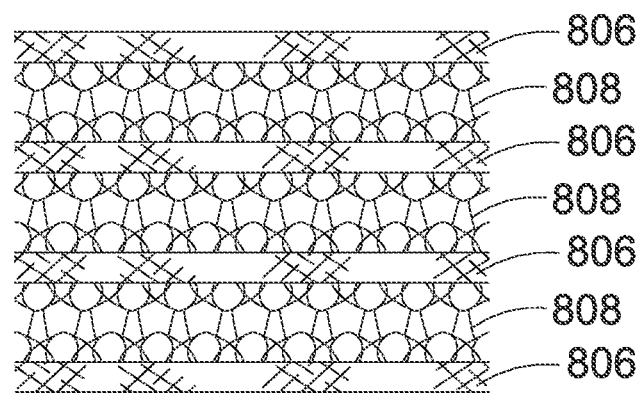
FIG. 42B is a magnified view of the base layer of FIG. 42A.

FIGS. 41A, 41B, 42A, and 42B show an example of a sealing member or cover member 800 for a prosthetic heart valve (e.g., such as the prosthetic heart valve 400). The sealing member 800 can be a dual-layer fabric comprising a base layer 802 and a pile layer 804. FIG. 41A shows the outer surface of the sealing member 800 defined by the pile layer 804. FIG. 42A shows the inner surface of the sealing member 800 defined by the base layer 802. The base layer 802 in the illustrated configuration comprises a mesh weave having circumferentially extending rows or stripes 806 of higher-density mesh portions interspersed with rows or stripes 808 of lower-density mesh portions. The sealing member/cover member 800 can be used to cover or form a covering on a stent frame (e.g. on some, a portion, or all of a stent frame).

In some embodiments, the strand/yarn count of strands/yarns extending in the circumferential direction (side-to-side or horizontally in FIGS. 42A and 42B) is greater in the higher-density rows 806 than in the lower-density rows 808. In some embodiments, the strand/yarn count of strands/yarns extending in the circumferential direction and the strand/yarn count of strands/yarns extending in the axial direction (vertically in FIGS. 42A and 42B) is greater in the higher-density rows 806 than in the lower-density rows 808.

The pile layer 804 can be formed from strands/yarns woven into the base layer 802. For example, the pile layer 804 can comprise a velour weave formed from strands/yarns incorporated in the base layer 802. Referring to FIG. 41B, the pile layer 804 can comprise circumferentially extending rows or stripes 810 of pile formed at axially-spaced locations along the height of the sealing member 800 such that there are axial extending gaps between adjacent rows 810. In this manner, the density of the pile layer varies along the height of the sealing member. In some embodiments, the pile layer 804 can be formed without gaps between adjacent rows of pile, but the pile layer can comprise circumferentially extending rows or stripes of higher-density pile interspersed with rows or stripes of lower-density pile.

In some embodiments, the base layer 802 can comprise a uniform mesh weave (the density of the weave pattern is uniform) and the pile layer 804 has a varying density.

In some embodiments, the density of the sealing member 800 can vary along the circumference of the sealing member. For example, the pile layer 804 can comprise a plurality of axially-extending, circumferentially-spaced, rows of pile yarns, or can comprise alternating axially-extending rows of higher-density pile interspersed with axially-extending rows of lower-density pile. Similarly, the base layer 802 can comprise a plurality axially-extending rows of higher-density mesh interspersed with rows of lower-density mesh.

In some embodiments, the sealing member 800 includes a base layer 802 and/or a pile layer 804 that varies in density along the circumference of the sealing member and along the height of the sealing member.

Varying the density of the pile layer 804 and/or the base layer 802 along the height and/or the circumference of the sealing member 800 is advantageous in that it reduces the bulkiness of the sealing member in the radially collapsed state and therefore reduces the overall crimp profile of the prosthetic heart valve.

In certain embodiments, the outer covering 800 can include inflow and/or outflow protective portions similar to the protective portions 416 and 418 above. However, in some embodiments, the outer covering 800 need not include protective portions and can extend between the top and bottom row of strut members of a frame, or between intermediate rows of strut members, depending upon the particular application.

Figure 43:
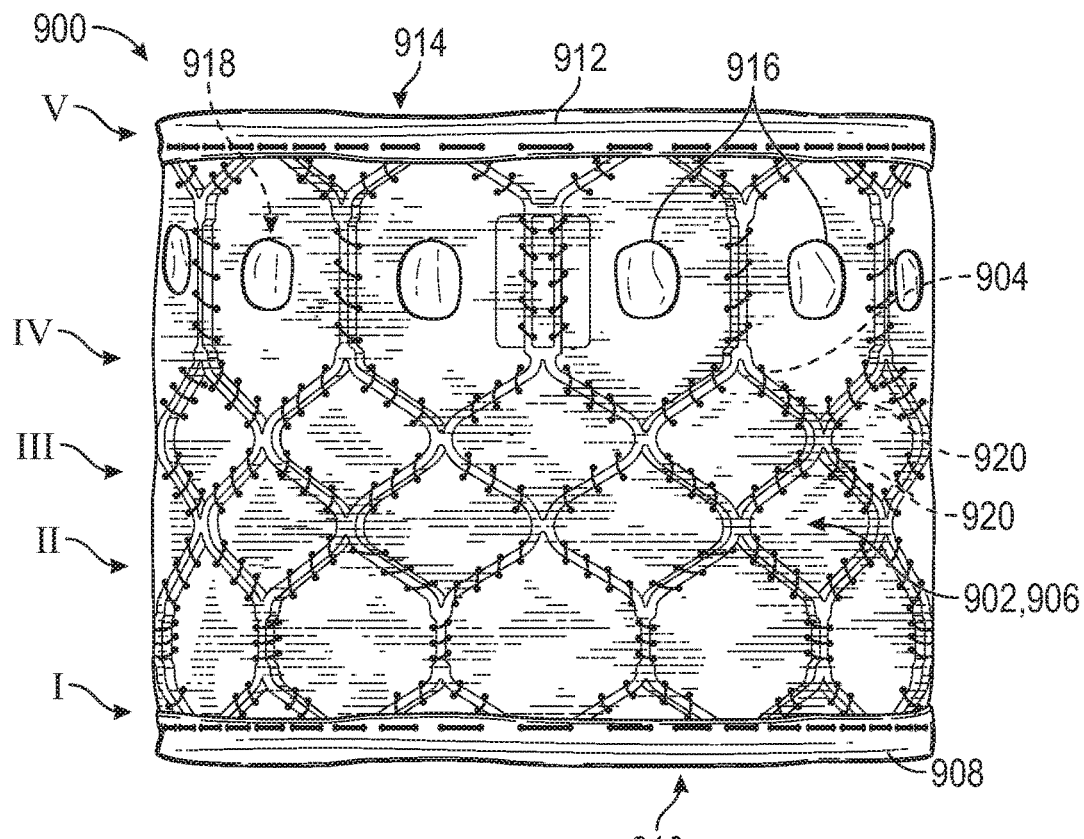
FIGS. 43-45 are a side elevational views of a prosthetic heart valve including various embodiments of an outer covering including openings.
Figure 44:
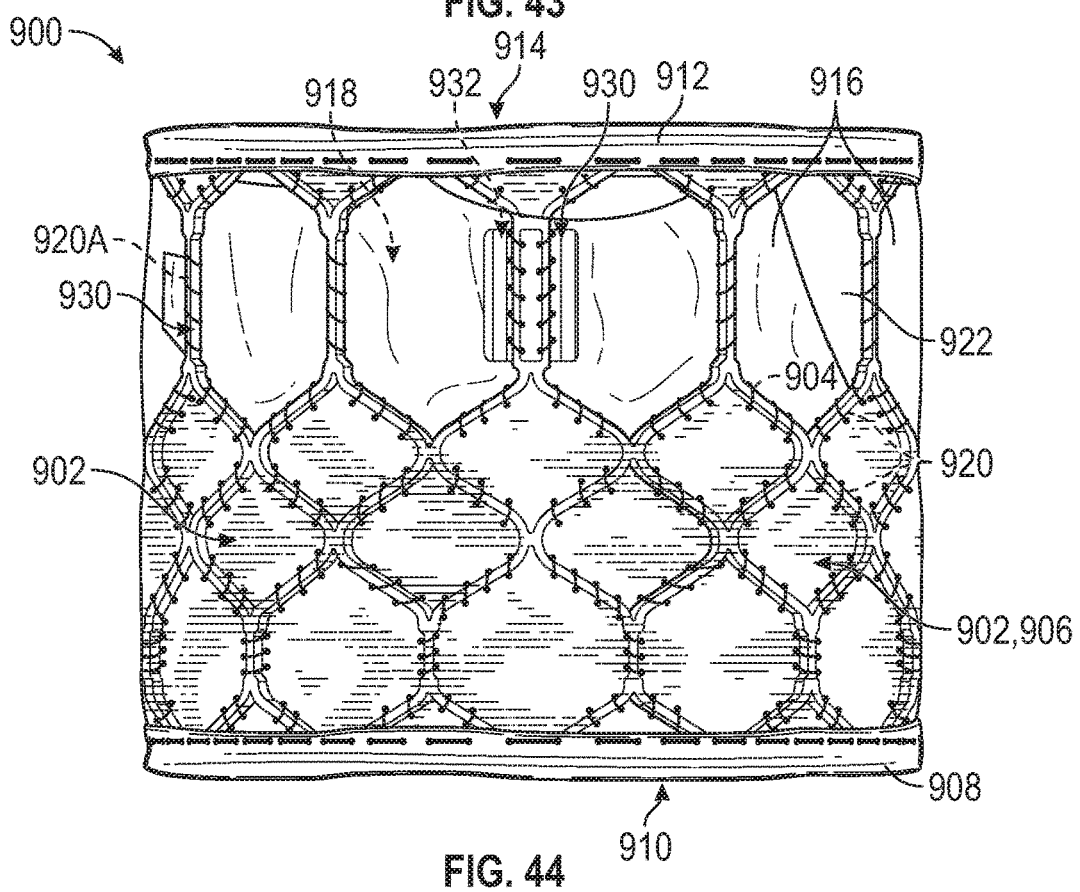

FIGS. 43 and 44 illustrate a prosthetic heart valve 900 including an example of a covering or outer covering 902 situated around a frame 904, and including a plurality of leaflets 922 (FIG. 44) situated at least partially within the frame 904. The frame 904 can include a plurality of struts 920, and can be configured as the frame of the Edwards Lifesciences SAPIEN® 3 prosthetic heart valve, similar to the frame 402 of FIG. 19. The outer covering 902 can include a main cushioning layer or sealing member/cover member 906 (also referred to as a main layer) having a cylindrical shape, and made from a woven, knitted, or braided fabric (e.g., a PET fabric, an ultra-high molecular weight polyethylene (UHMWPE) fabric, a PTFE fabric, etc.), a non-woven fabric such as felt, or an extruded polymer film (e.g., an ePTFE or UHMWPE membrane). The outer covering 902 can also include an inflow protection portion 908 extending circumferentially around the inflow end 910 of the frame, and an outflow protection portion 912 extending circumferentially around the outflow end 914 of the frame. In the embodiment of FIGS. 43 and 44, the inflow and outflow protection portions 908 and 912 are configured as separate pieces of material folded around the circumferential ends of the main layer 906 similar to the embodiment of FIGS. 19-26, but may also comprise lubricous layers formed on the circumferential edge portions of the main layer 906 by other means, such as by electrospinning, as in the embodiment of FIG. 31A.

Referring to FIG. 43, the layer 906 of the outer covering 902 can comprise a woven or knitted fabric. The layer 906 can comprise a plurality of holes or openings 916 circumferentially spaced apart from each other around the frame 904, and aligned with or overlying openings defined between the frame struts. For example, in the illustrated embodiment the openings 916 can be located at the level of openings 918 defined between the frame struts 920 of the fourth row IV and the fifth row V of struts (see also FIG. 34) near the outflow end 914 of the frame. The openings 916 can be relatively small, as in the embodiment of FIG. 43, or larger, depending upon the particular characteristics desired.

For example, with reference to FIG. 44, in certain embodiments the openings 916 can be the same size and shape, or nearly the same size and shape, as the frame openings 918. Thus, in the embodiment of FIG. 44, the openings 916 can comprise the polygonal (e.g., hexagonal) shape of the frame openings 918, and can be of the same size or area as the frame openings 918. In this configuration, relatively narrow strips 930 of the main layer 906 can extend along axially-oriented struts 920A between the fourth row IV and the fifth row V of struts, and over the commissure windows and the commissure tabs 932 of the leaflets 922. Thus, in certain configurations, the openings 916 of the covering 902 can be aligned with the frame openings 918, and yet the covering 902 can cover the entire outer surface of the frame 904. In other words, the covering 902 can cover the outer surfaces of all of the strut members 920.

The openings 916 can be formed in a variety of ways. In certain embodiments, the openings 916 are cut (e.g., using a laser) from the fabric of the main layer 906 before the covering is assembled on the frame 904. In some embodiments, the covering 902 comprises two separate outer or main layers spaced apart axially from each other on the frame 904, with one layer extending between, for example, the first row I of struts 920 and the fourth row IV of struts, and the other layer extending along the fifth row V such that the frame openings 918 are uncovered. The openings 916 of the main layer 906 can have any size or shape, can be located at any location along the axis of the prosthetic valve, and/or at different axial locations. The openings 916 can also have any suitable circumferential spacing.

Figure 45:
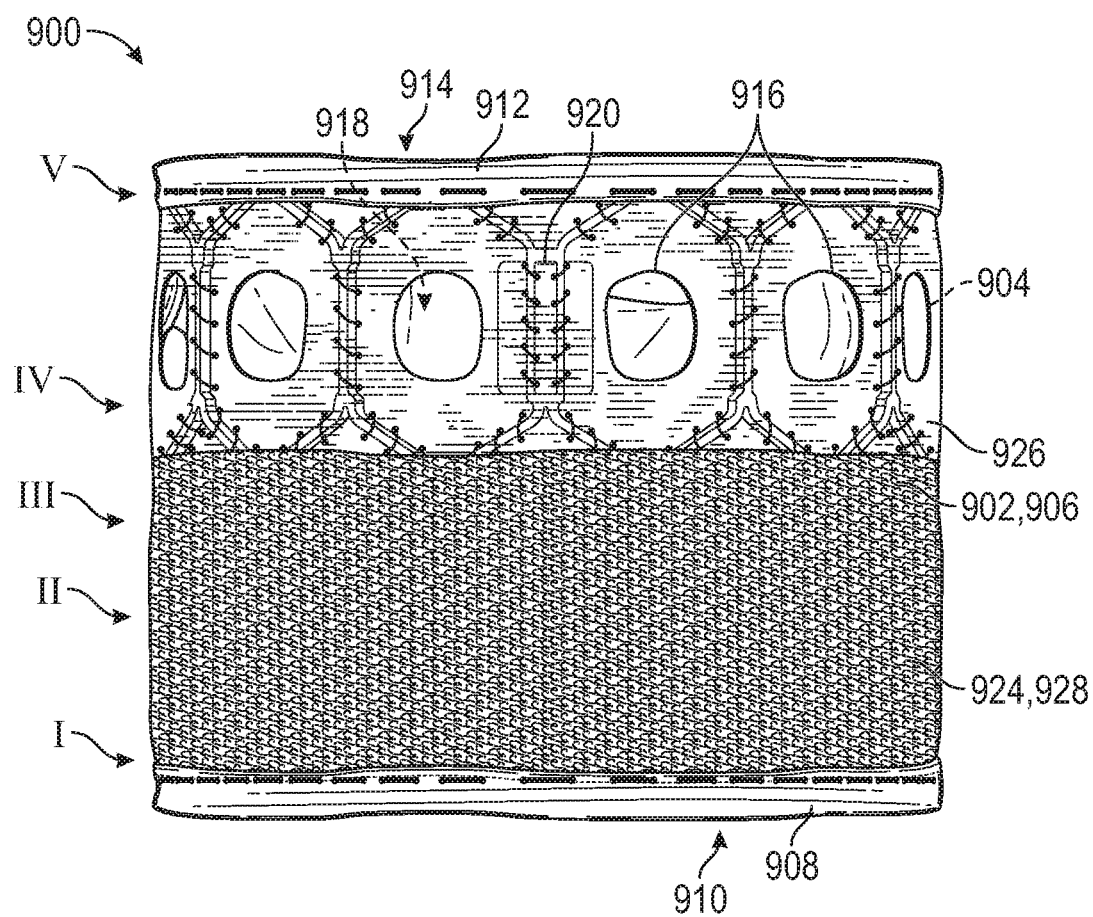

FIG. 45 illustrates an example of the prosthetic valve 900 in which the main layer 906 (which can form part or all of a sealing member or cover member) of the outer covering 902 comprises a first portion 924 including a plush (e.g., knitted) pile layer 928 similar to the covering 414 of FIG. 19, and a second portion 926 without a pile. Additional portions are also possible. The plush pile layer 928 of the first portion 924 can extend circumferentially around the frame 904, and axially along the frame 904 from the inflow end portion 910 to the level of the fourth row IV of struts 920. The second portion 926 can define a plurality of round openings 916 positioned over the frame openings 918, and having an area smaller than the frame openings 918, although the openings 916 can have any size, shape, location, and/or spacing. The pile layer 928 can be configured to extend along any portion of the axis of the prosthetic valve.

In certain embodiments, the first portion 924 and the second portion 926 comprise different pieces of material. For example, in some embodiments, the first portion 924 is a knitted fabric comprising the plush pile layer 928 described above, and the second portion 926 is a knitted fabric without a pile layer. The first and second portions 924, 926 can be configured to overlap each other (e.g., a portion of the first portion 924 may extend over the second portion 926 where the two pieces of fabric meet). The second portion 926 can also have a different knit pattern than the first portion 924, and can also comprise strands (e.g., yarns, etc.) having different properties (e.g., denier, material, surface characteristics such as texturing, number of filaments, number of plies, number of twists, etc.) from the strands/yarns of the first portion 924. In some embodiments the first portion 924 and/or the second portion 926 comprise knit patterns formed using a two bar system, a three bar system, a four bar system, etc., or as many as an eight bar system. The first portion 924 and/or the second portion 926 can be knitted in a variety of ways, e.g., using a circular technique, a crochet technique, a tricot technique, a raschel technique, other techniques, or combinations thereof. The properties of the second portion 926 can be optimized to allow the openings 916 to be created more easily (e.g., by laser cutting), and to ensure that the fabric retains its structural integrity. For example, cloth or fabric made of certain types of woven strands or woven yarns may be more likely to fall apart and/or fray if openings are cut therein, so the second portion 926 could be made of a bias cloth or bias fabric that is less likely to fall apart or fray when openings are cut therein. Optionally, the first and second portions 924, 926 can comprise a single piece of fabric. In some embodiments, the first portion 924 and/or the second portion 926 comprise a non-woven material (e.g., foam, felt, etc.).

Including openings such as the openings 916 in the outer covering 902 may promote blood flow through the covering from the interior of the prosthetic valve to the exterior such that the struts 920 and the radially-outward surfaces of the leaflets 922 are bathed or washed by blood flowing through the prosthetic valve during valve operation. This may help to reduce blood stasis around the strut members 920, and between the struts 920 and the leaflets 922, which may potentially reduce the risk of thrombosis.

Figure 46:
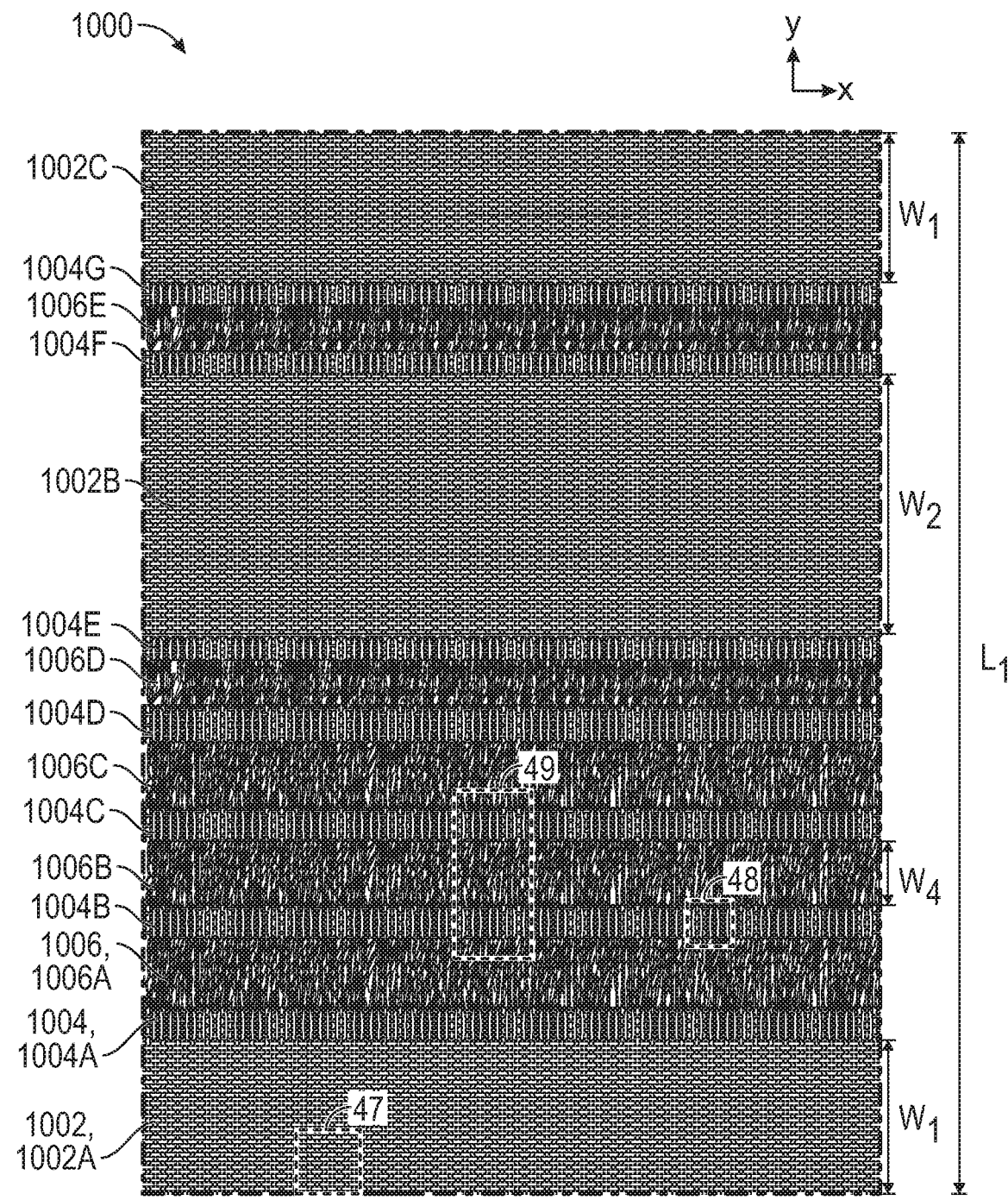
FIG. 46 is a plan view of an example of a sealing member or a cover member for a prosthetic heart valve including woven portions and floating portions configured as floating yarn portions.

FIGS. 46-51 show an example of a main cushioning layer or sealing member/cover member 1000. The sealing member 1000 can comprise a fabric body having a plurality of different portions working together, such as a plurality first portions (e.g., woven portions, multiple sets of woven portions, etc.) and a plurality of second portions (e.g., elastic, stretchable portions configured as floating portions, such as floating yarn portions), which can be incorporated into any of the prosthetic valve outer coverings described herein. FIG. 46 illustrates the sealing member/cover member 1000 in a laid-flat configuration where the x-axis corresponds to the circumferential direction and the y-axis corresponds to the axial direction when the sealing member is attached to a frame of a prosthetic valve. The sealing member 1000 can comprise a plurality of first portions (such as first woven portions 1002 configured as woven strips or stripes extending along the x-axis), a plurality of second portions (such as second woven portions 1004 configured as woven strips or stripes extending along the x-axis), a plurality of third portions (e.g., floating portions or floating yarn portions, strips, or stripes 1006 extending along the x-axis), and/or optionally additional portions. The various woven and floating portions/floating yarn portions can be spaced apart from each other along the y-axis. In the illustrated configuration, the first woven portions 1002 comprise a weave pattern that is different from the weave pattern of the second woven portions 1004, as described in greater detail below.

In one example configuration, as illustrated, the sealing member/cover member 1000 comprises a first woven portion 1002A, which can be at the lower or inflow edge of the sealing member/cover member. Moving in a direction along the positive y-axis, the sealing member/cover member 1000 can further comprise a second woven portion 1004A, a floating portion/floating yarn portion 1006A, a second woven portion 1004B, a floating portion/floating yarn portion 1006B, a second woven portion 1004C, a floating portion/floating yarn portion 1006C, a second woven portion 1004D, a floating portion/floating yarn portion 1006D, a second woven portion 1004E, a first woven portion 1002B, a second woven portion 1004F, a floating portion/floating yarn portion 1006E, a second woven portion 1004G, and a first woven portion 1002C at the opposite end of the sealing member/cover member from the first woven portion 1002A. In other words, the first woven portion 1002B and each of the floating portions/floating yarn portions 1006A-1006E can be located between two second woven portions 1004 such that the first woven portion 1002B and each of the floating portion/floating yarn portions 1006A-1006E are bounded or edged in a direction along the x-axis by respective second woven portions 1004.

Figure 48:
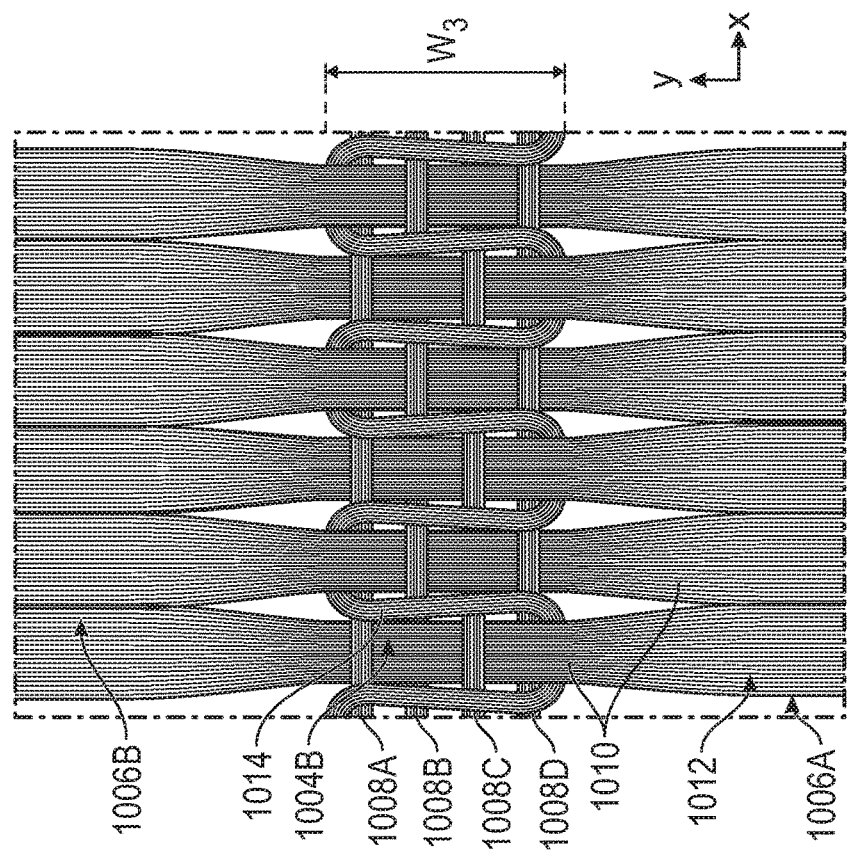
FIG. 48 is a magnified view of a second woven portion of the sealing member or cover member of FIG. 46.
Figure 47:
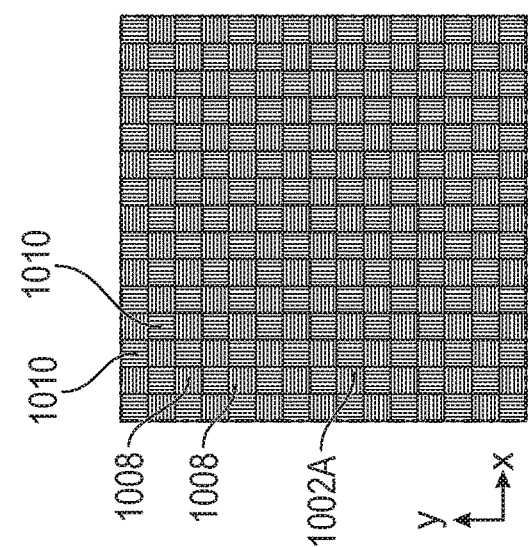
FIG. 47 is a magnified view of a first woven portion of the sealing member or cover member of FIG. 46.

Referring to FIGS. 47 and 48, the main layer or sealing member/cover member 1000 can comprise a plurality of first strands 1008 (e.g., yarns, etc.) oriented generally along the x-axis and a plurality of second yarns 1010 oriented generally along the y-axis. In certain configurations, the first strands/yarns 1008 are warp strands/yarns, meaning that during the weaving process the strands/yarns 1008 are held by the loom, while the second strands/yarns 1010 are weft strands/yarns, which are interwoven with the warp strands/yarns by a moving shuttle or weft-carrying mechanism during the weaving process. However, in some embodiments the first strands/yarns 1008 can be weft strands/yarns and the second strands/yarns 1010 can be warp strands/yarns.

Each of the first strands/yarns 1008 and the second strands/yarns 1010 can comprise a plurality of constituent filaments 1012 that are spun, wound, twisted, intermingled, interlaced, etc., together to form the respective strands/yarns. Exemplary individual filaments 1012 of the second strands/yarns 1010 can be seen in FIGS. 48-50. In some embodiments, the first strands/yarns 1008 have a denier of from about 1 D to about 200 D, about 10 D to about 100 D, about 10 D to about 80 D, about 10 D to about 60 D, or about 10 D to about 50 D. In some embodiments, the first strands/yarns 1008 have a filament count of 1 to about 600 filaments per strand/yarn, about 10 to about 300 filaments per strand/yarn, about 10 to about 100 filaments per strand/yarn, about 10 to about 60 filaments per strand/yarn, about 10 to about 50 filaments per strand/yarn, or about 10 to about 30 filaments per yarn. In some embodiments, the first strands/yarns 1008 have a denier of about 40 D and a filament count of 24 filaments per yarn. The first strands/yarns 1008 can also be twisted strands/yarns or non-twisted strands/yarns. In the illustrated embodiment, the filaments 1012 of the first strands/yarns 1008 are not texturized. However, in some embodiments, the first strands/yarns 1008 can comprise texturized filaments.

The second strands/yarns 1010 can be texturized strands/yarns comprising a plurality of texturized filaments 1012. For example, the filaments 1012 of the second strands/yarns 1010 can be texturized, for example, by twisting the filaments, heat-setting them, and untwisting the filaments as described above. In some embodiments, the second strands/yarns 1010 have a denier of from about 1 D to about 200 D, about 10 D to about 100 D, about 10 D to about 80 D, or about 10 D to about 70 D. In some embodiments, a filament count of the second strands/yarns 1010 is between 1 filament per strand/yarn to about 100 filaments per strand/yarn, about 10 to about 80 filaments per strand/yarn, about 10 to about 60 filaments per strand/yarn, or about 10 to about 50 filaments per yarn. In some embodiments, the second strands/yarns 1010 have a denier of about 68 D and a filament count of about 36 filaments per yarn.

The first strands/yarns 1008 and the second strands/yarns 1010 can be woven together to form the woven portions of the sealing member/cover member, as noted above. For example, in the first woven portions 1002A-1002C, the first and second strands/yarns 1008, 1010 can be woven together in a plain weave pattern in which the second strands/yarns 1010 (e.g., the weft strands/yarns) pass over a first strand/yarn 1008 (e.g., a warp yarn) and then under the next first strand/yarn in a repeating pattern. This weave pattern is illustrated in detail in FIG. 47. In some embodiments, the density of the first strands/yarns 1008 is from about 10 strands/yarns per inch to about 200 strands/yarns per inch, about 50 strands/yarns per inch to about 200 strands/yarns per inch, or about 100 strands/yarns per inch to about 200 strands/yarns per inch. In certain embodiments, the first woven portion 1002A and the first woven portion 1002C can be configured as selvedge (selvage) portions, and can have a lower strand/yarn density than the first woven portion 1002B to facilitate assembly on a valve frame. Other weave patterns can also be used, such as over two under two, over two under one, etc. The first woven portions can also be woven in plain weave derivative patterns such as twill, satin, or combinations of any of these.

In the second woven portions 1004A-1004G, the first and second strands/yarns 1008, 1010 can be interwoven in another pattern that is different from the weave pattern of the first woven portions 1002A-1002C. For example, in the illustrated embodiment, the first and second strands/yarns 1008, 1010 are woven together in a leno weave pattern in the second woven portions 1004A-1004G. FIG. 48 illustrates the leno weave of the second woven portion 1004B in greater detail. With reference to FIG. 48, the leno weave can comprise one or more leno strands/yarns or "leno ends" 1014, and four first strands/yarns 1008A, 1008B, 1008C, and 1008D, also referred to as "warp ends." The pattern illustrated in FIG. 48 includes a single leno strand/yarn 1014 in the manner of a half-leno weave. However, in some embodiments, the leno weave pattern can be a full-leno weave comprising two intertwining leno strands/yarns 1014, or other leno-derived weaves. Examples of half-leno weaves, full-leno weaves, and associated weaving techniques are illustrated in FIGS. 55A-55J.

In the half-leno weave illustrated in FIG. 48, the first strands/yarns 1008A-1008D can extend parallel to the x-axis, and the second strands/yarns 1010 can be interwoven with the first strands/yarns 1008A-1008D in, for example, a plain weave. The leno strand/yarn 1014 can weave around the first strands/yarns 1008A-1008D such that the leno strand/yarn 1014 crosses over, or on top of, the first strands/ yarns 1008A-1008D with each pass in the positive y-direction, crosses beneath or behind the next second yarn 1010 in the x-direction, and extends back over the first strands/yarns 1008A-1008D in the negative y-direction. This pattern can be repeated along the length of the second woven portion 1004B. In this manner, the second woven portions 1004 can be relatively narrow, strong woven portions spaced axially from each other along the frame when the sealing element is mounted to a frame. The leno strand/yarn 1014 can serve to keep the first strands/yarns 1008A-1008D and the second strands/yarns 1010 in place with respect to each other as the prosthetic valve is crimped and expanded, and can impart strength to the second woven portions 1004 while minimizing width.

In certain embodiments, each of the second woven portions 1004A-1004G comprise the leno weave pattern described above. In some embodiments, one or more of the second woven portions 1004A-1004G is configured differently, such as by incorporating more or fewer first strands/yarns 1008 in the leno weave, having multiple leno ends woven around multiple groupings of strands/yarns 1008, etc. In some embodiments, a chemical locking method is used where the leno weave and/or a plain weave includes warp strands/yarns having core-sheath construction filaments. The sheath of the individual filaments can be made of low-melt temperature polymers such as biocompatible polypropylene, and the core of the filaments be made of another biocompatible polymer such as polyester. After the weaving process, the heat setting process described below can enable the softening and/or melting of the sheath. Upon cooling, the softened sheath polymer can bond the core polyester filaments together. This can create a bonded body enabling locking of the woven structure.

Referring again to FIG. 46, the floating portions or floating yarn portions 1006 can comprise strands/yarns extending in only one axis between respective second woven portions 1004 that are spaced apart from each other along the y-axis. For example, taking the floating portion/floating yarn portion 1006A as a representative example, the floating portion/floating yarn portion 1006A can comprise a plurality of second strands/yarns 1010 that exit the leno weave of the second woven portion 1004A, extend across the floating portion/floating yarn portion 1006A, and are incorporated into the leno weave of the second woven portion 1004B without being interwoven with any other strands/yarns in the floating portion/floating yarn portion. In some embodiments, the density of the second strands/yarns in the floating portion/floating yarn portions 1006 is from about 10 to about 200 strands/yarns per inch, about 50 to about 200 strands/yarns per inch, or about 100 to about 200 strands/yarns per inch. In some embodiments, the density of the second strands/yarns 1010 is about 60-80 strands/yarns per inch. In some embodiments, the floating portions/floating yarn portions include first strands/yarns 1008 disposed under or over, but not interwoven with, the second strands/yarns 1010 such that the second strands/yarns float over the first strands/yarns or vice versa. The floating portions or floating yarn portions can also be configured as any other elastically stretchable structure, such as elastically stretchable woven, knitted, braided, or non-woven fabrics, or polymeric membranes, to name a few, that is elastically stretchable at least in the axial direction of the prosthetic valve.

In the illustrated embodiment, each of the woven portions 1002A-1002C and 1004A-1004G, and each of the floating portions 1006A-1006E have width dimensions in the y-axis direction. The widths of the constituent portions can be configured such that the overall length $L_1$ (FIG. 46) of the sealing member/cover member 1000 generally corresponds to the axial length of a prosthetic heart valve in the expanded configuration. For example, in the illustrated embodiment the first woven portions 1002A and 1002C each have a width $W_1$. In certain embodiments, the width $W_1$ is configured such that portions of the first woven portions 1002A and 1002C can be folded over the respective inflow and/or outflow ends of the frame of a prosthetic valve.

Figure 52:
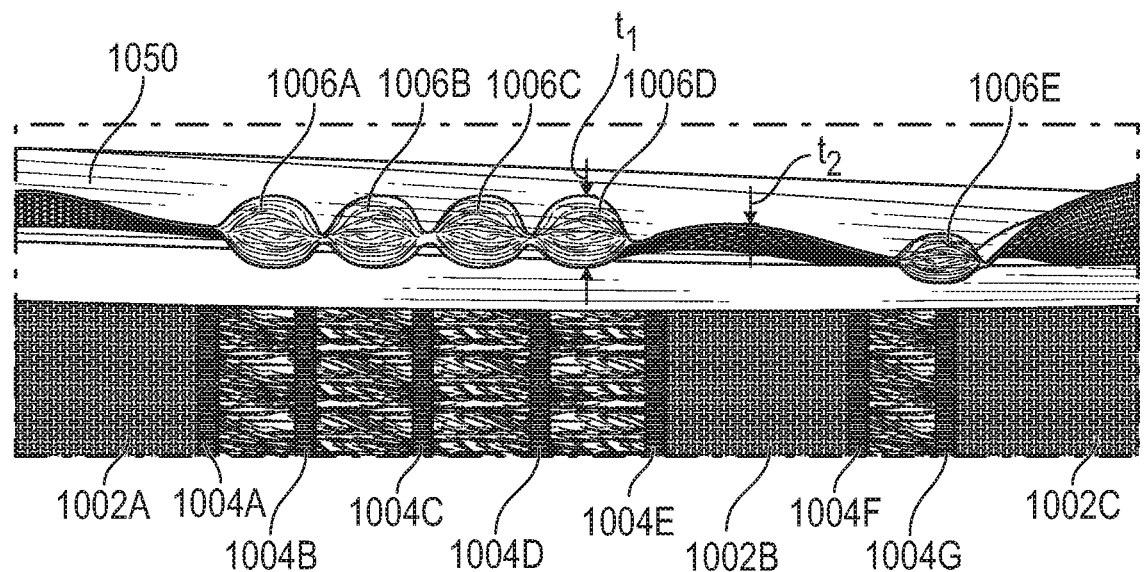
FIG. 52 is a perspective view illustrating an edge portion of the sealing member or cover member of FIG. 46.

The first woven portion 1002B can have a width $W_2$. With reference to FIG. 52, when the sealing member/cover member 1000 is used in combination with the frame of the Edwards Lifesciences SAPIEN® 3 prosthetic heart valve, the width $W_2$ can be configured to correspond to the axial dimension of the frame openings defined by the strut members between the fourth row IV and the fifth row V of struts, as described in greater detail below. In some embodiments, the width $W_2$ of the first woven portion 1002B is about 2 mm to about 20 mm, about 2 mm to about 12 mm, or about 3 mm to about 10 mm. In some embodiments, the width $W_2$ is about 7 mm.

The second woven portions 1004A-1004G can have widths $W_3$ (FIG. 48). In the illustrated embodiment, all of the second woven portions 1004A-1004G have the width $W_3$, but one or more of the second woven portions can also have different widths. In certain embodiments, the width $W_3$ can be relatively short, such as about 0.1 mm to about 3 mm, about 0.1 mm to about 2 mm, or about 0.1 mm to about 1 mm. In some embodiments, the width $W_3$ is about 1 mm.

Figures 49, 50:
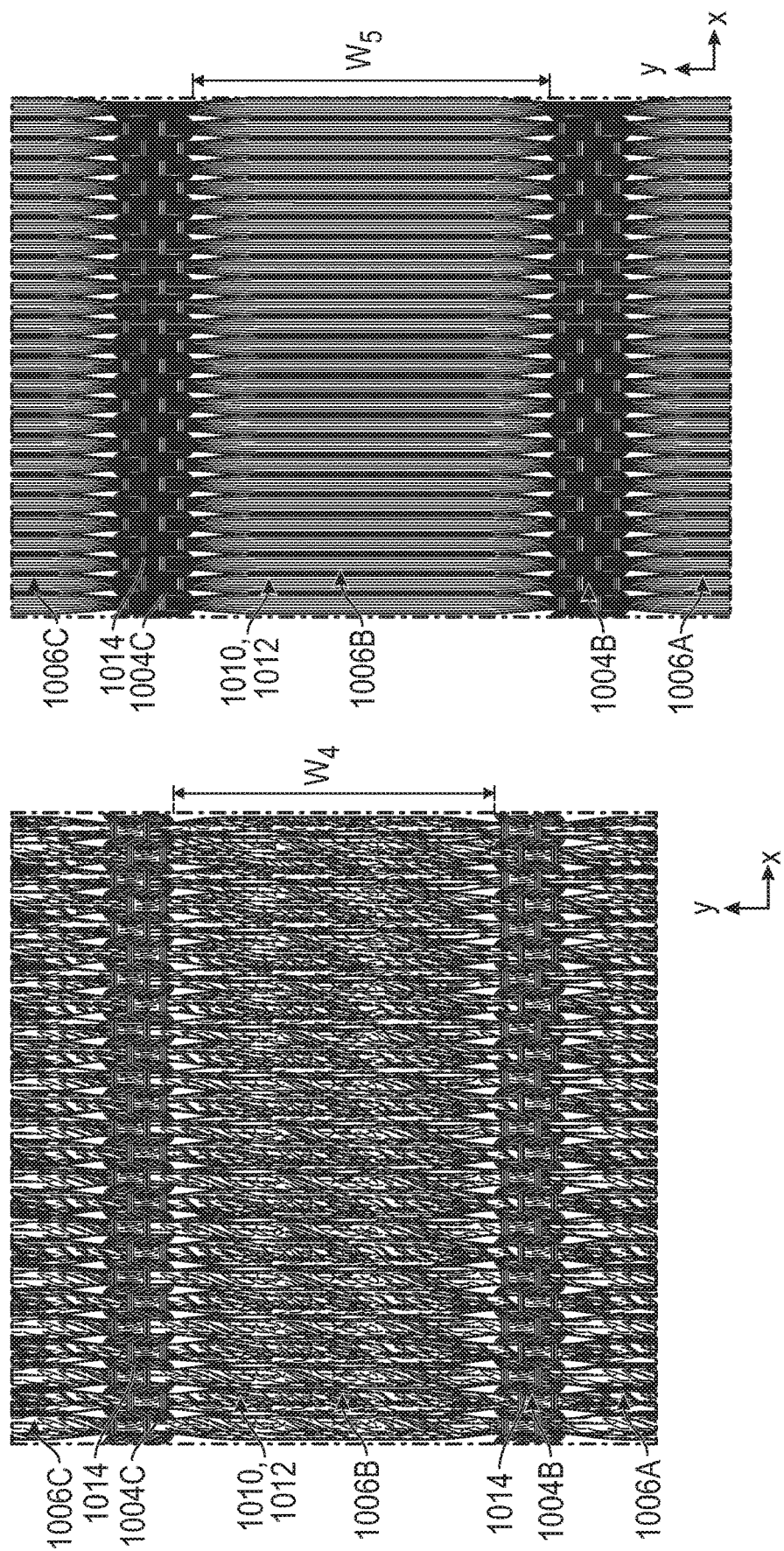
FIG. 49 is a magnified view of a floating yarn portion of the sealing member or cover member of FIG. 46 in a relaxed state.
FIG. 50 illustrates the floating yarn portion of FIG. 49 in a stretched state.

With reference to FIGS. 46 and 49-52, in certain embodiments, the sealing member/cover member 1000, and in particular the floating portions/floating yarn portions 1006A-1006E, are resiliently stretchable between a first, natural, or relaxed configuration (FIGS. 46 and FIG. 49) corresponding to the radially expanded state of the prosthetic valve, and a second, elongated, or tensioned configuration (FIGS. 50 and 51) corresponding to the radially compressed state of the prosthetic valve. Thus, the floating portions 1006A-1006E can have initial widths $W_4$ when the sealing member 1000 is in the relaxed, unstretched state. FIG. 49 illustrates a portion of the floating portion 1006B in the natural, relaxed state. When the fabric is in the relaxed state, the textured filaments 1012 of the second strands/yarns 1010 can be kinked and twisted in many directions such that the floating portion 1006B has a bulky, billowy, or pillow-like quality, and provides a compressible volume or bulk. When tensioned, the kinks, twists, etc., of the filaments 1012 can be pulled at least partially straight along the y-axis, causing the second strands/yarns 1010 to elongate. With reference to FIG. 50, the width of the floating portions 1006 can thus increase to a second width $W_5$ that is larger than the initial width $W_4$.

Figure 51:
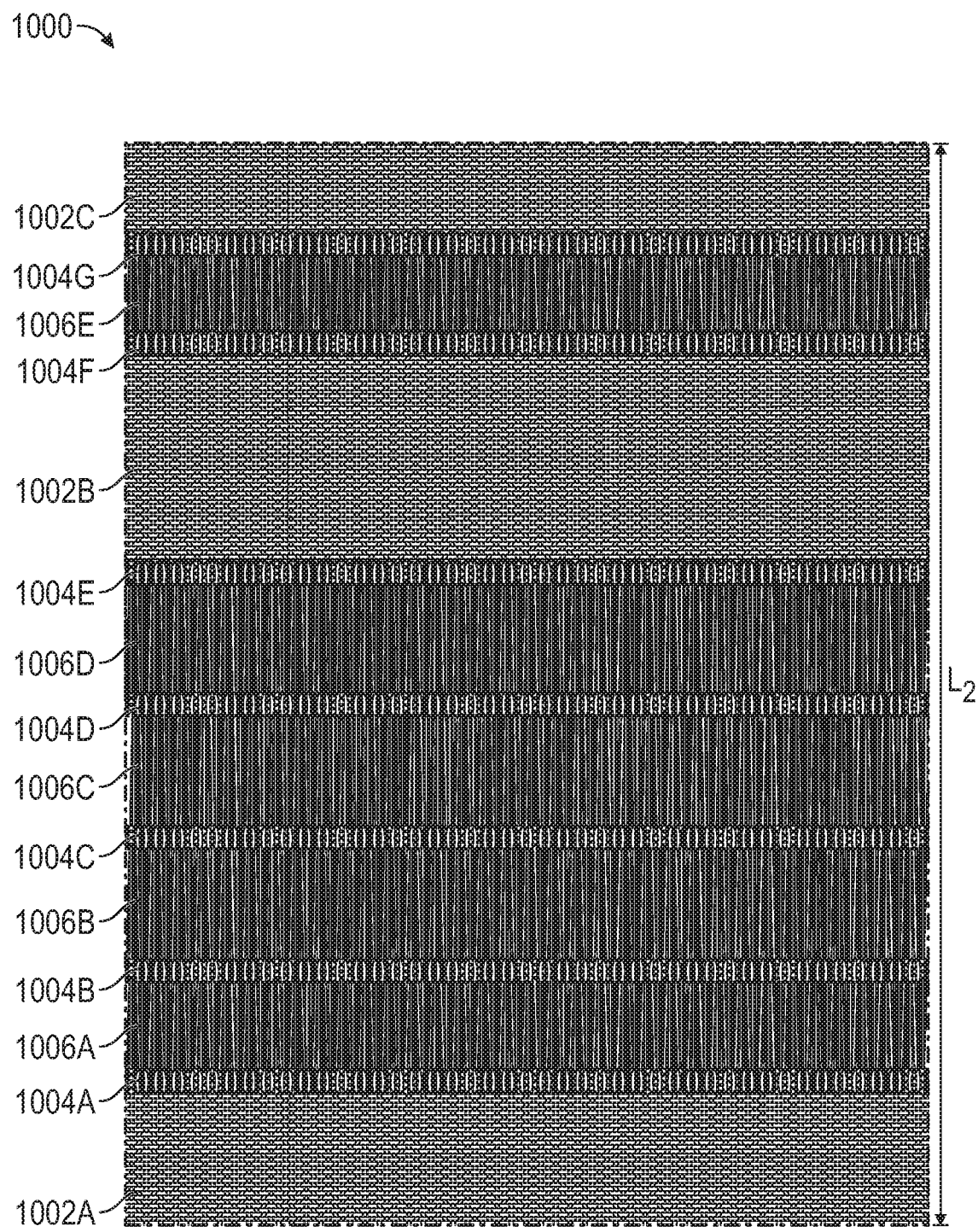
FIG. 51 is a plan view of the sealing member or cover member of FIG. 46 in a stretched state.

The cumulative effect of the floating portions/floating yarn portions 1006A-1006E increasing in width from the initial width $W_4$ to the second width $W_5$ is that the overall axial dimension of the sealing member/cover member 1000 can increase from the initial length $L_1$ (FIG. 46) to a second overall length $L_2$ (FIG. 51) that is greater than the first length $L_1$. FIG. 51 illustrates the sealing member 1000 in the stretched configuration with the second strands/yarns 1010 of the floating yarn portions 1006A-1006E straightened under tension such that the overall length of the sealing member increases to the second length $L_2$. In certain embodiments, the size, number, spacing, etc., of the floating yarn portions 1006, and the degree of texturing of the constituent second strands/yarns 1010, can be selected such that the second length $L_2$ of the sealing member 1000 corresponds to the length of a frame of a prosthetic valve when the prosthetic valve is crimped for delivery on a delivery apparatus, as described below with reference to FIGS. 53 and 54. In some embodiments, the relaxed initial width $W_4$ of the floating yarn portions 1006 is about 1 mm to about 10 mm, about 1 mm to about 8 mm, or about 1 mm to about 5 mm. In some embodiments, the initial width $W_4$ is about 4 mm.

FIG. 52 illustrates an edge portion of the sealing member/cover member 1000 gripped between a pair of grippers 1050. In certain embodiments, the bulky, billowy nature of the texturized strands/yarns 1010 in the floating portions/floating yarn portions 1006 results in the floating portions/floating yarn portions 1006 having a thickness $t_1$ that is greater than a thickness $t_2$ of the woven portions 1002 and 1004. For example, in certain embodiments the thickness $t_1$ of the floating portions 1006 is two times, three times, four times, five times, six times, or even ten times greater than the thickness $t_2$ of the woven portions 1002 and 1004, or more, when the sealing member is in the relaxed state. This can allow the floating portions 1006 to cushion the native leaflets between the valve body and/or against an anchor or ring into which the prosthetic valve is implanted. The floating portions 1006 can also occupy voids or space in the anatomy, and/or promote tissue growth into the floating portions, as in the embodiments described above. When tension is applied to stretch the floating portions 1006, the thickness $t_1$ can decrease as the texturized second strands/yarns 1010 straighten. In certain embodiments, the thickness $t_1$ is equal or nearly equal to the thickness $t_2$ of the woven portions 1002 and 1004 when the sealing member is in the tensioned state. When the tension on the sealing member 1000 is released, such as during expansion of the prosthetic valve, the strands/yarns 1012 can resume their texturized shape and the thickness of the floating portions 1006 can return to the initial thickness $t_1$.

Figure 53:
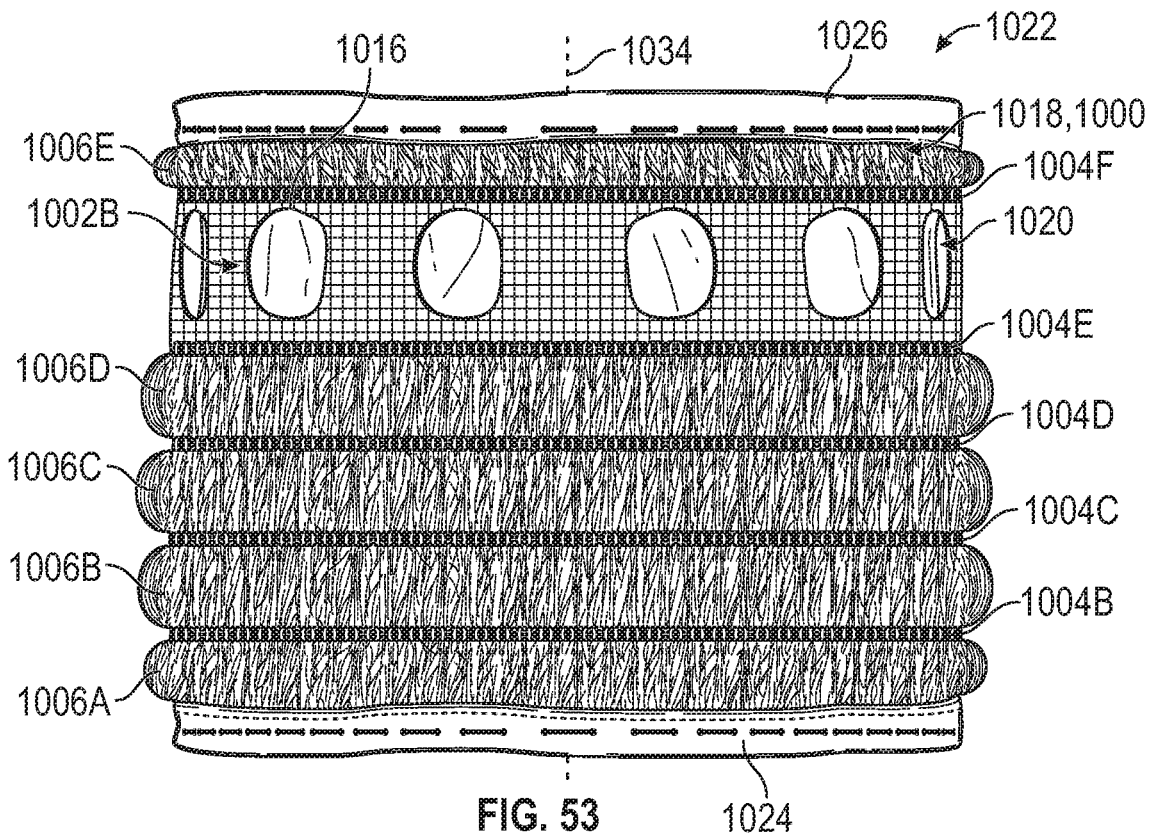
FIG. 53 is a side elevational view of a prosthetic heart valve having an outer covering including the sealing member or cover member of FIG. 46, according to one embodiment.

FIG. 53 illustrates the sealing member 1000 formed into an outer covering 1018 and assembled onto the frame 1020 of a prosthetic valve 1022. In the illustrated embodiment, the frame 1020 is the frame of the Edwards Lifesciences SAPIEN® 3 prosthetic heart valve similar to the frames described above, although the sealing member 1000 can be configured for use on other prosthetic valves as well, including the frame in FIG. 56. The outer covering 1018 can also include an inflow protection portion 1024 and an outflow protection portion 1026 similar to the outer coverings described above, and can be configured for implantation in a native valve, such as the mitral valve, tricuspid valve, aortic valve, pulmonary valve, Eustachian valve, etc., although in some embodiments the outer covering need not include the inflow and/or the outflow protection portions, and can be configured for implantation in other heart valves or body lumens as well. The sealing member 1000 can be oriented such that the second woven portions 1004A-1004G and the floating portions/floating yarn portions 1006A-1006E extend circumferentially around the frame 1020, and such that the floating portion/floating yarn portion 1006A is adjacent the inflow protection portion 1024 at the inflow end of the prosthetic valve. In this configuration, the texturized second strands/yarns 1010 extend in a direction along the longitudinal axis 1034 of the prosthetic valve. In the illustrated embodiment, the first woven portion 1002A and the second woven portion 1004A can be disposed at least partially beneath the inflow protection portion 1024 and are not visible in the figure. Similarly, the first woven portion 1002C and the second woven portion 1004G can be disposed at least partially beneath the outflow protection portion 1026 and are also not visible in the figure.

Still referring to FIG. 53, the outer covering 1018 can be secured to the frame by attachment means, for example, suturing, adhering, etc., the sealing member 1000 to the frame 1020 along one or more of the second woven portions 1004A-1004G. The first woven portion 1002B can also comprise a plurality of circumferentially spaced-apart openings 1016. The openings 1016 can be sized and positioned to overlie corresponding openings defined by the frame struts between the fourth row IV of struts and the fifth row V of struts, similar to the embodiment of FIG. 43 above. In some embodiments, the sealing member 1000 is incorporated into an outer covering in the state illustrated in FIG. 46 without openings in the first woven portion 1002B.

Figure 54:
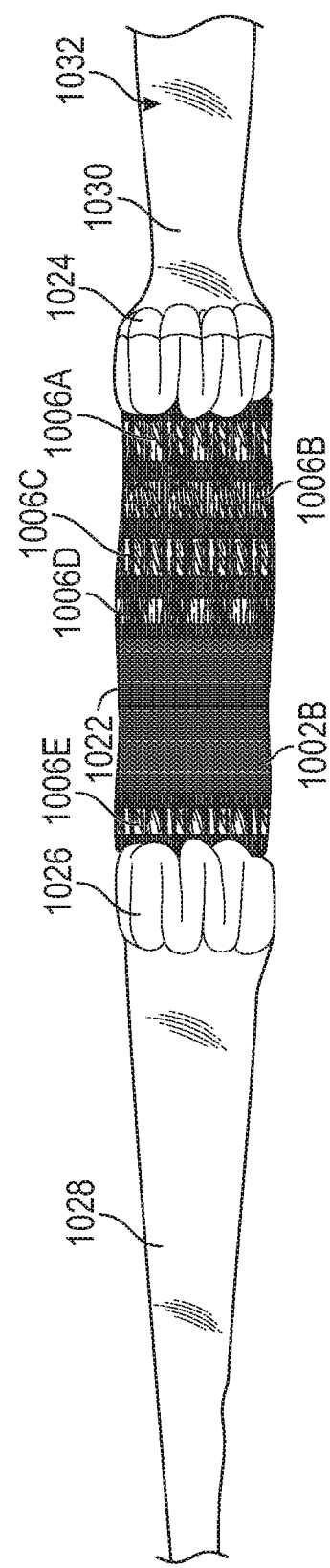
FIG. 54 illustrates the prosthetic heart valve of FIG. 53 crimped onto a balloon at the distal end of a delivery apparatus.

FIG. 54 illustrates the prosthetic valve 1022 crimped for delivery on a balloon 1028 at the distal end of a balloon catheter 1030 of a delivery apparatus 1032. Further details of representative delivery systems that can be used with the prosthetic valves described herein can be found in U.S. Publication No. 2017/0065415 and U.S. Pat. No. 9,339,384, which are incorporated herein by reference. As shown in the example illustrated in FIG. 53, the floating portions/floating yarn portions 1006A-1006E are elongated and the texturized second strands/yarns 1010 are at least partially straightened, allowing the sealing member 1000 to lengthen to accommodate the increased length of the crimped frame 1020. In certain embodiments, the floating portions/floating yarn portions 1006A-1006E are configured such that the sealing member 1000 can elongate by about 10% to about 500%, about 10% to about 300%, about 10% to about 200%, about 10% to about 100%, about 10% to about 80%, or about 10% to about 50%. In some embodiments, the floating portions/floating yarn portions 1006A-1006E are configured to allow the sealing member 1000 to elongate by about 30%, corresponding to the elongation of the frame 1022 between the expanded and crimped configurations. As noted above, the increase in width of the floating portions/floating yarn portions 1006A-1006E can also result in a corresponding decrease in thickness of the floating portions/floating yarn portions, reducing the crimp profile of the prosthetic valve during delivery.

In some embodiments, the first and second strands/yarns 1008 and 1010 can comprise any of various biocompatible thermoplastic polymers such as PET, Nylon, ePTFE, UHMWPE, etc., or other suitable natural or synthetic fibers. In certain embodiments, the sealing member 1000 can be woven on a loom, and can then be heat-treated or heat-set to achieve the desired size and configuration. For example, depending upon the material selected, heat-setting can cause the sealing member 1000 to shrink. Heat-setting can also cause a texturizing effect, or increase the amount of texturizing, of the second strands/yarns 1010. After heat treatment, the openings 1016 can be created in the first woven portion 1002B (e.g., by laser cutting), and the sealing member can be incorporated into and/or form an outer covering such as the covering 1018 for assembly onto a prosthetic valve. In some embodiments, the openings 1016 can also be created before heat treatment.

In certain embodiments, the loops, filaments, floating portions, floating yarn portions, etc., of the prosthetic sealing members described herein can be configured to promote a biological response in order to form a seal between the prosthetic valve and the surrounding anatomy. In certain configurations, the sealing members described herein can be configured to form a seal over a selected period of time. For example, in certain embodiments, the open, porous nature of the loops, filaments, strands/yarns, etc., can allow a selected amount of paravalvular leakage around the prosthetic valve in the time period following implantation. The amount of paravalvular leakage past the seal structure may be gradually reduced over a selected period of time as the biological response to the loops, filaments, strands/yarns, etc., causes blood clotting, tissue ingrowth, etc. In some embodiments, the sealing members, and in particular the loops, filaments, strands/yarns, etc., of the paravalvular sealing structure, are treated with one or more agents that inhibit the biological response to the sealing structures. For example, in certain embodiments, the loops, filaments, strands/yarns, etc., are treated with heparin. In certain embodiments, the amount or concentration of the agent(s) is selected such that the agents are depleted after a selected period of time (e.g., days, weeks, or months) after valve implantation. As the agent(s) are depleted, the biological response to the loops, filaments, strands, yarns, etc., of the sealing structures may increase such that a paravalvular seal forms gradually over a selected period of time. This may be advantageous in patients suffering from heart remodeling, such as left atrial or left ventricular remodeling (e.g., due to mitral regurgitation, etc.), by providing an opportunity for the remodeling to reverse as regurgitation past the prosthetic valve is gradually reduced.

Figure 55A:
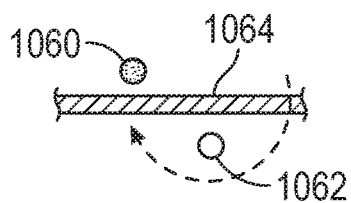
FIGS. 55A-55J illustrate various examples of leno weave patterns and leno weaving techniques.
Figure 55B:
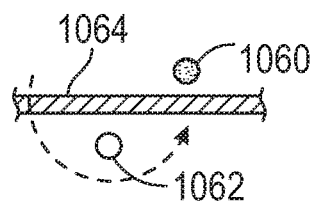

FIGS. 55A-55J illustrate various leno weaves and leno weaving techniques that can be used to produce the sealing member/cover member 1000, or any of the other sealing members/cover members described herein. FIG. 55A is a cross-sectional view illustrating a shed (e.g., the temporary separation of warp strands/yarns to form upper and lower warp strands/yarns) in which a leno yarn, "leno end," or "crossing end" 1060 forms the top shed on the left of the figure above a weft strand/yarn 1064 and a standard warp strand/yarn 1062 forms the bottom shed. FIG. 55B illustrates a successive shed in which the leno strand/yarn 1060 forms the top shed on the right of the standard warp strand/yarn 1062. In FIGS. 55A and 55B, the leno strand/yarn 1060 can cross under the standard strand/yarn 1062 in a pattern known as bottom douping. Alternatively, the leno strand/yarn 1060 can cross over the standard strand/yarn 1062, known as top douping, as in FIGS. 55H and 55I.

Figure 55C:
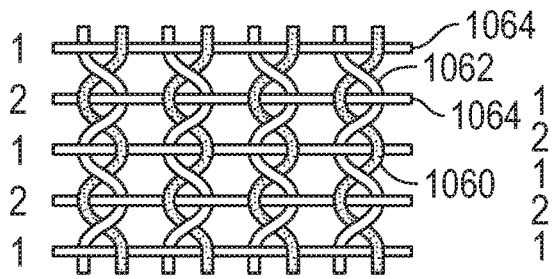
Figure 55D:
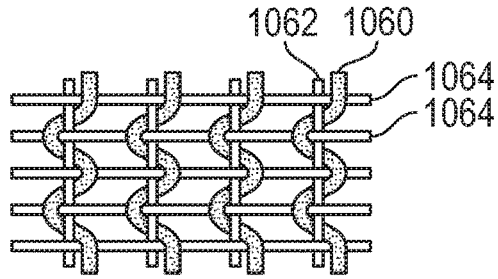

FIG. 55C illustrates a leno weave interlacing pattern produced when one warp beam is used on a loom, and the distortion or tension of the leno strands/yarns 1060 and the standard strands/yarns 1062 is equal such that both the strands/yarns 1060 and the strands/yarns 1062 curve around the weft strands/yarns 1064. FIG. 55D illustrates a leno weave lacing pattern produced when multiple warp beams are used, and the leno strands/yarns 1060 are less tensioned than the standard strands/yarns 1062 such that the standard strands/yarns 1062 remain relatively straight in the weave, and perpendicular to the weft strands/yarns 1064, while the leno strands/yarns 1060 curve around the standard strands/yarns 1062.

Figure 55E:
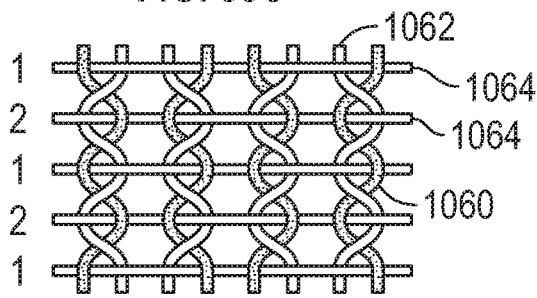
Figure 55F:
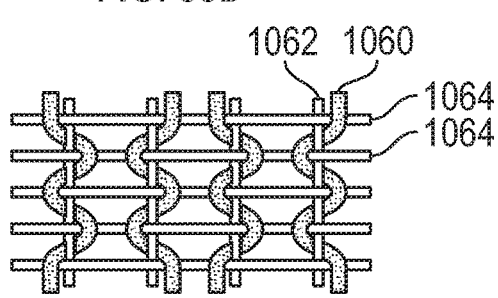

FIG. 55E illustrates an interlacing pattern corresponding to FIG. 55C, but in which alternate leno strands/yarns 1060 are point-drafted (e.g., a technique in which the leno strands/yarns are drawn through heddles) such that adjacent leno strands/yarns 1060 have opposite lacing directions. FIG. 55F illustrates an interlacing pattern corresponding to FIG. 55D, but in which the leno strands/yarns 1060 are point-drafted such that adjacent leno strands/yarns have opposite lacing directions.

Figure 55G:
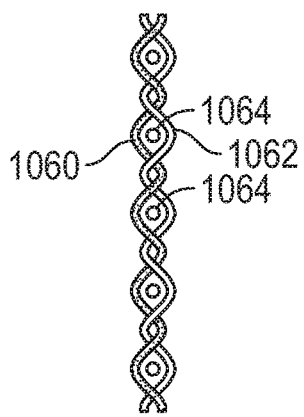
Figure 55H:
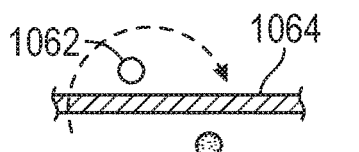
Figure 55I:
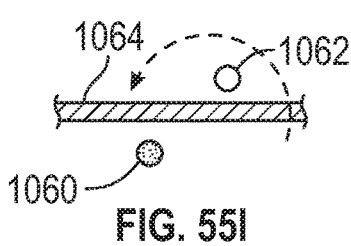

FIG. 55G is a cross-sectional view of a plain leno weave structure taken through the weft strands/yarns 1064.

Figure 55J:
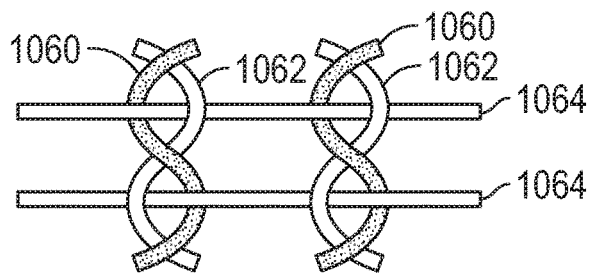

FIG. 55J illustrates a representative leno weave as viewed from the reverse side of the fabric.

The prosthetic valve covering embodiments described herein can also be used on a variety of different types of prosthetic heart valves. For example, the coverings can be adapted, and in some embodiments are adapted, for use on mechanically-expandable prosthetic heart valves, such as the valve 1100 illustrated in FIG. 56. The prosthetic valve 1100 can include an annular stent or frame 1102, and a leaflet structure 1104 situated within and coupled to the frame 1102. The frame 1102 can include an inflow end 1106 and an outflow end 1108. The leaflet structure can comprise a plurality of leaflets 1110, such as three leaflets arranged to collapse in a tricuspid arrangement similar to the aortic valve such that the leaflets form commissures 1132 where respective outflow edge portions 1134 of the leaflets contact each other. Optionally, the prosthetic valve can include two leaflets 1110 configured to collapse in a bicuspid arrangement similar to the mitral valve, or more than three leaflets, depending upon the particular application.

Figure 56:
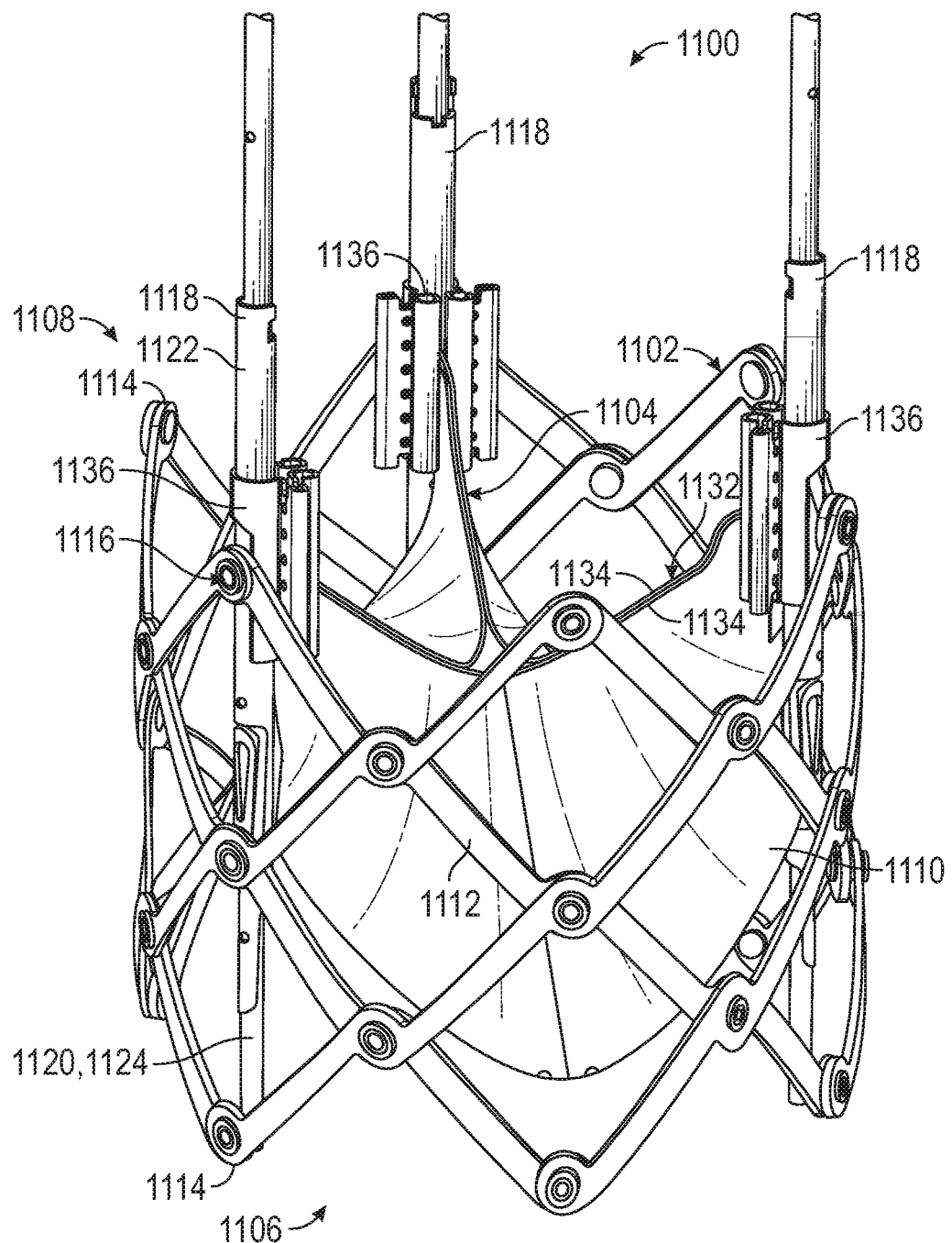
FIG. 56 is a perspective view of a mechanically-expandable prosthetic heart valve, according to one embodiment.

With reference to FIG. 56, the frame 1102 can include a plurality of interconnected lattice struts 1112 arranged in a lattice-type pattern and forming a plurality of apices 1114 at the outflow end 1108 of the prosthetic valve. The struts 1112 can also form similar apices 1114 at the inflow end 1106 of the prosthetic valve. The lattice struts 1112 can be pivotably coupled to one another by hinges 1116 located where the struts overlap each other, and also at the apices 1114. The hinges 1116 can allow the struts 1112 to pivot relative to one another as the frame 1102 is expanded or contracted, such as during assembly, preparation, or implantation of the prosthetic valve 1100. The hinges 1116 can comprise rivets or pins that extend through apertures formed in the struts 1112 at the locations where the struts overlap each other. In the embodiment of FIG. 56, the struts 1112 include apertures for five hinges 1116. However, the struts may include any number of hinges depending upon the particular size of the frame, etc. For example, in some embodiments the struts comprise seven hinges, as in the configuration shown in FIG. 57. Additional details regarding the frame 1102 and devices and techniques for radially expanding and collapsing the frame can be found in U.S. Publication No. 2018/0153689, which is incorporated herein by reference.

As illustrated in FIG. 56, the frame 1102 can comprise a plurality of actuator components 1118 that can also function as release-and-locking units (also referred to as locking assemblies) configured to radially expand and contract the frame. In the illustrated configuration, the frame 1102 comprises three actuator components 1118 configured as posts and coupled to the frame 1102 at circumferentially spaced locations, although the frame can include more or fewer actuator components depending upon the particular application. Each of the actuator components 1118 generally can comprise an inner member 1120, such as an inner tubular member, and an outer member 1122, such as an outer tubular member concentrically disposed about the inner member 1120. The inner members 1120 and the outer members 1122 can be moveable longitudinally relative to each other in a telescoping manner to radially expand and contract the frame 1102, as further described in U.S. Publication No. 2018/0153689.

In the illustrated configuration, the inner members 1120 have distal end portions 1124 coupled to the inflow end 1106 of the frame 1102 (e.g., with a coupling element such as a pin member). In the illustrated embodiment, each of the inner members 1120 are coupled to the frame at respective apices 1114 at the inflow end 1106 of the frame. The outer members 1122 can be coupled to apices 1114 at the outflow end 1108 of the frame 1102 at, for example, a mid-portion of the outer member, as shown in FIG. 56, or at a proximal end portion of the outer member, as desired.

The inner member 1120 and the outer member 1122 can telescope relative to each other between a fully contracted state (corresponding to a fully radially expanded state of the prosthetic valve) and a fully extended state (corresponding to a fully radially compressed state of the prosthetic valve). In the fully extended state, the inner member 1120 is fully extended from the outer member 1122. In this manner, the actuator components 1118 allow the prosthetic valve to be fully expanded or partially expanded to different diameters and retain the prosthetic valve in the partially or fully expanded state.

In some embodiments, the actuator components 1118 are screw actuators configured to radially expand and compress the frame 1102 by rotation of one of the components of the actuators. For example, the inner members 1120 can be configured as screws having external threads that engage internal threads of corresponding outer components. Further details regarding screw actuators are disclosed in U.S. Publication No. 2018/0153689.

The prosthetic valve 1100 can also include a plurality of commissure support elements configured as commissure clasps or clamps 1136. In the illustrated configuration, the prosthetic valve includes a commissure clamp 1136 positioned at each commissure 1132 and configured to grip the leaflets 1110 of the commissure at a location spaced radially inwardly of the frame 1102. Further details regarding commissure clamps are disclosed in U.S. Publication No. 2018/0325665, which is incorporated herein by reference.

Figure 57:
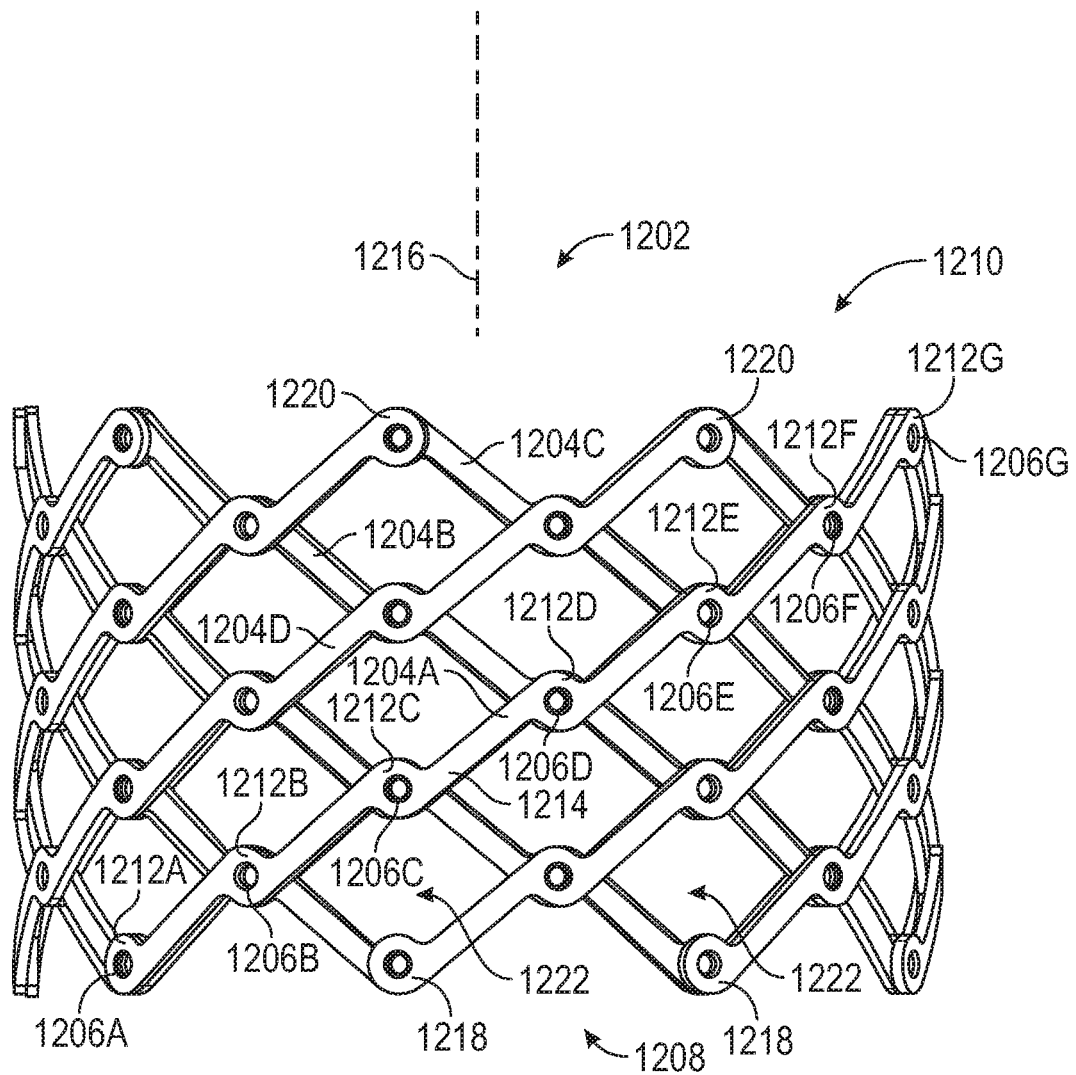
FIG. 57 is a side-elevation view of an example of a mechanically-expandable frame for a prosthetic heart valve.

FIG. 57 illustrates an example of a mechanically-expandable frame 1202 with components such as the leaflets, leaflet clamps, and actuator components removed for purposes of illustration. The frame 1202 can be similar to the frame 1102, except that the struts 1204 include seven apertures 1206 spaced apart along the length of each strut for forming hinges similar to the hinges 1116. For example, each strut 1204 can include a plurality of round, curved, or circular portions 1212 connected by straight portions or segments 1214. Each successive segment 1214 can be parallel to, but circumferentially offset from, the preceding segment 1214, as described in U.S. Publication No. 2018/0153689. Each round portion 1212 can define an aperture 1206. Thus, taking the strut member 1204A by way of example, the round portion 1212A at the inflow end 1208 of the frame 1202 can define an aperture 1206A. Moving along the strut 1204A in the direction of the outflow end 1210, the portion 1212B can define an aperture 1206B, the portion 1212C can define an aperture 1206C, the portion 1212D can define an aperture 1206D, the portion 1212E can define an aperture 1206E, the portion 1212F can define an aperture 1206F, and the portion 1212G can define an aperture 1206G at the outflow end 1210. The apertures, and the hinges formed therewith, can function substantially as described above to allow the frame to be radially collapsed for delivery and radially expanded at the treatment site.

In the illustrated configuration, the struts 1204 are arranged in two sets, with the first set being on the inside of the frame 1202, offset circumferentially from each other, and angled such that the struts extend helically around the central axis 1216 of the frame. In the embodiment of FIG. 57, struts 1204B and 1204C are part of the first or inner set of struts. The second set of struts 1204 can be disposed radially outward of the first set of struts. The second set of struts can be angled such that the apertures 1206 align with the apertures 1206 of the inner set of struts, and can be oriented with the opposite helicity as the first set of struts. In the embodiment illustrated in FIG. 57, the struts 1204A and 1204D are part of the second or outer set of struts. The inner and outer sets of struts 1204 can form inflow apices 1218 of the frame where the respective round portions 1212 align, and can form outflow apices 1220 where the respective round portions at the opposite ends of the struts align. In the expanded configuration, the struts 1204 of the inner and outer sets of struts can also define a plurality of diamond-shaped cells or openings 1222.

Figure 58:
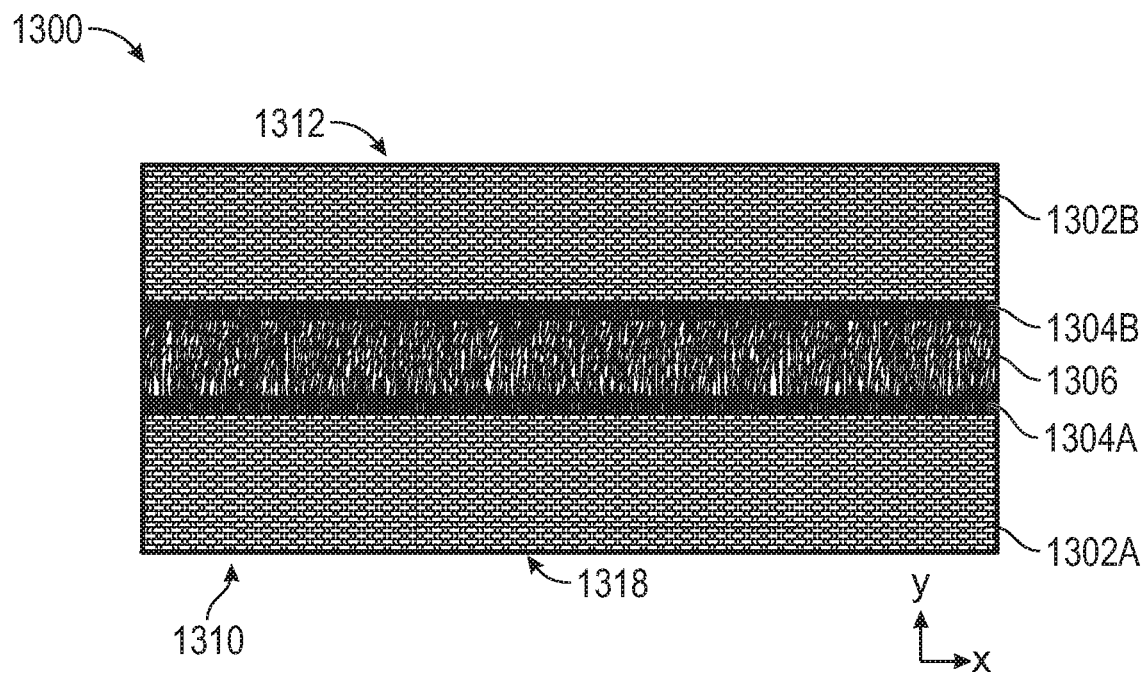
FIG. 58 is a plan view of an example of a sealing member or cover member for a prosthetic heart valve.
Figure 59:
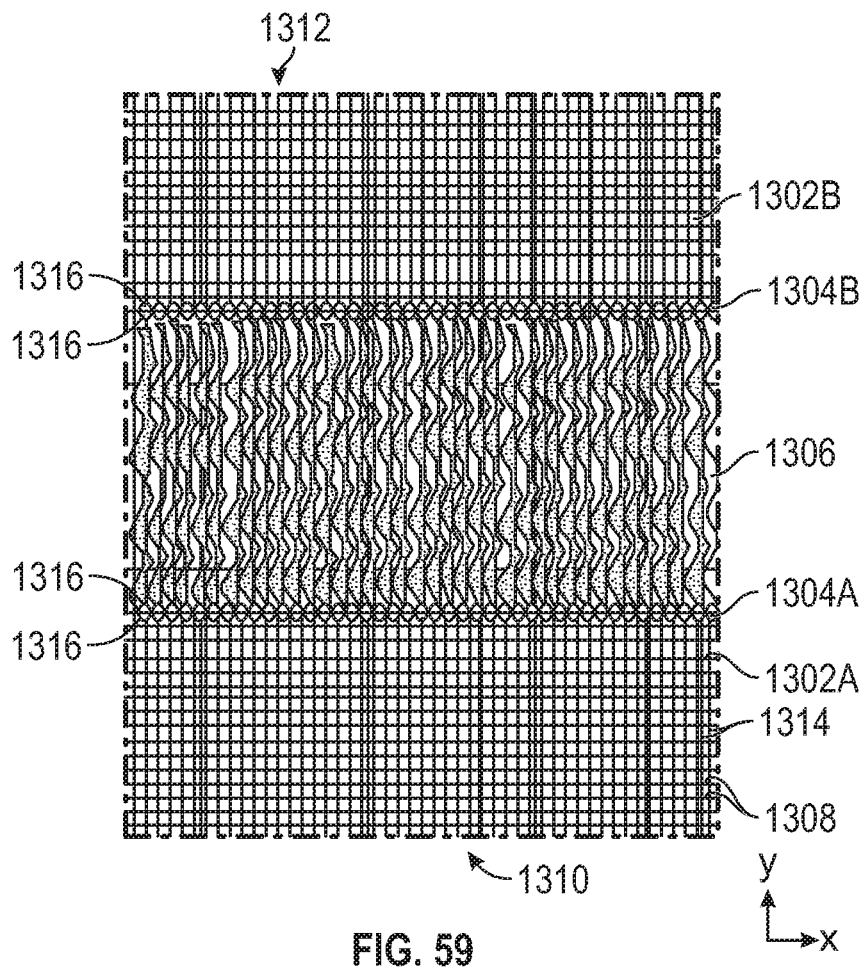
FIG. 59 is a magnified view of a portion of the sealing member or cover member of FIG. 58.

FIGS. 58 and 59 illustrate an example of a main cushioning layer, cover member, or sealing member 1300. The sealing member 1300 can comprise a fabric body having a plurality of woven portions and one or more floating portions (e.g., floating yarn portions, etc.), similar to the embodiment of FIG. 46. FIG. 58 illustrates the sealing member 1300 in a laid-flat configuration where the x-axis corresponds to the circumferential direction and the y-axis corresponds to the axial direction when the sealing member 1300 is attached to a prosthetic valve frame. FIG. 59 is a magnified view of a portion of the sealing member 1300. Beginning at the inflow end portion 1310 of the sealing member 1300, the sealing member can comprise a first woven portion 1302A. Moving in a direction along the positive y-axis, the sealing member 1300 can further comprise a second woven portion 1304A, a floating portion/floating yarn portion 1306, a second woven portion 1304B, and a first woven portion 1302B. The first woven portion 1302B is located at the outflow end portion 1312 on the opposite side of the floating portion/floating yarn portion from the first woven portion 1302A.

Still referring to FIG. 59, the sealing member 1300 can comprise strands/yarns 1308 extending in the x-direction (e.g., warp strands/yarns) and strands/yarns 1314 extending in the y-direction (e.g., weft strands/yarns), as in the examples above. In certain embodiments, at least the strands/yarns 1314 can be texturized. The texturized strands/yarns 1314 can be interwoven with the strands/yarns 1308 in the first woven portion 1302A, and in the second woven portion 1304A. The texturized strands/yarns 1314 can extend or "float" across to the second woven portion 1304B to form the floating portions/floating yarn portion 1306. The strands/yarns 1314 can reenter the weave at the second woven portion 1304B.

As in the embodiment of FIG. 46, the first woven portions 1302A and 1302B can comprise a plain weave. In some embodiments, the first woven portion 1302A and/or the first woven portion 1302B can have a strand/yarn density of from 20 strands/yarns (or ends) per inch to 150 strands/yarns per inch, such as 40 strands/yarns per inch to 120 strands/yarns per inch. In some embodiments, first woven portions 1302A and 1302B can be configured as selvedges, and can prevent the fabric from unraveling.

The second woven portion 1304A can extend along the lower edge of the floating portion/floating yarn portion 1306, and second woven portion 1304B can extend along the upper edge of the floating portion/floating yarn portion 1306. In this manner, the floating portion/floating yarn portion 1306 can be bounded or edged in a direction along the x-axis by the second woven portions 1304A and 1304B. In some configurations, the widths of the second woven portions 1304A and 1304B can be relatively small in comparison to the first woven portions 1302A and 1302B, similar to the embodiment of FIG. 46. In some embodiments, the second woven portions 1304A and 1304B comprises a leno weave pattern, such as any of the leno weave patterns described above. For example, with reference to the example in FIG. 59, each of the second woven portions 1304A and 1304B comprise two leno ends 1316 intertwined around strands/yarns 1314 and strands/yarns 1308, and may be top-douped or bottom-douped. In some embodiments, the second woven portions 1304A and 1304B comprise one leno end, or more than two leno ends.

The sealing member 1300 can be resiliently stretchable between a first, natural width corresponding to a non-tensioned state, and a second width when the sealing member is stretched in the y-direction, similar to the embodiment of FIG. 46. As in the previously described embodiments, the texturized strands/yarns 1314 of the floating portion/floating yarn portion 1306 can be configured to be provide a bulky, compressible volume when in the relaxed state. When the sealing member 1300 is tensioned in the y-direction, the texturized strands/yarns 1314 can be pulled straight, causing the sealing member to lengthen in the y-direction.

Figure 60:
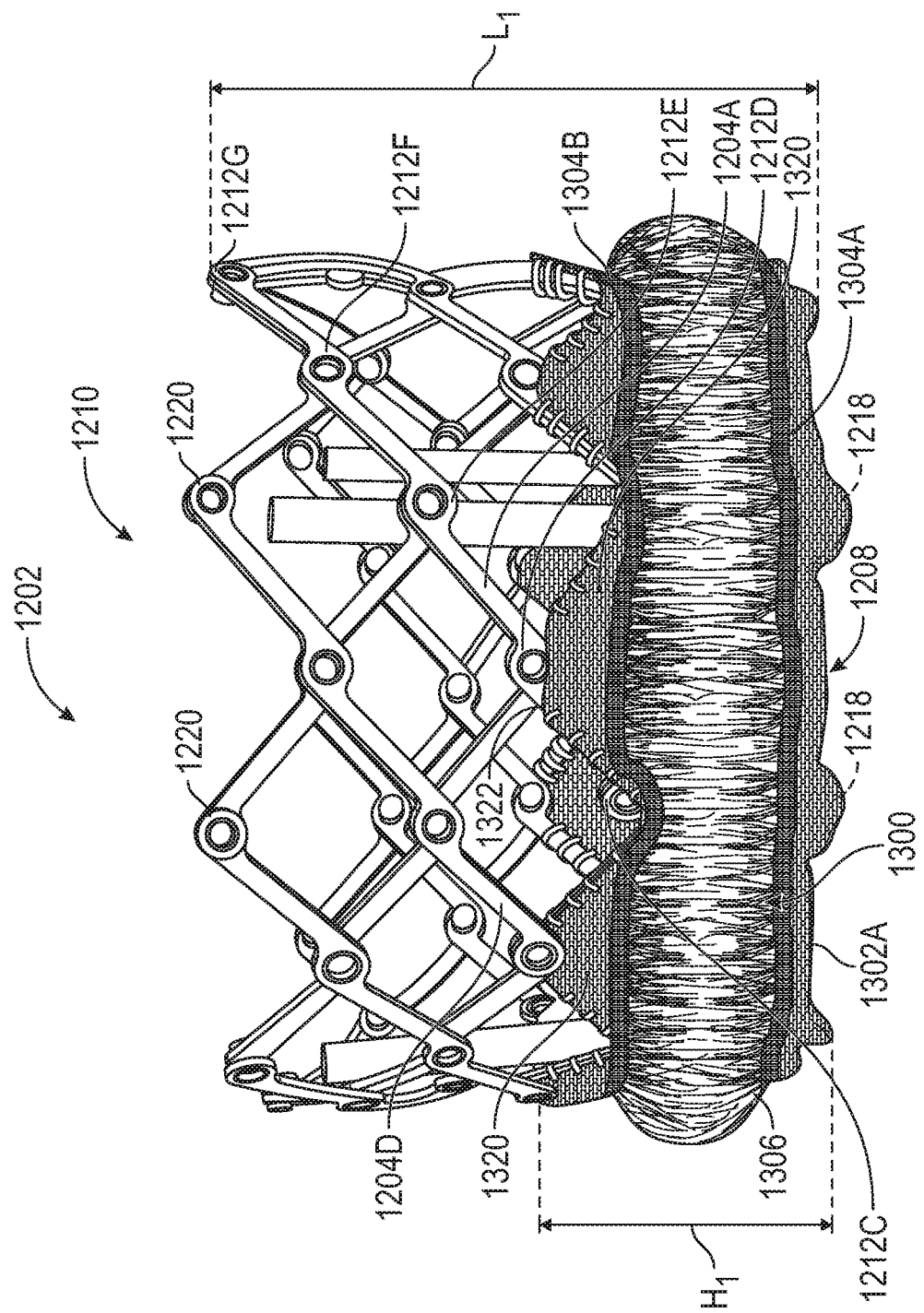
FIG. 60 is a side elevation view showing an example of a covering formed from the sealing member or cover member of FIG. 58 attached to the frame of FIG. 57 in the radially expanded configuration.
Figure 61:
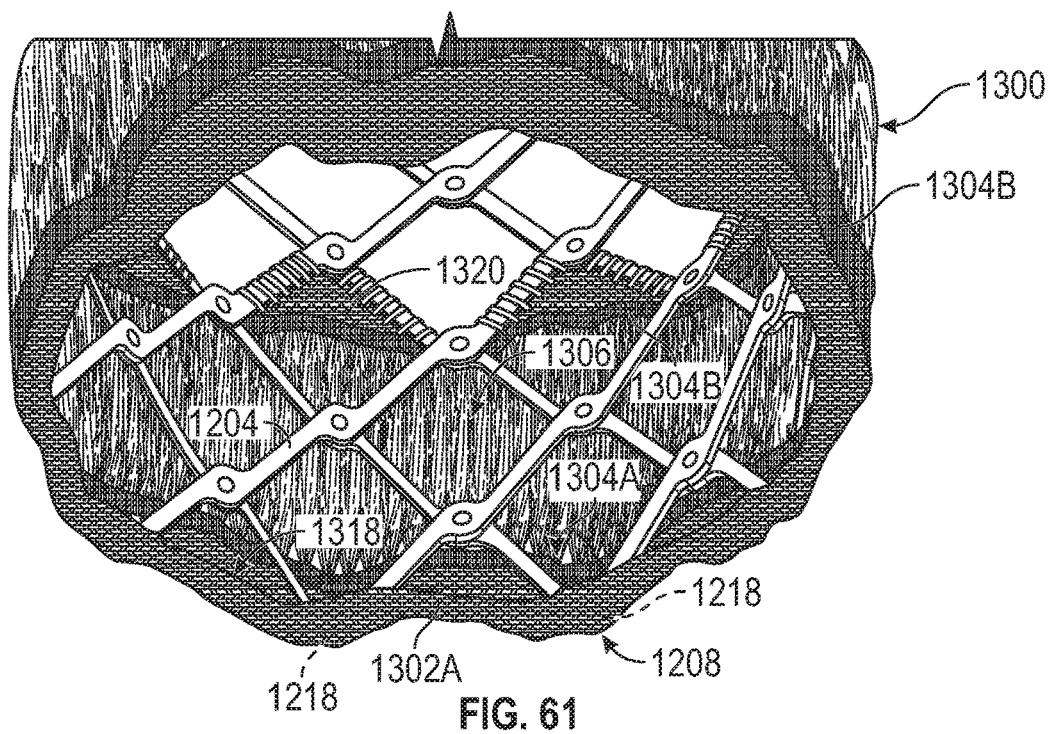
FIG. 61 is a perspective view of the inflow end portion of the frame and covering assembly of FIG. 60.

FIG. 60 illustrates the sealing member or cover member 1300 secured to the frame 1202 of FIG. 57 to form a covering on the frame. In FIG. 60, the frame is in the expanded configuration and the covering and the sealing member are in the first, relatively non-tensioned state. In the illustrated embodiment, the first woven portion 1302A can be secured (e.g., by attachment means, such as suturing, adhesive, etc.) to the inflow end portions of the struts 1204. For example, with reference to FIG. 61, the first woven portion 1302A can be folded over the inflow apices 1218 so that the free edge 1318 of the fabric is located inside the frame 1202, and so that the first woven portion 1302A covers the apices 1218.

Referring to the outer struts 1204A and 1204D of FIG. 60, the first woven portion 1302B can be sized so that it extends from approximately the level of the round portions 1212C to the round portions 1212D. In certain embodiments, the first woven portion 1302B can be shaped to match the shape of the cells 1222 (FIG. 57) formed by the struts 1204 when the frame 1202 is in the expanded configuration. For example, the first woven portion 1302B can be cut or shaped such that it comprises a plurality of extension portions 1320. The extension portions 1320 can be sized to correspond to portions of the cells 1222 that extend above the second woven portion 1304B. In the illustrated embodiment, the extension portions 1320 are tapered in the direction of flow through the valve such that they have a trapezoidal shape, such as an isosceles trapezoidal shape. However, the extension portions 1320 can have any other shape, such as a triangular shape, a rectangular shape, etc. The extension portions 1320 can be sutured to the frame 1202 along the strut segments 1214 (FIG. 57) extending between the round portions 1212C and 1212D of the struts on the outer diameter of the frame, and to the corresponding segments of the struts 1204 on the inside of the frame.

With reference to the outer set of struts 1204, the floating portion/floating yarn portion 1306 can extend between about the level of the round portions 1212B to the round portions 1212C. When the frame 1202 is in the expanded configuration, the floating portion/floating yarn portion 1306 can extend or bulge radially outwardly from the frame to form a voluminous, compressible, pillow-like structure or cushion, which can aid in sealing against the surrounding anatomy. The texturized strands/yarns of the floating portion/floating yarn portion 1306 can also provide a porous environment for tissue ingrowth.

Figure 62:
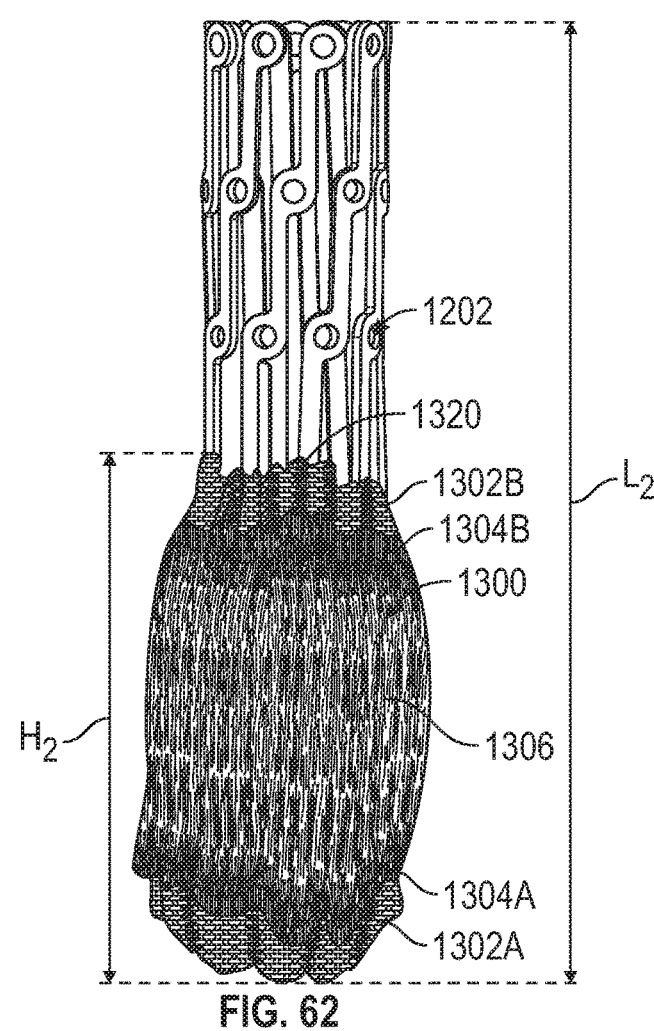
FIG. 62 is a side elevation view of the frame and covering of FIG. 60 in the radially collapsed configuration.

Still referring to FIG. 60, when the frame 1202 is in the expanded configuration, the frame can have a length $L_1$. The covering and the sealing member 1300 can have a corresponding length $H_1$, which can be measured from the inflow apices 1218 to the upper or outflow-most edge 1322 of the extension portions 1320. As illustrated in FIG. 62, when the frame 1202 is radially collapsed for delivery, the length of the frame can increase to a second length $L_2$. As the frame lengthens, the covering and the sealing member 1300, and the floating portion/floating yarn portion 1306 in particular, can also stretch such that the covering and the sealing member lengthen to a second length $H_2$ (e.g., corresponding to a second, tensioned state) to accommodate the increased length of the frame 1202. In some embodiments, the frame 1202 is configured to lengthen by 10% to 160% or more between the expanded configuration and the collapsed configuration. Thus, the covering and the sealing member 1300 can also be configured to stretch by a similar amount, such as from 10% to 200%, 10% to 180%, 10% to 160%, etc., in order to accommodate the length change of the frame.

Although the prosthetic valve covering embodiments described herein are sometimes presented in the context of mitral valve repair, it should be understood that the disclosed coverings can be used in combination with any of various prosthetic heart valves for implantation at any of the native valves in or around the heart. For example, the prosthetic valve coverings described herein can be used in combination with transcatheter heart valves, surgical heart valves, minimally-invasive heart valves, etc. The covering embodiments herein can be used in prosthetic valves intended for implantation at any of the native valve of an animal or patient (e.g., the aortic, pulmonary, mitral, tricuspid, and Eustachian valve, etc.), and include valves that are intended for implantation within existing prosthetics valves (so called "valve-in-valve" procedures). The covering embodiments can also be used in combination with other types of devices implantable within other body lumens outside of the heart, or heart valves that are implantable within the heart at locations other than the native valves, such as trans-atrial or trans-ventricle septum valves.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. A prosthetic heart valve, comprising:
 a frame comprising a plurality of strut members, the frame being radially collapsible and expandable between a collapsed configuration and an expanded configuration, the frame having an inflow end and an outflow end, and defining a longitudinal axis;
 a leaflet structure situated at least partially within the frame; and
 a covering disposed around the frame, the covering comprising:
  a first woven portion extending circumferentially around the frame, the first woven portion comprising a plurality of texturized strands extending along the longitudinal axis of the frame;
  a second woven portion extending circumferentially around the frame and spaced apart from the first woven portion along the longitudinal axis of the frame;
 wherein the texturized strands extend along the longitudinal axis of the frame from the first woven portion to the second woven portion and form a floating portion between the first woven portion and the second woven portion.

2. The prosthetic heart valve of claim 1, wherein the covering is resiliently stretchable between a first state corresponding to the radially expanded configuration of the frame, and a second state corresponding to the radially collapsed configuration of the frame.

3. The prosthetic heart valve of claim 2, wherein the floating portion is resiliently stretchable between the first state and the second state of the covering.

4. The prosthetic heart valve of claim 1, wherein the texturized strands are configured to provide compressible volume to the floating portion of the covering when the frame is in the expanded configuration.

5. The prosthetic heart valve of claim 1, wherein the texturized strands are woven into a leno weave pattern in the first woven portion and in the second woven portion.

6. The prosthetic heart valve of claim 1, wherein the covering defines a plurality of circumferentially spaced-apart openings.

7. The prosthetic heart valve of claim 6, wherein the openings in the covering overlie openings defined by strut members of the frame.

8. The prosthetic heart valve of claim 6, wherein the openings have been cut into a portion of the covering made of a bias cloth to inhibit fraying around the openings.

9. The prosthetic heart valve of claim 1, wherein the covering further comprises a third woven portion on the opposite side of the first woven portion from the floating portion, the third woven portion comprising the texturized strands of the first woven portion.

10. The prosthetic heart valve of claim 9, wherein the texturized strands are woven into a plain weave pattern in the third woven portion.

11. The prosthetic heart valve of claim 9, wherein the third woven portion is folded over apices of strut members at the inflow end of the frame.

12. The prosthetic heart valve of claim 9, wherein:
 the covering further comprises a fourth woven portion on the opposite side of the second woven portion from the floating portion; and
 the fourth woven portion comprises the texturized strands, and the texturized strands are woven into a plain weave pattern in the fourth woven portion.

13. The prosthetic heart valve of claim 12, wherein the fourth woven portion comprises a plurality of extension portions that overlie openings defined by the strut members of the frame when the frame is in the expanded configuration.

14. The prosthetic heart valve of claim 13, wherein the extension portions are tapered in a direction toward the outflow end of the frame.

15. The prosthetic heart valve of claim 1, wherein the frame is at least one of a mechanically-expandable frame and a plastically-expandable frame.

16. The prosthetic heart valve of claim 1, wherein the covering comprises a plurality of floating portions spaced apart from each other along the longitudinal axis of the frame.

17. The prosthetic heart valve of claim 1, wherein the floating portions are heat set to make them softer and/or more texturized.

18. The prosthetic heart valve of claim 1, wherein twisted PET strands are used in a warp direction and textured PET strands are used in a weft direction.

19. The prosthetic heart valve of claim 18, wherein the twisted PET strands in the warp direction are arranged to weave in leno pattern and the textured PET strands in the weft direction form the floating portion without any weave structure.

20. The prosthetic heart valve of claim 19, wherein the coverings is heat shrunk to achieve a stretchability between 80-160% and wherein the frame is a mechanically-expandable frame.

21. The prosthetic heart valve of claim 1, wherein the covering comprises at least one of a low-friction layer or low-friction coating on a least a portion thereof.

22. The prosthetic heart valve of claim 21, wherein the low-friction layer or low-friction coating is formed via electrospinning.

23. The prosthetic heart valve of claim 1, further comprising strips of material that are helically wrapped around struts and apices at an end of the frame.

24. The prosthetic heart valve of claim 1, wherein:
the covering comprises a first protective portion folded over apices of the strut members at the inflow end of the frame; and
the covering further comprises a second protective portion folded over apices of the strut members at the outflow end of the frame.

* * * * *